US011130750B2

(12) United States Patent
Richardson et al.

(10) Patent No.: US 11,130,750 B2
(45) Date of Patent: Sep. 28, 2021

(54) CALCIUM CHANNEL INHIBITORS

(71) Applicant: Cavion, Inc., Charlottesville, VA (US)

(72) Inventors: Thomas E. Richardson, Chapel Hill, NC (US); Michelle Higgin, Apex, NC (US); Timothy MacDonald, Charlottesville, VA (US)

(73) Assignee: CAVION, INC., Charlottesville, VA (US)

( * ) Notice: Subject to any disclaimer, the term of this patent is extended or adjusted under 35 U.S.C. 154(b) by 8 days.

(21) Appl. No.: 16/486,399

(22) PCT Filed: Feb. 15, 2018

(86) PCT No.: PCT/US2018/018356
§ 371 (c)(1),
(2) Date: Aug. 15, 2019

(87) PCT Pub. No.: WO2018/152317
PCT Pub. Date: Aug. 23, 2018

(65) Prior Publication Data
US 2020/0385367 A1    Dec. 10, 2020

Related U.S. Application Data

(60) Provisional application No. 62/459,355, filed on Feb. 15, 2017.

(51) Int. Cl.
| C07D 413/12 | (2006.01) |
| A61K 31/5377 | (2006.01) |
| C07D 405/12 | (2006.01) |
| A61P 25/08 | (2006.01) |
| C07D 235/14 | (2006.01) |

(52) U.S. Cl.
CPC ............ *C07D 405/12* (2013.01); *A61P 25/08* (2018.01); *C07D 235/14* (2013.01)

(58) Field of Classification Search
CPC   C07D 413/12; C07D 235/04; A61K 31/5377; A61K 31/4184; A61P 25/08; A61P 25/14
USPC ............. 544/139; 514/234.5, 394; 548/304.4
See application file for complete search history.

(56) References Cited

U.S. PATENT DOCUMENTS

| 4,680,310 | A | * | 7/1987 | Hengartner | ............... | A61P 9/12 |
| | | | | | | 514/539 |
| 4,808,605 | A | | 2/1989 | Branca et al. | | |
| 6,451,991 | B1 | | 9/2002 | Martin et al. | | |
| 7,319,098 | B2 | | 1/2008 | Cho et al. | | |
| 8,133,998 | B2 | | 3/2012 | Pajouhesh et al. | | |
| 8,586,619 | B2 | | 11/2013 | Wu et al. | | |
| 2001/0049447 | A1 | | 12/2001 | Li et al. | | |
| 2003/0158143 | A1 | | 8/2003 | Gleave et al. | | |
| 2005/0245535 | A1 | | 11/2005 | Hangeland et al. | | |
| 2008/0293786 | A1 | | 11/2008 | Hahn et al. | | |
| 2009/0270413 | A1 | | 10/2009 | Galemmo, Jr. et al. | | |
| 2009/0325979 | A1 | | 12/2009 | Choi et al. | | |
| 2010/0004286 | A1 | | 1/2010 | Cho et al. | | |
| 2010/0056545 | A1 | | 3/2010 | Shin et al. | | |
| 2010/0094006 | A1 | | 4/2010 | Nam et al. | | |
| 2010/0216841 | A1 | | 8/2010 | Barrow et al. | | |
| 2014/0155444 | A1 | | 6/2014 | Tung et al. | | |
| 2018/0280357 | A1 | | 10/2018 | Maricich et al. | | |
| 2020/0163943 | A1 | | 5/2020 | Maricich et al. | | |
| 2020/0197377 | A1 | | 6/2020 | Maricich | | |

FOREIGN PATENT DOCUMENTS

| EP | 0177960 | 4/1986 |
| EP | 1568695 | 8/2005 |
| EP | 1757590 | 2/2007 |
| KR | 2009044924 | 5/2009 |
| KR | 101679262 | 11/2016 |
| WO | WO 1993004047 | 3/1993 |
| WO | WO 2004035000 | 4/2004 |
| WO | WO 2005007124 | 1/2005 |
| WO | WO 2005009392 | 2/2005 |
| WO | WO 2006023881 | 3/2006 |
| WO | WO 2006023883 | 3/2006 |
| WO | WO 2006098969 | 9/2006 |
| WO | WO 2007002361 | 1/2007 |
| WO | WO 2007002884 | 1/2007 |
| WO | WO 2007007852 | 1/2007 |
| WO | WO 2007073497 | 6/2007 |
| WO | WO 2007120729 | 10/2007 |
| WO | WO 2008007835 | 1/2008 |
| WO | WO 2008018655 | 2/2008 |
| WO | WO 2008033447 | 3/2008 |
| WO | WO 2008033456 | 3/2008 |
| WO | WO 2008033460 | 3/2008 |
| WO | WO 2008033464 | 3/2008 |
| WO | WO 2008033465 | 3/2008 |

(Continued)

OTHER PUBLICATIONS

Database PubChem compound Jun. 14, 2012, "Compound Summary for CID 57173592".
EP Extended European Search Report in European Appln. No. 18755079.3, dated Oct. 23, 2020, 8 pages.
Bailus et al., "The prospect of molecular therapy for Angelman syndrome and other monogenic neurologic disorders," BMC Neurosci., Jun. 2014, 15:76.
Blom et al., "Preparative LC-MS Purification: Improved Compound Specific Method Optimization," J Comb. Chem., 2004, 6(6):874-883.
Bourinet et al., "Silencing of the Cav3.2 T-type calcium channel gene in sensory neurons demonstrates its major role in nociception," EMBO J., 2005, 24(2):315-324.
Carter et al., "Humanization of an anti-p185HER2 antibody for human cancer therapy," Proc. Natl. Acad. Sci. USA, May 1992, 89(10):4285-9.

(Continued)

*Primary Examiner* — Charanjit Aulakh
(74) *Attorney, Agent, or Firm* — Morrison & Foerster LLP

(57) ABSTRACT

The present disclosure describes carbamate analogs of mibefradil, as well as their compositions and methods of use. The compounds block the activity of one or more isoforms of voltage-gated calcium channels and are useful in the treatment of diseases including, e.g., cancer.

21 Claims, No Drawings

(56) References Cited

FOREIGN PATENT DOCUMENTS

| WO | WO 2008050200 | 5/2008 |
|----|---------------|--------|
| WO | WO 2008110008 | 9/2008 |
| WO | WO 2008117148 | 10/2008 |
| WO | WO 2009009015 | 1/2009 |
| WO | WO 2009035307 | 3/2009 |
| WO | WO 2009054982 | 4/2009 |
| WO | WO 2009054983 | 4/2009 |
| WO | WO 2009054984 | 4/2009 |
| WO | WO 2009056934 | 5/2009 |
| WO | WO 2009146539 | 12/2009 |
| WO | WO 2009146540 | 12/2009 |
| WO | WO 2010083264 | 7/2010 |
| WO | WO 2010141842 | 12/2010 |
| WO | WO 2011109262 | 11/2011 |
| WO | WO 2012094615 | 7/2012 |
| WO | WO 2013169857 | 11/2013 |
| WO | WO 2014110409 | 7/2014 |
| WO | WO 2017070680 | 4/2017 |

OTHER PUBLICATIONS

Casillas-Espinosa et al., "Z944, a novel selective t-type calcium channel antagonist delays the progression of seizures in the amygdala kindling model," PLOS One, Aug. 14, 2015, 10(8):1-12.
Cech, "Ribozymes and their medical implications," JAMA, Nov. 1988, 260(20):3030-4.
Flatters, "T-type calcium channels: a potential target for the treatment of chronic pain," Drugs Future, 2005, 30(6):573-580.
Gadde et al., "Combination therapy of zonisamide and bupropion for weight reduction in obese women: a preliminary, randomized, open-label study," Journal of Clinical Psychiatry, 68(8):1226-9, Aug. 2007.
Giordanetto et al., "T-type calcium channels inhibitors: a patent review," Expert Opin. Ther. Pat., Jan. 2011, 21(1):85-101.
Haselof et al., "Simple RNA enzymes with new and highly specific endoribonuclease activities," Nature, Aug. 1988, 334(6183):585-91.
Huang et al., "Topoisomerase inhibitors unsilenced the dormant allele of Ube3a in neurons," Nature, Jan. 2012, 481(7380):185-89.
Huguenard et al., "Intrathalamic rhythmicity studied in vitro: nominal T-current modulation causes robust antioscillatory effects," J Neuroscience, 1994, 14(9):5485-5502.
Jefferies et al., "A catalytic 13-mer ribozyme," Nucleic Acids Res., Feb. 1989, 17(4):1371-7.
Jones et al., "Replacing the complementarity-determining regions in a human antibody with those from a mouse," Nature, May-Jun. 1986, 321(6069):522-25.
Kim et al., "Three-dimensional model of the active site of the self-splicing rRNA precursor of Tetrahymena," Proc. Natl. Acad. Sci. USA, Dec. 1987, 84(24):8788-92.
McGivern, "Targeting N-type and T-type calcium channels for the treatment of pain," Drug Discovery Today, 2006, 11(5-6):245-53.

Miller et al., "Mapping genetic modifiers of survival in a mouse model of Dravet syndrome," Genes Brain Behav., Feb. 2014, 13(2):163-172.
Nolt et al., "Assessment of anticonvulsant effectiveness and safety in patients with Angelman's syndrome using an Internet questionnaire," American journal of health-system pharmacy, Dec. 2003, 60(24):2583-7.
Pasek et al., "Differential CaMKII regulation by voltage-gated calcium channels in the striatum," Mol. Cell. Neurosci., Sep. 2015, 68:234-43.
PCT International Preliminary Report on Patentability in International Appln. No. PCT/US2018/29616, dated Oct. 29, 2019, 5 pages.
PCT International Preliminary Report on Patentability in International Appln. No. PCT/US2016/058487, dated May 3, 2018, 7 pages.
PCT International Preliminary Report on Patentability in International Appln. No. PCT/US2018/029610, dated Oct. 29, 2019, 5 pages.
PCT International Search Report and Written Opinion in International Appln. No. PCT/US2016/058487, dated Jan. 3, 2017, 27 pages.
PCT International Search Report and Written Opinion in International Appln. No. PCT/US2018/18356, dated May 8, 2018, 9 pages.
PCT International Search Report and Written Opinion in International Appln. No. PCT/US2018/29616, dated Jul. 11, 2018, 7 pages.
PCT Internationl Search Report and Written Opinion in International Appln. No. PCT/US2018/29610, dated Jul. 19, 2018, 7 pages.
Peturssion et al., "Protecting Groups in Carbohydrate Chemistry," J Chem. Educ., 1997, 74(11):1297-1303.
Powell et al., "Low threshold T-type calcium channels as targets for novel epilepsy treatments," British Journal of Clinical Pharmacology, Jul. 2013, 77(5):729-739.
PUBCHEM-CID 57173592, dated Jun. 14, 2012.
Radin et al., "Treatment of Obese Female and Male SHHF/Mccfacp Rats with Antihypertensive Drugs, Nifedipine and Enalapril: Effects on Body Weight, Fat Distribution, Insulin Resistance and Systolic Pressure," Obesity research, Nov. 1993, 1(6):433-442.
Riechmann et al., "Reshaping human antibodies for therapy," Nature, Mar. 1988, 332(6162):323-27.
Silva-Santos et al., "Ube3a reinstatement identifies distinct developmental windows in a murine Angelman syndrome model," J. Clin. Invest., May 2015, 125(5):2069-2076.
Sims et al., "A humanized CD18 antibody can block function without cell destruction," J. Immunol., Aug. 1993, 151(4):2296-308.
Still et al., "Rapid chromatographic technique for preparative separations with moderate resolution," J Org. Chem., 1978, 43(14):2923-2925.
Verhoeyen et al., "Reshaping human antibodies: grafting an antilysozyme activity," Science, Mar. 1988, 239(4847):1534-36.
Yamauchi et al., "Neuronal Ca2+/calmodulin-dependent protein kinase II—discovery, progress in a quarter of a century, and perspective: implication for learning and memory," Biological and Pharmaceutical Bulletin, May 2005, 28(8):1342-1354.

* cited by examiner

CALCIUM CHANNEL INHIBITORS

CROSS-REFERENCE TO RELATED APPLICATIONS

This application is a national phase application under 35 U.S.C. § 371 of PCT International Application number PCT/US2018/018356, filed Feb. 15, 2018, which claims the benefit of U.S. Provisional Application Ser. No. 62/459,355, filed on Feb. 15, 2017, the entire disclosures of which are incorporated herein in their entirety.

TECHNICAL FIELD

The present application is related to pharmaceutically useful compounds. The disclosure provides new compounds as well as their compositions and methods of use. The compounds of the invention block the activity of one or more isoforms of voltage-gated calcium channels and are therefore useful in the treatment of diseases related to abnormal activity of voltage-gated calcium channels including, e.g., cancer.

BACKGROUND

T-type calcium channels are low-voltage activated calcium channels that open during membrane depolarization and mediate calcium influx into cells after an action potential or depolarizing signal. T-type calcium channels known to be present within cardiac and smooth muscle, and also are present in many neuronal cells within the central nervous system. T-type calcium channels (transient opening calcium channels) are distinct from L-type calcium channels (long-lasting calcium channels) due to their ability to be activated by more negative membrane potentials, their small single channel conductance, and their non-responsiveness to traditional calcium channel antagonist drugs, targeting L-type calcium channels.

T-type calcium channels open following small membrane depolarizations. T-type calcium channels have been primarily studied in the context of neuronal and cardiomyocyte function, and have been implicated in hyperexcitability disorders, such as epilepsy and cardiac dysfunction. Voltage gated calcium channels are not generally expressed in non-excitable cells, but there is evidence that T-type calcium channels are expressed in cancer cells of non-excitable lineages.

T-type calcium channels are activated and inactivated by small membrane depolarizations, and display slow deactivation rates. Thus, these channels can carry depolarizing current at low membrane potentials and mediate cellular "window" currents, which occur within the voltage overlap between activation and steady state inactivation at low or resting membrane potentials. T-type calcium channels can maintain window current at non-stimulated or resting membrane potentials, thereby allowing a sustained inward calcium current carried by a portion of channels that are not inactivated. Mediation of window current allows T-type calcium channels to regulate intracellular calcium levels, both in electrically firing cells such as neurons, and in non-excitable tissues, under non-stimulated or resting cellular conditions.

Voltage-gated calcium channels are made up of several subunits. The al subunit is the primary subunit that forms the transmembrane pore of the channel. The al subunit also determines the type of calcium channel. The $\beta$, $\alpha_2\delta$, and $\gamma$ subunits, present in only some types of calcium channels, are auxiliary subunits that play secondary roles in the channel. The $\alpha_1$ subunit is composed of four domains (I-IV), with each domain containing 6 transmembrane segments (S1-S6), and hydrophobic loops between the S5 and S6 segments of each domain form the pore of the channel. Sub-types of the T-type calcium channel are defined by the specific $\alpha_1$ subunit as shown in Table 1.

TABLE 1

| T-type Calcium Channel Sub-Types | | |
|---|---|---|
| Designation | $\alpha_1$ subunit | Gene |
| Cav3.1 | $\alpha_1$G | CACNA1G |
| Cav3.2 | $\alpha_1$H | CACNA1H |
| Cav3.3 | $\alpha_1$I | CACNA1I |

T-type calcium channels have been implicated in pathologies related to a variety of diseases and disorders, including epilepsy, essential tremor, pain, neuropathic pain, schizophrenia, Parkinson's disease, depression, anxiety, sleep disorders, sleep disturbances, psychosis, schizophreniac, cardiac arrhythmia, hypertension, pain, cancer, diabetes, infertility and sexual dysfunction. *J. Neuroscience,* 1994, 14, 5485; Drugs Future, 2005, 30(6), 573-580; *EMBO J.,* 2005, 24, 315-324; *Drug Discovery Today,* 2006, 11(5-6), 245-253.

Compounds that inhibit T-type calcium channels, and uses of such compounds, are described in in Giordanetto et al, "T-type calcium channels inhibitors: a patent review," *Expert Opin. Ther. Pat.,* 2011, 21, 85-101, WO2004035000, WO9304047, WO2006098969, WO2009009015, WO2007002361, WO2007002884, WO2007120729, WO2009054982, WO2009054983, WO2009054984, US20090270413, WO2008110008, WO2009146539, WO2009146540, U.S. Pat. No. 8,133,998, WO2010083264, WO2006023881, WO2006023883, WO2005007124, WO2005009392, US2005245535, WO2007073497, WO200707852, WO2008033447, WO2008033456, WO2008033460, WO2008033464, WO2008033465, WO2008050200, WO20081 17148, WO2009056934, EP1568695, WO2008007835, KR754325, U.S. Pat. No. 7,319,098, US20100004286, EP1757590, KR2009044924, US2010094006, WO2009035307, US20090325979, KR75758317, WO2008018655, US20080293786, and US20100056545, each of which is incorporated herein by reference in its entirety.

SUMMARY

The present disclosure provides, inter alia, a compound of Formula I:

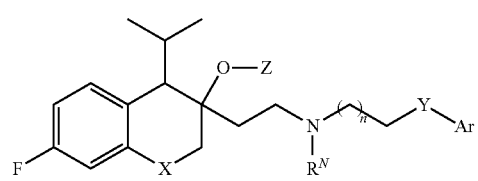

or a pharmaceutically acceptable salt thereof; wherein the variables are as defined below.

The present disclosure also provides a composition comprising a compound of Formula I, or a pharmaceutically acceptable salt thereof, and at least one pharmaceutically acceptable carrier.

The present disclosure also provides methods of treating cancer comprising administering to a patient a therapeutically effective amount of a compound of Formula I, or a pharmaceutically acceptable salt thereof.

The details of one or more embodiments are set forth in the description below. Other features, objects and advantages will be apparent from the description and from the claims.

DETAILED DESCRIPTION

It is appreciated that certain features described herein, which are, for clarity, described in the context of separate embodiments, can also be provided in combination in a single embodiment. Conversely, various features of the disclosure which are, for brevity, described in the context of a single embodiment, can also be provided separately or in any suitable sub-combination.

I. DEFINITIONS

Unless defined otherwise, all technical and scientific terms used herein have the same meaning as is commonly understood by one of ordinary skill in the art to which this disclosure belongs, taking into account the context provided by the present disclosure.

For the terms "e.g." and "such as," and grammatical equivalents thereof, the phrase "and without limitation" is understood to follow unless explicitly stated otherwise.

The singular forms "a," "an," and "the" include plural referents unless the context clearly dictates otherwise.

The term "about" means "approximately" (e.g., plus or minus approximately 10% of the indicated value).

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group. When the term is used to refer to a carbocyclic ring (e.g., aryl or cycloalkyl), all of the ring atoms are carbon atoms. When the term is used to refer to a heterocyclic ring (e.g., heteroaryl or heterocycloalkyl), one or more of the ring atoms (e.g., 1, 2, 3, or 4) are heteroatoms (e.g., nitrogen, oxygen or sulfur) and the remainder (e.g., n-1, n-2, n-3, or n-4) are carbon atoms.

At various places in the present specification, divalent linking substituents are described. It is specifically intended that each divalent linking substituent include both the forward and backward forms of the linking substituent. For example, —NR(CR$^1$R")$_n$—includes both —NR(CR$^1$R")$_n$— and —(CR$^1$R")$_n$NR—. Where the structure clearly requires a linking group, the Markush variables listed for that group are understood to be linking groups.

The phrase "optionally substituted" means unsubstituted or substituted. The substituents are independently selected, and substitution may be at any chemically accessible position. The term "substituted" means that a hydrogen atom is removed and replaced by a substituent. A single divalent substituent, e.g., oxo, can replace two hydrogen atoms. It is to be understood that substitution at a given atom is limited by valency. Example substituents include, but are not limited to, halo, $C_{1-6}$ alkyl, $C_{2-6}$ alkenyl, $C_{2-6}$ alkynyl, $C_{1-6}$ haloalkyl, $C_{1-6}$ alkoxy, OH, CN, NO$_2$, amino, $C_{1-6}$ alkylamino, di($C_{1-6}$ alkyl)amino, oxo, $C_{3-10}$ cycloalkyl, $C_{6-10}$ aryl, 4-10 membered heterocycloalkyl, and 5-10 membered heteroaryl.

In some embodiments, the $C_{3-10}$ cycloalkyl, $C_{6-10}$ aryl, 4-10 membered heterocycloalkyl, and 5-10 membered heteroaryl forming a substituent can be optionally substituted, e.g., by 1, 2, 3, 4, or 5 substituents each independently selected from halo, $C_{1-6}$ alkyl, $C_{2-6}$ alkenyl, $C_{2-6}$ alkynyl, $C_{1-6}$ haloalkyl, $C_{1-6}$ alkoxy, OH, CN, NO$_2$, amino, $C_{1-6}$ alkylamino, di($C_{1-6}$ alkyl)amino and oxo.

The term "$C_{n-m}$" indicates a range which includes the endpoints, wherein n and m are integers and indicate the number of carbon atoms present in a chemical group. Examples include $C_{1-2}$, $C_{1-4}$, and the like. Whenever the term is used intended to describe each member included in the group, $C_n$ through $C_m$ as if each had been explicitly set forth. For example, the term $C_{1-6}$ is intended to describe each of the members $C_1$, $C_2$, $C_3$, $C_4$, $C_5$ and $C_6$.

The term "$C_{n-m}$ alkyl" refers to a saturated hydrocarbon group that may be straight-chain or branched, having n to m carbons. The term "alkyl" refers to a saturated hydrocarbon group that may be straight-chain or branched, and can include $C_{n-m}$ alkyl. Examples of alkyl moieties include, but are not limited to, chemical groups such as methyl, ethyl, n-propyl, isopropyl, n-butyl, tert-butyl, isobutyl, sec-butyl, and the like. In some embodiments, the alkyl group contains from 1 to 4 carbon atoms, from 1 to 3 carbon atoms, or 1 to 2 carbon atoms.

The term "$C_{n-m}$ alkoxy" refers to a group of formula —O-alkyl, wherein the alkyl group has n to m carbons. The term "alkoxy" refers to —O-alkyl, and can include $C_{n-m}$ alkoxy. Example alkoxy groups include, but are not limited to, methoxy, ethoxy, propoxy (e.g., n-propoxy and isopropoxy), butoxy (e.g., n-butoxy and tert-butoxy), and the like. In some embodiments, the alkyl group has 1 to 4 carbon atoms, 1 to 3 carbon atoms, or 1 to 2 carbon atoms.

The term "amino" refers to a group of formula —NH$_2$.

The term "$C_{n-m}$ alkylamino" refers to a group of formula —NH(alkyl), wherein the alkyl group has n to m carbon atoms. In some embodiments, the alkyl group has 1 to 4 carbon atoms, 1 to 3 carbon atoms, or 1 to 2 carbon atoms. Examples of alkylamino groups include, but are not limited to, N-methylamino, N-ethylamino, N-propylamino (e.g., N-(n-propyl)amino and N-isopropylamino), N-butylamino (e.g., N-(n-butyl)amino and N-(tert-butyl)amino), and the like.

The term "di($C_{n-m}$-alkyl)amino" refers to a group of formula —N(alkyl)$_2$, wherein the two alkyl groups each has, independently, n to m carbon atoms. In some embodiments, each alkyl group independently has 1 to 4 carbon atoms, 1 to 3 carbon atoms, or 1 to 2 carbon atoms. Example dialkylamino groups include, but are not limited to, dimethylamino, ethylmethylamino, diethylamino, methylpropylamino, ethylpropylamino, dipropylamino, dibutylamino, butylpropylamino, and the like.

The term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, but are not limited to, phenyl, naphthyl, anthracenyl, phenanthrenyl, indanyl, indenyl, and the like. In some embodiments, aryl groups have from 6 to about 20 carbon atoms, from 6 to about 15 carbon atoms, or from 6 to about 10 carbon atoms. In some embodiments, the aryl group is an optionally substituted phenyl. In some embodiments, the aryl group is an unsubstituted phenyl. In some embodiments, the aryl group is an optionally substituted naphthyl. In some embodiments, the aryl group is an unsubstituted naphthyl.

"Halo" or "halogen" refers to F, Cl, Br, or I. In some embodiments, a halo is F or Cl. In some embodiments, a halo is Cl.

The term "haloalkyl" refers to an alkyl group substituted by one or more halogen atoms, and can include "$C_{n-m}$ haloalkyl". The term "$C_{n-m}$ haloalkyl", refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 4 carbon atoms, 1 to 3 carbon atoms, or 1 to 2 carbon atoms. The number of halogen atoms(s) can be, e.g., 1, 2 or 3. In some embodiments, a haloalkyl group is trifluoromethyl (—$CF_3$).

"Cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups and spirocycles. Cycloalkyl groups can have 3, 4, 5, or 6 ring-forming carbons (e.g., a $C_{3-6}$ cycloalkyl group). In some embodiments, the cycloalkyl is a $C_{3-6}$ monocyclic cycloalkyl. Example cycloalkyl groups include cyclopropyl, cyclobutyl, cyclopentyl, cyclohexyl and the like.

"Heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur and oxygen. In some embodiments, the heteroaryl is a 5-10 membered monocyclic or bicyclic heteroaryl having 1, 2, 3, 4, 5, 6, 7, 8 or 9 carbon atom ring members and 1, 2, 3 or 4 heteroatom ring members independently selected from nitrogen, sulfur and oxygen. In some embodiments, the heteroaryl is an 8-10 membered bicyclic fused heteroaryl having 4, 5, 6, 7, 8 or 9 carbon atom ring members and 1, 2, 3 or 4 heteroatom ring members independently selected from nitrogen, sulfur and oxygen. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. Exemplary six-membered ring heteroaryls are pyridyl, pyrazinyl, pyrimidinyl, triazinyl and pyridazinyl. Exemplary nine-membered ring heteroaryl are 1H-benzo[d]imidazole, 1H-benzo[d][1,2,3]triazole, 3H-imidazo[4,5-b]pyridine, 1H-imidazo[4,5-b]pyrazine, and the like.

"Heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, 7-, 8-, 9- or 10-membered heterocycloalkyl groups. Heterocycloalkyl groups can also include spirocycles. Example heterocycloalkyl groups include pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by oxo or sulfido (e.g., C(O), S(O), C(S), or S(O)$_2$, etc.). The heterocycloalkyl group can be attached through a ring-forming carbon atom or a ring-forming heteroatom (e.g. a ring-forming nitrogen atom). In some embodiments, the heterocycloalkyl is a monocyclic 4-6 membered heterocycloalkyl having 1, 2, 3, 4, or 5 carbon atom ring members and 1 or 2 heteroatoms independently selected from nitrogen, oxygen, or sulfur.

At certain places, the definitions or embodiments refer to specific rings (e.g., a pyrrolidine ring, etc.). Unless otherwise indicated, these rings can be attached to any ring member provided that the valency of the atom is not exceeded. For example, an pyrrolidinyl ring may be attached at any position of the ring, whereas a pyrrolidin-1-yl ring is attached at the 1-position.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. In some embodiments, the compound has an (R)-configuration. In some embodiments, the compound has an (S)-configuration. In some embodiments, the compound has an (R,R)-configuration. In some embodiments, the compound has an (R,S)-configuration. In some embodiments, the compound has an (S,S)-configuration. In some embodiments, the compound has an (S,R)-configuration.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as (3-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H— and 3H-imidazole, 1H—, 2H— and 4H-1,2,4-triazole, 1H- and 2H-isoindole, and 1H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

Example acids can be inorganic or organic acids and include, but are not limited to, strong and weak acids. Example acids include, but are not limited to, hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, nitric acid, acetic acid, propionic acid, butanoic acid, benzoic acid, tartaric acid, pentanoic acid, hexanoic acid, heptanoic acid, octanoic acid, nonanoic acid, and decanoic acid.

Example bases include, but are not limited to, hydroxide, alkoxides, metal amides, metal hydrides, metal dialkylamides, and arylamines, wherein: hydroxides include lithium, sodium, and potassium hydroxides; alkoxides include lithium, sodium, and potassium salts of methyl, ethyl and t-butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, iso-propyl, n-butyl, tert-butyl, trimethylsilyl and cyclohexyl substituted amides.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The term "compound" includes all stereoisomers, geometric isomers, tautomers, and isotopes of the structures depicted, unless the context indicates otherwise. Compounds herein identified by name or structure as one particular tautomeric form are intended to include other tautomeric forms unless otherwise specified.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. The present invention also includes pharmaceutically acceptable salts of the compounds described herein. The term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic acid salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

The expressions, "ambient temperature" (abbreviated "rt") and "room temperature" refer generally to a temperature, e.g., a reaction temperature, that is about the temperature of the room in which the reaction is carried out, e.g., a temperature from about 20° C. to about 30° C., typically about 25° C.

A "cellular proliferative disorder" means a disorder wherein cells are made by the body at an atypically accelerated rate.

The term "contacting" means bringing at least two moieties together, whether in an in vitro system or an in vivo system.

The terms "individual" or "patient," used interchangeably, refer to (e.g., as a subject of the treatment) any animal, including mammals, preferably mice, rats, other rodents, rabbits, dogs, cats, swine, cattle, sheep, horses, or primates, and most preferably humans.

The phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

The term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease. In one embodiment, treating or treatment includes preventing or reducing the risk of developing the disease; e.g., preventing or reducing the risk of developing a disease, condition or disorder in an individual who may be predisposed to the disease, condition or disorder but does not yet experience or display the pathology or symptomatology of the disease.

The following abbreviations may be used herein: AcOH (acetic acid); aq. (aqueous); br (broad); d (doublet); dd (doublet of doublets); DCM (dichloromethane); DIAD (N,N'-diisopropyl azidodicarboxylate); DIC (N,N'-diisopropylcarbodiimide); DIPEA (N,N-diisopropylethylamine); DMAP (4-dimethylaminopyridine); DMF (N,N-dimethylformamide); eq. (equivalent(s)); Et (ethyl); EtOAc (ethyl acetate); g (gram(s)); h (hour(s)); HATU (N,N,N',N'-tetramethyl-O-(7-azabenzotriazol-1-yl)uronium hexafluorophosphate); HCl (hydrochloric acid); HPLC (high performance liquid chromatography); Hz (hertz); J (coupling constant); LCMS (liquid chromatography mass spectrometry); m (multiplet); m (molar); MS (Mass spectrometry); Me (methyl);

MeCN (acetonitrile); MeOH (methanol); mg (milligram(s)); min. (minutes(s)); mL (milliliter(s)); mmol (millimole(s)); N (normal); NaHCO$_3$ (sodium bicarbonate); NaOH (sodium hydroxide); Na$_2$SO$_4$ (sodium sulfate); NH$_4$Cl (ammonium chloride); nm (nanometer); nM (nanomolar); NMR (nuclear magnetic resonance spectroscopy); PPTS (pyridinium p-toluenesulfonate); RP-HPLC (reverse phase high performance liquid chromatography); rt (room temperature); s (singlet); t (triplet or tertiary); tert (tertiary); tt (triplet of triplets); t-Bu (tert-butyl); THF (tetrahydrofuran); μg (microgram(s)); μL (microliter(s)); μM (micromolar); wt % (weight percent).

II. COMPOUNDS

The present application provides, inter alia, a compound of Formula I:

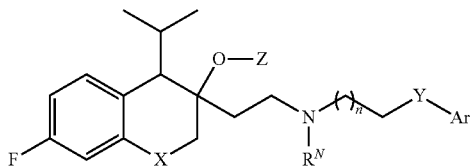

or a pharmaceutically acceptable salt thereof, wherein:

X is O or CH$_2$;
Y is CR$^1$R$^2$, NR$^3$, C(=O), C(=O)NH, or NH(C=O);
Z is C(=O)OR$^{Z1}$, or C(=O)NR$^{Z2}$R$^{Z3}$;
n is 0, 1, 2, or 3;
R$^N$ is H or an optionally substituted C$_{1-4}$ alkyl;
R$^1$ is H or an optionally substituted C$_{1-4}$ alkyl;
R$^2$ is H or an optionally substituted C$_{1-4}$ alkyl; or
R$^1$ and R$^2$ in combination form a C$_{2-4}$ alkylene group which, together with the carbon atom to they are attached, form a 3-6-membered optionally substituted cycloalkyl ring;
R$^3$ is H or an optionally substituted C$_{1-4}$ alkyl;
R$^{Z1}$ is an optionally substituted C$_{1-4}$ alkyl;
R$^{Z2}$ is H or an optionally substituted C$_{1-4}$ alkyl;
R$^{Z3}$ is H or an optionally substituted C$_{1-4}$ alkyl; or
R$^{Z2}$ and R$^{Z3}$ in combination with the nitrogen atom to which they are attached form an optionally substituted 4-6 membered heterocycloalkyl ring; and
Ar is optionally substituted C$_{6-10}$ aryl, or a 5-10 membered optionally substituted heteroaryl.

In some embodiments, each substituted C$_{1-4}$ alkyl is substituted by 1, 2, 3, 4 or 5 substituents, each independently selected from halo, C$_{1-4}$ alkyl, C$_{2-4}$ alkenyl, C$_{2-4}$ alkynyl, C$_{1-4}$ haloalkyl, C$_{1-4}$ alkoxy, OH, CN, NO$_2$, amino, C$_{1-4}$ alkylamino, di(C$_{1-4}$ alkyl)amino, oxo, optionally substituted C$_{3-10}$ cycloalkyl, optionally substituted C$_{6-10}$ aryl, optionally substituted 4-10 membered heterocycloalkyl, and optionally substituted 5-10 membered heteroaryl;

each substituted cycloalkyl and heterocycloalkyl is substituted by 1, 2, 3, 4 or 5 substituents, each independently selected from halo, C$_{1-4}$ alkyl, C$_{2-4}$ alkenyl, C$_{2-4}$ alkynyl, C$_{1-4}$ haloalkyl, C$_{1-4}$ alkoxy, OH, CN, NO$_2$, amino, C$_{1-4}$ alkylamino, di(C$_{1-4}$ alkyl)amino and oxo; and each substituted aryl and heteroaryl is substituted by 1, 2, 3, 4, or 5 substituents, each independently selected from halo, C$_{1-4}$ alkyl, C$_{2-4}$ alkenyl, C$_{2-4}$ alkynyl, C$_{1-4}$ haloalkyl, C$_{1-4}$ alkoxy, OH, CN, NO$_2$, amino, C$_{1-4}$ alkylamino, and di(C$_{1-4}$ alkyl) amino.

In some embodiments, X is O.
In some embodiments, X is CH$_2$.
In some embodiments, Y is CR$^1$R$^2$.
In some embodiments, Y is NR$^3$, C(=O), C(=O)NH, or NH(C=O).
In some embodiments, R$^3$ is H or an unsubstituted C$_{1-4}$ alkyl, e.g., methyl or ethyl.
In some embodiments, R$^3$ is H.
In some embodiments, R$^N$ is H or an unsubstituted C$_{1-4}$ alkyl.
In some embodiments, R$^N$ is an unsubstituted C$_{1-4}$ alkyl.
In some embodiments, R$^N$ is methyl or ethyl.
In some embodiments, R$^1$ is H or unsubstituted C$_{1-4}$ alkyl, e.g., methyl or ethyl.
In some embodiments, R$^1$ is H or methyl.
In some embodiments, R$^2$ is H or unsubstituted C$_{1-4}$ alkyl, e.g., methyl or ethyl.
In some embodiments, R$^2$ is H or methyl.
In some embodiments, R$^1$ is H or an optionally substituted C$_{1-4}$ alkyl, e.g., methyl or ethyl, and R$^2$ is H or an optionally substituted C$_{1-4}$ alkyl, e.g., methyl or ethyl.
In some embodiments, R$^1$ and R$^2$ are each H.
In some embodiments, R$^1$ and R$^2$ are each unsubstituted C$_{1-4}$ alkyl, e.g., methyl or ethyl.
In some embodiments, R$^1$ and R$^2$ are each methyl.
In some embodiments, R$^1$ and R$^2$ in combination form a C$_{2-4}$ alkylene group (e.g., a —CH$_2$)$_{2-4}$— group) which, together with the carbon atom to they are attached, form a 3-6-membered optionally substituted cycloalkyl ring.
In some embodiments, R$^1$ and R$^2$ in combination form a C$_{2-4}$ alkylene group which, together with the carbon atom to they are attached, form a 3-6-membered unsubstituted cycloalkyl ring, such as cyclopropyl, cyclobutyl, cyclopentyl or cyclohexyl. In some embodiments, the cycloalkyl ring can be unsubstituted. In some embodiments, the cycloalkyl ring can be substituted.
In some embodiments, R$^1$ and R$^2$ in combination form an ethylene group which, together with the carbon atom to they are attached, form an unsubstituted cyclopropyl ring.
In some embodiments, n is 0.
In some embodiments, n is 1.
In some embodiments, n is 2.
In some embodiments, n is 3.
In some embodiments, Z is C(=O)OR$^{Z1}$.
In some embodiments, R$^{Z1}$ is an unsubstituted C$_{1-4}$ alkyl e.g., methyl or ethyl.
In some embodiments, R$^{Z1}$ is methyl.
In some embodiments, Z is C(=O)NR$^{Z2}$R$^{Z3}$.
In some embodiments, R$^{Z2}$ is H or an unsubstituted C$_{1-4}$ alkyl e.g., methyl or ethyl.
In some embodiments, R$^{Z2}$ is H or methyl.
In some embodiments, R$^{Z3}$ is an optionally substituted C$_{1-4}$ alkyl e.g., methyl or ethyl.
In some embodiments, R$^{Z3}$ is a C$_{1-4}$ alkyl which is optionally substituted by 1, 2, or 3 groups independently selected from amino, C$_{1-4}$ alkylamino, di(C$_{1-4}$ alkyl)amino, C$_{1-4}$ alkoxy, and 4-6 membered heterocycloalkyl.
In some embodiments, R$^{Z3}$ is methyl, N,N-dimethylaminoethyl, N,N-diethylaminoethyl, methoxyethyl, or pyrrolidinylethyl.
In some embodiments, R$^{Z3}$ is methyl, 2-(N,N-dimethylamino)ethyl, 2-(N,N-diethylamino)ethyl, 2-methoxyethyl, or 2-(pyrrolidin-1-yl)ethyl.
In some embodiments, R$^{Z2}$ is H or an optionally substituted C$_{1-4}$ alkyl and R$^{Z3}$ is H or an optionally substituted C$_{1-4}$ alkyl.

In some embodiments, $R^{Z2}$ is H or an unsubstituted $C_{1-4}$ alkyl, e.g., methyl or ethyl, and $R^{Z3}$ is an optionally substituted $C_{1-4}$ alkyl, e.g., methyl or ethyl.

In some embodiments, $R^{Z2}$ and $R^{Z3}$ in combination with the nitrogen atom to which they are attached form an optionally substituted 4-6 membered heterocycloalkyl ring.

In some embodiments, $R^{Z2}$ and $R^{Z3}$ in combination with the nitrogen atom to which they are attached form an unsubstituted 4-6 membered heterocycloalkyl ring.

In some embodiments, $R^{Z2}$ and $R^{Z3}$ in combination with the nitrogen atom to which they are attached form a morpholinyl ring.

In some embodiments, Ar is optionally substituted phenyl, optionally substituted naphthyl, or a 5-10 membered optionally substituted heteroaryl.

In some embodiments, Ar is an aryl (e.g., phenyl), naphthyl, or a 5-10 membered heteroaryl, each of which is optionally substituted by 1, 2, 3, or 4 independently selected $R^{Ar}$ groups, wherein each $R^{Ar}$ is independently selected from the group consisting of halo, $C_{1-4}$ alkyl, $C_{1-4}$ haloalkyl, and $C_{1-4}$ alkoxy.

In some embodiments, Ar is unsubstituted phenyl, unsubstituted naphthyl, or a 5-10 membered optionally substituted heteroaryl.

In some embodiments, Ar is a 5-10 membered optionally substituted heteroaryl.

In some embodiments, Ar is an 8-10 membered optionally substituted heteroaryl. In some embodiments, the 8-10 membered optionally substituted heteroaryl is an 8-10 membered fused bicyclic heteroaryl.

In some embodiments, Ar is a 5-10 membered heteroaryl optionally substituted by 1, 2, 3, or 4 groups independently selected from halo, $C_{1-4}$ alkyl, $C_{1-4}$ haloalkyl, and $C_{1-4}$ alkoxy.

In some embodiments, Ar is an 8-10 membered heteroaryl optionally substituted by 1, 2, 3, or 4 groups independently selected from halo, $C_{1-4}$ alkyl, $C_{1-4}$ haloalkyl, and $C_{1-4}$ alkoxy.

In some embodiments, Ar is a 5-10 membered heteroaryl optionally substituted by 1, 2, 3, or 4 groups independently selected from chloro, methyl, methoxy, and trifluoromethyl.

In some embodiments, Ar is an 8-10 membered heteroaryl optionally substituted by 1, 2, 3, or 4 groups independently selected from chloro, methyl, methoxy, and trifluoromethyl.

In some embodiments, Ar a group of formula Ar-1:

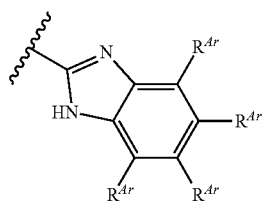

Ar-1 wherein each $R^{Ar}$ is independently selected from the group consisting of h, halo, $C_{1-4}$ alkyl, $C_{1-4}$ haloalkyl, and $C_{1-4}$ alkoxy.

In some embodiments, each $R^{Ar}$ is independently selected from the group consisting of h, chloro, methyl, methoxy, and trifluoromethyl.

In some embodiments, Ar is a group selected from formula Ar-2 and Ar-3:

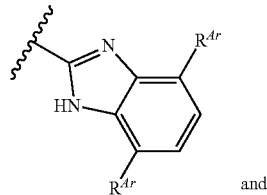

Ar-2 and

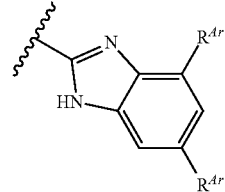

Ar-3 wherein each $R^{Ar}$ is independently selected from the group consisting of halo, $C_{1-4}$ alkyl, $C_{1-4}$ haloalkyl, and $C_{1-4}$ alkoxy.

In some embodiments, each $R^{Ar}$ is independently selected from the group consisting of chloro, methyl, methoxy, and trifluoromethyl.

In some embodiments, Ar is:

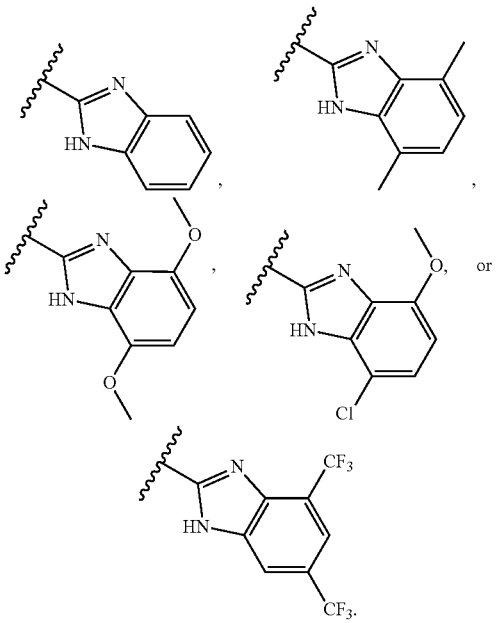

In some embodiments:

X is O or $CH_2$;

Y is $CR^1R^2$;

Z is $C(=O)OR^{Z1}$, or $C(=O)NR^{Z2}R^{Z3}$;

$R^N$ is an unsubstituted $C_{1-4}$ alkyl;

$R^1$ is H or unsubstituted $C_{1-4}$ alkyl;

$R^2$ is H or unsubstituted $C_{1-4}$ alkyl; or $R^1$ and $R^2$ in combination form a $C_{2-4}$ alkylene group which, together with the carbon atom to they are attached, form a 3-6-membered optionally substituted cycloalkyl ring;

n is 0, 1, 2, or 3;

$R^{Z1}$ is an unsubstituted $C_{1-4}$ alkyl;

$R^{Z2}$ is H or an unsubstituted $C_{1-4}$ alkyl;

$R^{Z3}$ is an optionally substituted $C_{1-4}$ alkyl; or $R^{Z2}$ and $R^{Z3}$ in combination with the nitrogen atom to which they are attached form an optionally substituted 4-6 membered heterocycloalkyl ring; and Ar is optionally substituted phenyl, optionally substituted naphthyl, or a 5-10 membered optionally substituted heteroaryl.

In some embodiments:

X is O or $CH_2$;

Y is $CR^1R^2$;

Z is $C(=O)OR^{Z1}$, or $C(=O)NR^{Z2}R^{Z3}$;

$R^N$ is an unsubstituted $C_{1-4}$ alkyl e.g., methyl or ethyl;

$R^1$ is H or unsubstituted $C_{1-4}$ alkyl e.g., methyl or ethyl;

$R^2$ is H or unsubstituted $C_{1-4}$ alkyl e.g., methyl or ethyl; or $R^1$ and $R^2$ in combination form a $C_{2-4}$ alkylene group which, together with the carbon atom to they are attached, form a 3-6-membered optionally substituted cycloalkyl ring;

n is 1;

$R^{Z1}$ is an unsubstituted $C_{1-4}$ alkyl e.g., methyl or ethyl;

$R^{Z2}$ is H or an unsubstituted $C_{1-4}$ alkyl e.g., methyl or ethyl;

$R^{Z3}$ is a $C_{1-4}$ alkyl which is optionally substituted by 1, 2, or 3 groups independently selected from amino, $C_{1-4}$ alkylamino, di($C_{1-4}$ alkyl)amino, $C_{1-4}$ alkoxy, and 4-6 membered heterocycloalkyl $R^{Z2}$ and $R^{Z3}$ in combination with the nitrogen atom to which they are attached form an optionally substituted 4-6 membered heterocycloalkyl ring; and Ar is a 5-10 membered optionally substituted heteroaryl.

In some embodiments:

X is O or $CH_2$;

Y is $CR^1R^2$;

Z is $C(=O)OR^{Z1}$, or $C(=O)NR^{Z2}R^{Z3}$;

$R^N$ is an unsubstituted $C_{1-4}$ alkyl e.g., methyl or ethyl;

$R^1$ is H or methyl;

$R^2$ is H or methyl; or $R^1$ and $R^2$ in combination form an ethylene group which, together with the carbon atom to they are attached, form a cyclopropyl ring;

n is 1;

$R^{Z1}$ is an unsubstituted $C_{1-4}$ alkyl e.g., methyl or ethyl;

$R^{Z2}$ is H or an unsubstituted $C_{1-4}$ alkyl e.g., methyl or ethyl;

$R^{Z3}$ is a $C_{1-4}$ alkyl which is optionally substituted by 1, 2, or 3 groups independently selected from amino, $C_{1-4}$ alkylamino, di($C_{1-4}$ alkyl)amino, $C_{1-4}$ alkoxy, and 4-6 membered heterocycloalkyl $R^{Z2}$ and $R^{Z3}$ in combination with the nitrogen atom to which they are attached form an optionally substituted 4-6 membered heterocycloalkyl ring; and Ar is a 5-10 membered heteroaryl optionally substituted by 1, 2, 3, or 4 groups independently selected from halo, $C_{1-4}$ alkyl, $C_{1-4}$ haloalkyl, and $C_{1-4}$ alkoxy.

In some embodiments, the compound of Formula I is a compound of Formula II:

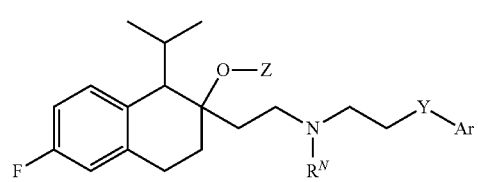

or a pharmaceutically acceptable salt thereof, wherein variables Y, Z, $R^N$, and Ar are defined according to the definitions provided herein for compounds of Formula I.

In some embodiments, the compound of Formula I is a compound of Formula III:

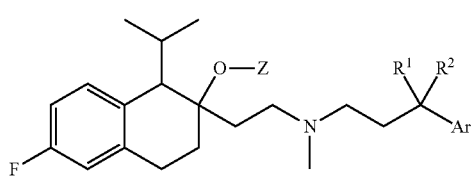

or a pharmaceutically acceptable salt thereof, wherein variables Z, $R^1$, $R^2$, and Ar are defined according to the definitions provided herein for compounds of Formula I.

In some embodiments, the compound of Formula I is a compound of Formula IV:

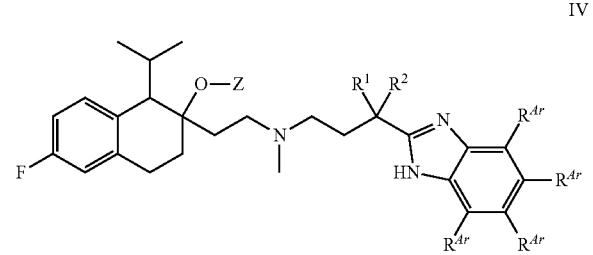

or a pharmaceutically acceptable salt thereof, wherein variables Z, $R^1$, and $R^2$ are defined according to the definitions provided herein for compounds of Formula I; and each $R^{Ar}$ is independently selected from H, halo, $C_{1-4}$ alkyl, $C_{1-4}$ haloalkyl, and $C_{1-4}$ alkoxy.

In some embodiments, the compound of Formula I is a compound of Formula V:

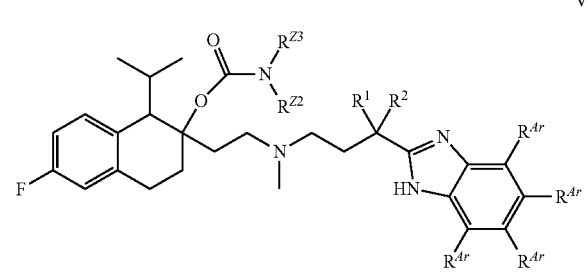

or a pharmaceutically acceptable salt thereof, wherein variables $R^{Z2}$, $R^{Z3}$, $R^1$, and $R^2$ are defined according to the definitions provided herein for compounds of Formula I; and each $R^{Ar}$ is independently selected from H, halo, $C_{1-4}$ alkyl, $C_{1-4}$ haloalkyl, and $C_{1-4}$ alkoxy.

In some embodiments, the compound of Formula I is a compound of Formula VI:

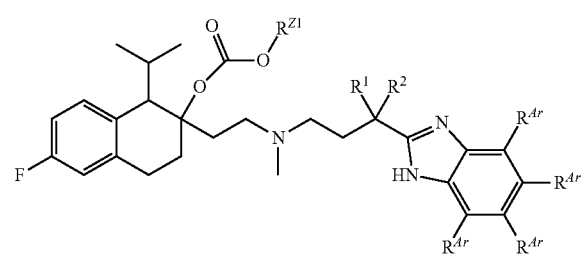

VI or a pharmaceutically acceptable salt thereof, wherein variables $R^{Z1}$, $R^1$, and $R^2$ are defined according to the definitions provided herein for compounds of Formula I; and each $R^{Ar}$ is independently selected from H, halo, $C_{1-4}$ alkyl, $C_{1-4}$ haloalkyl, and $C_{1-4}$ alkoxy.

In some embodiments, the compound of Formula I is a compound of Formula VII:

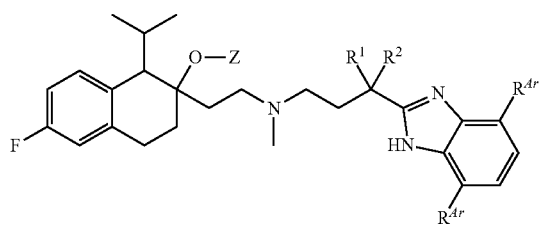

VII or a pharmaceutically acceptable salt thereof, wherein variables Z, $R^1$, and $R^2$ are defined according to the definitions provided herein for compounds of Formula I; and each $R^{Ar}$ is independently selected from halo, $C_{1-4}$ alkyl, $C_{1-4}$ haloalkyl, and $C_{1-4}$ alkoxy.

In some embodiments, the compound of Formula I is a compound of Formula VIII:

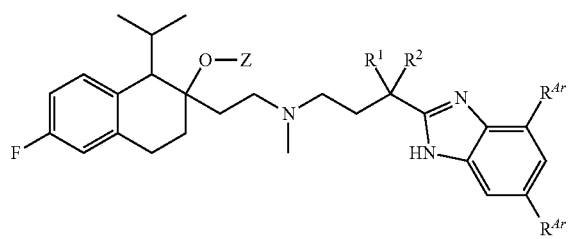

VIII or a pharmaceutically acceptable salt thereof, wherein variables Z, $R^1$, and $R^2$ are defined according to the definitions provided herein for compounds of Formula I.

each $R^{Ar}$ is independently selected from halo, $C_{1-4}$ alkyl, $C_{1-4}$ haloalkyl, and $C_{1-4}$ alkoxy.

In some embodiments, the compound of Formula I is a compound of Formula IX:

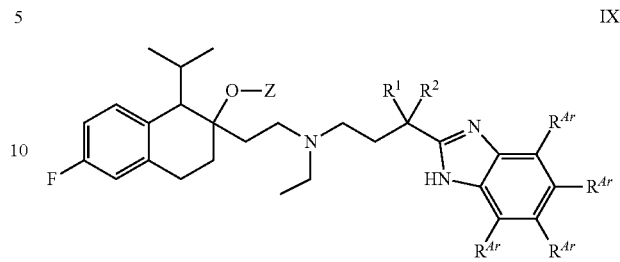

IX or a pharmaceutically acceptable salt thereof, wherein variables Z, $R^1$, and $R^2$ are defined according to the definitions provided herein for compounds of Formula I; and each $R^{Ar}$ is independently selected from halo, $C_{1-4}$ alkyl, $C_{1-4}$ haloalkyl, and $C_{1-4}$ alkoxy.

In some embodiments, the compound of Formula I is a compound of Formula X:

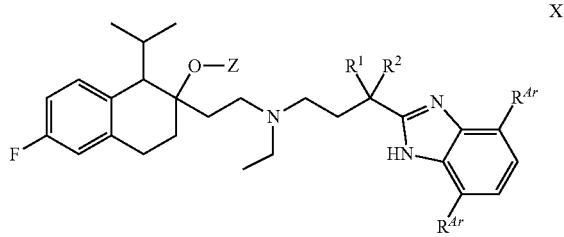

X or a pharmaceutically acceptable salt thereof, wherein variables Z, $R^1$, and $R^2$ are defined according to the definitions provided herein for compounds of Formula I; and each $R^{Ar}$ is independently selected from halo, $C_{1-4}$ alkyl, $C_{1-4}$ haloalkyl, and $C_{1-4}$ alkoxy.

In some embodiments, the compound of Formula I is a compound of Formula XI:

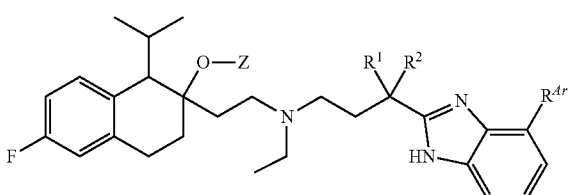

XI or a pharmaceutically acceptable salt thereof, wherein variables Z, IV, and $R^2$ are defined according to the definitions provided herein for compounds of Formula I; and each $R^{Ar}$ is independently selected from halo, $C_{1-4}$ alkyl, $C_{1-4}$ haloalkyl, and $C_{1-4}$ alkoxy.

In some embodiments, the compound of Formula I is a compound of Formula I-a, I-b, I-c II-a, II-b, II-c, III-a, III-b, III-c, IV-a, IV-b, IV-c, V-a, V-b, V-c, VI-a, VI-b, VI-c, VII-a, VII-b, VII-c, VIII-a, VIII-b, VIII-c, IX-a, IX-b, IX-c, X-a, X-b, X-c, XI-a, XI-b, or XI-c:

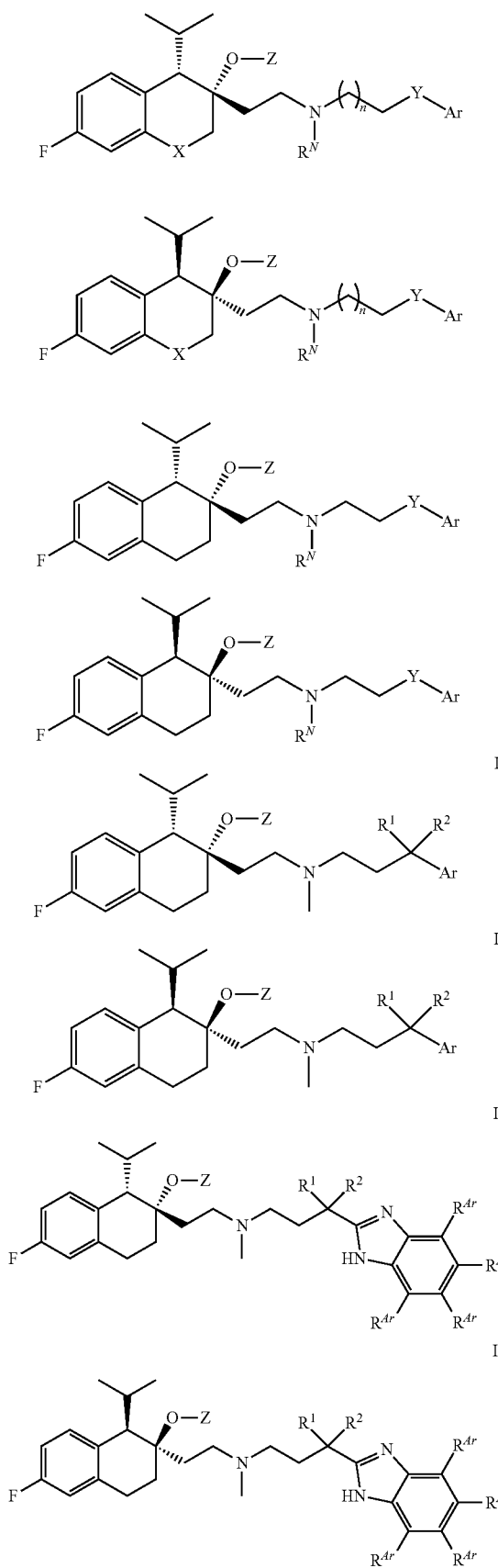
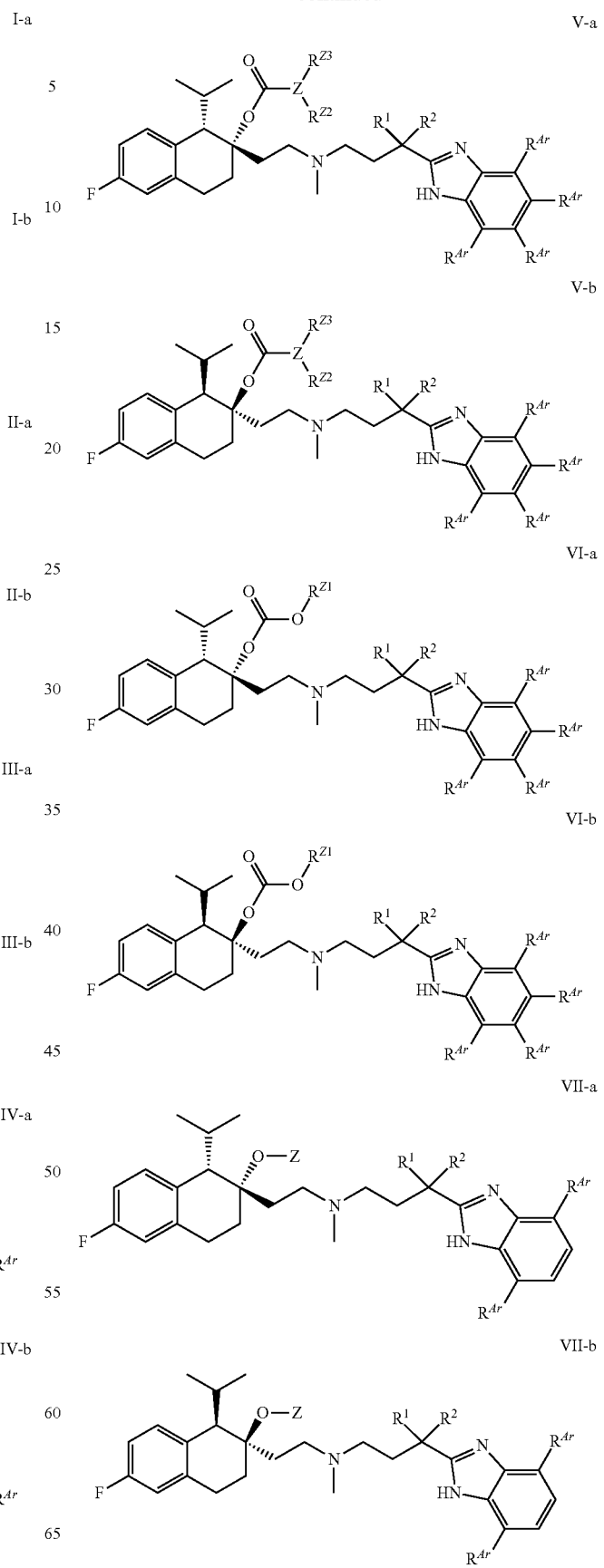

VIII-a
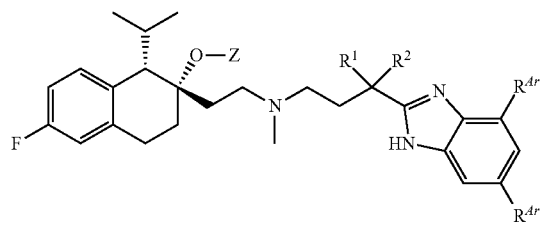
VIII-b
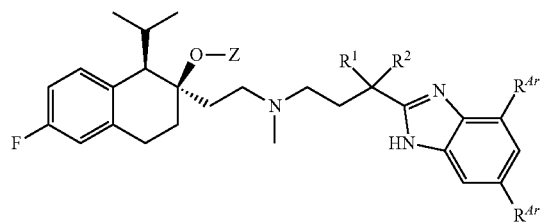
IX-a
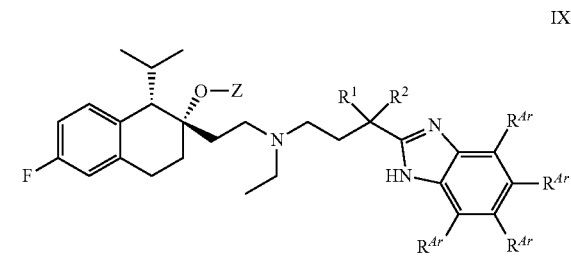
IX-b
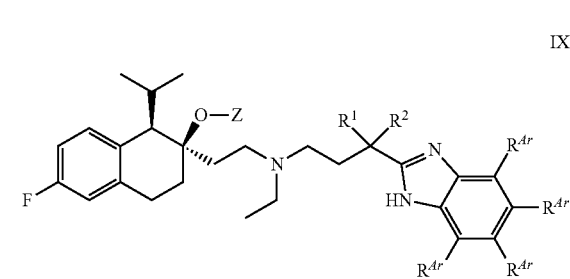
X-a
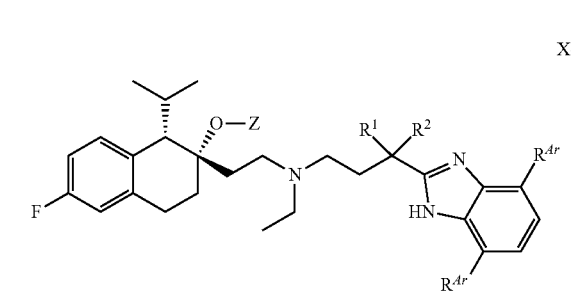
X-b
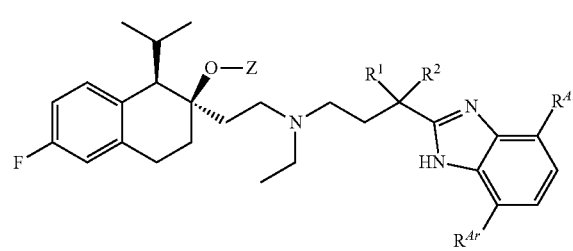
XI-a
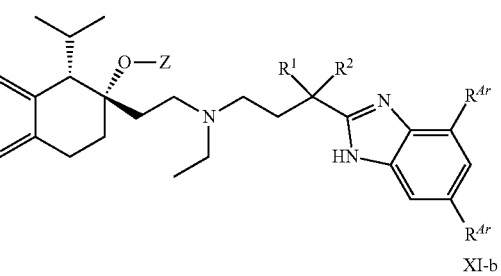
XI-b
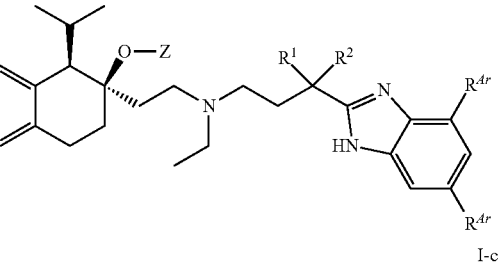
I-c
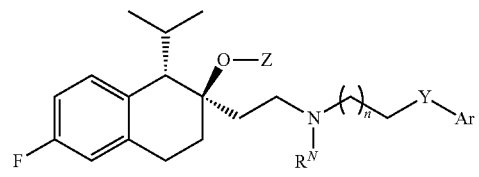
II-c
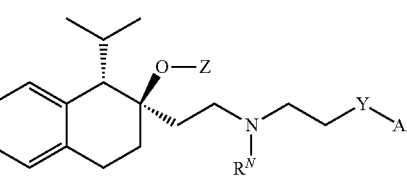
III-c
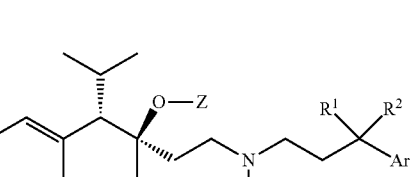
IV-c
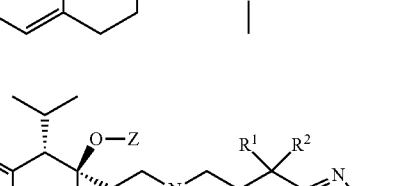
V-c
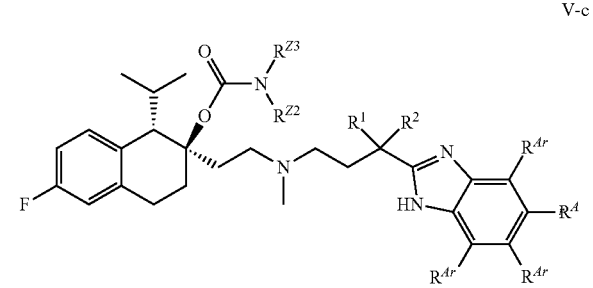

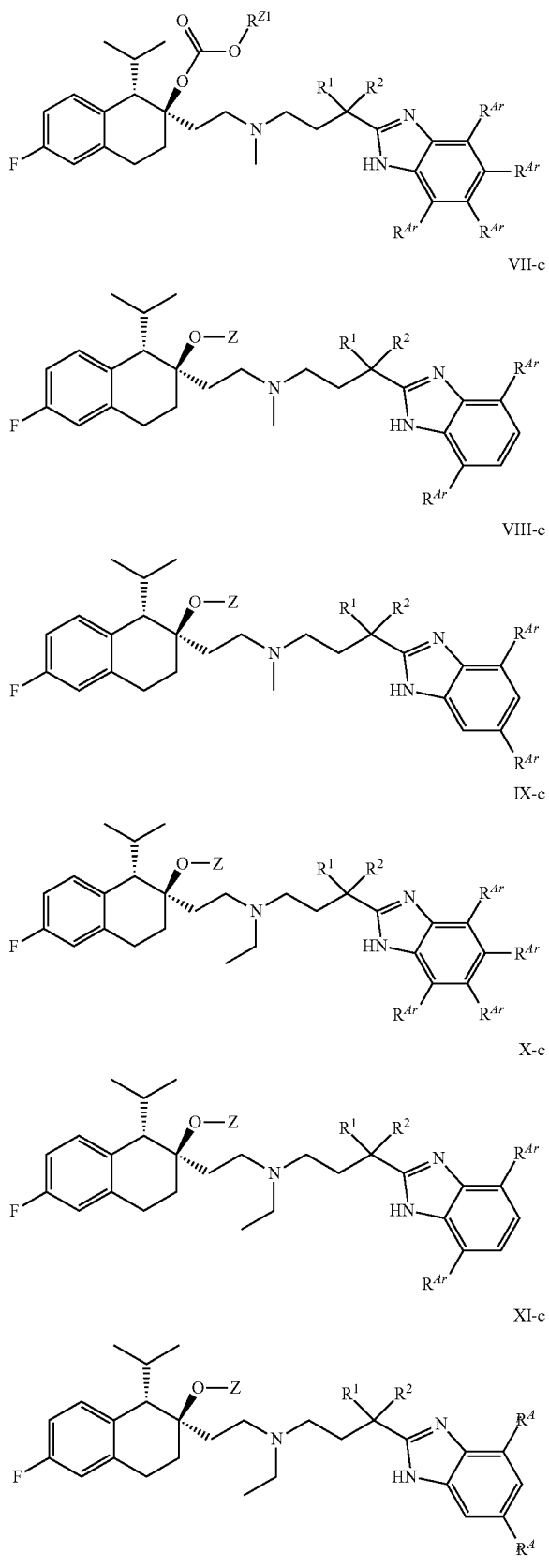

or a pharmaceutically acceptable salt thereof, wherein variables X, Y, Z, $R^N$, n, $R^1$, $R^2$, Ar, and $R^{Ar}$ are defined according to the definitions provided herein for compounds of Formula I.

In some embodiments, the compound of Formula I, or a pharmaceutically acceptable salt thereof, is selected from:

2-(2-((3-(1H-benzo[d]imidazol-2-yl)propyl)(methyl)amino)ethyl)-6-fluoro-1-isopropyl-1,2,3,4-tetrahydronaphthalen-2-yl methylcarbamate;

2-(2-((3-(1H-benzo[d]imidazol-2-yl)propyl)(methyl)amino)ethyl)-6-fluoro-1-isopropyl-1,2,3,4-tetrahydronaphthalen-2-yl methylcarbonate;

2-(2-((3-(4,7-dimethyl-1H-benzo[d]imidazol-2-yl)propyl)(methyl)amino)ethyl)-6-fluoro-1-isopropyl-1,2,3,4-tetrahydronaphthalen-2-yl methylcarbamate 2-(2-((3-(4,7-dimethyl-1H-benzo[d]imidazol-2-yl)propyl)(methyl)amino)ethyl)-6-fluoro-1-isopropyl-1,2,3,4-tetrahydronaphthalen-2-yl (2-(dimethylamino)ethyl)carbamate;

2-(2-((3-(4,7-dimethoxy-1H-benzo[d]imidazol-2-yl)propyl)(methyl)amino)ethyl)-6-fluoro-1-isopropyl-1,2,3,4-tetrahydronaphthalen-2-yl methylcarbamate;

2-(2-((3-(4,7-dimethoxy-1H-benzo[d]imidazol-2-yl)propyl)(methyl)amino)ethyl)-6-fluoro-1-isopropyl-1,2,3,4-tetrahydronaphthalen-2-yl (2-methoxyethyl)carbamate;

2-(2-((3-(7-chloro-4-methoxy-1H-benzo[d]imidazol-2-yl)propyl)(methyl)amino)ethyl)-6-fluoro-1-isopropyl-1,2,3,4-tetrahydronaphthalen-2-yl dimethylcarbamate;

2-(2-((3-(4,6-bis(trifluoromethyl)-1H-benzo[d]imidazol-2-yl)propyl)(methyl)amino)ethyl)-6-fluoro-1-isopropyl-1,2,3,4-tetrahydronaphthalen-2-yl morpholine-4-carboxylate;

2-(2-((3-(1H-benzo[d]imidazol-2-yl)-3-methylbutyl)(methyl)amino)ethyl)-6-fluoro-1-isopropyl-1,2,3,4-tetrahydronaphthalen-2-yl morpholine-4-carboxylate;

2-(2-((3-(1H-benzo[d]imidazol-2-yl)-3-methylbutyl)(methyl)amino)ethyl)-6-fluoro-1-isopropyl-1,2,3,4-tetrahydronaphthalen-2-yl methylcarbamate;

2-(2-((3-(1H-benzo[d]imidazol-2-yl)-3-methylbutyl)(methyl)amino)ethyl)-6-fluoro-1-isopropyl-1,2,3,4-tetrahydronaphthalen-2-yl (2-(dimethylamino)ethyl)carbamate;

2-(2-((3-(1H-benzo[d]imidazol-2-yl)-3-methylbutyl)(methyl)amino)ethyl)-6-fluoro-1-isopropyl-1,2,3,4-tetrahydronaphthalen-2-yl (2-methoxyethyl)carbamate;

2-(2-((3-(1H-benzo[d]imidazol-2-yl)-3-methylbutyl)(methyl)amino)ethyl)-6-fluoro-1-isopropyl-1,2,3,4-tetrahydronaphthalen-2-yl (2-(pyrrolidin-1-yl)ethyl)carbamate;

2-(2-((3-(1H-benzo[d]imidazol-2-yl)-3-methylbutyl)(methyl)amino)ethyl)-6-fluoro-1-isopropyl-1,2,3,4-tetrahydronaphthalen-2-yl (2-(diethylamino)ethyl)carbamate;

2-(2-((3-(4,7-dimethyl-1H-benzo[d]imidazol-2-yl)propyl)(methyl)amino)ethyl)-6-fluoro-1-isopropyl-1,2,3,4-tetrahydronaphthalen-2-yl morpholine-4-carboxylate;

2-(2-((3-(4,7-dimethyl-1H-benzo[d]imidazol-2-yl)propyl)(methyl)amino)ethyl)-6-fluoro-1-isopropyl-1,2,3,4-tetrahydronaphthalen-2-yl dimethylcarbamate;

2-(2-((4-((2-amino-3,6-dimethylphenyl)amino)-4-oxobutyl)(ethyl)amino)ethyl)-6-fluoro-1-isopropyl-1,2,3,4-tetrahydronaphthalen-2-yl morpholine-4-carboxylate;

2-(2-((2-(1-(1H-benzo[d]imidazol-2-yl)cyclopropyl)ethyl)(methyl)amino)ethyl)-6-fluoro-1-isopropyl-1,2,3,4-tetrahydronaphthalen-2-yl morpholine-4-carboxylate;

3-(2-((3-(1H-benzo[d]imidazol-2-yl)propyl)(methyl)amino)ethyl)-7-fluoro-4-isopropylchroman-3-yl methylcarbamate; and 3-(2-((3-(4,7-dimethyl-1H-benzo[d]imidazol-2-yl)propyl)
(methyl)amino)ethyl)-7-fluoro-4-isopropylchroman-3-yl
methylcarbamate;
or a pharmaceutically acceptable salt thereof.

In some embodiments, the compound of Formula I, or a pharmaceutically acceptable salt thereof, is selected from:
(1S,2S)-2-(2-((3-(1H-benzo[d]imidazol-2-yl)propyl)
(methyl)amino)ethyl)-6-fluoro-1-isopropyl-1,2,3,4-tetrahydronaphthalen-2-yl methylcarbamate;
(1S,2S)-2-(2-((3-(1H-benzo[d]imidazol-2-yl)propyl)
(methyl)amino)ethyl)-6-fluoro-1-isopropyl-1,2,3,4-tetrahydronaphthalen-2-yl methylcarbonate;
(1S,2S)-2-(2-((3-(4,7-dimethyl-1H-benzo[d]imidazol-2-yl)
propyl)(methyl)amino)ethyl)-6-fluoro-1-isopropyl-1,2,3,4-tetrahydronaphthalen-2-yl methylcarbamate;
(1S,2S)-2-(2-((3-(4,7-dimethyl-1H-benzo[d]imidazol-2-yl)
propyl)(methyl)amino)ethyl)-6-fluoro-1-isopropyl-1,2,3,4-tetrahydronaphthalen-2-yl (2-(dimethylamino)ethyl)carbamate;
(1S,2S)-2-(2-((3-(4,7-dimethoxy-1H-benzo[d]imidazol-2-yl)propyl)(methyl)amino)ethyl)-6-fluoro-1-isopropyl-1,2,3,4-tetrahydronaphthalen-2-yl methylcarbamate;
(1S,2S)-2-(2-((3-(4,7-dimethoxy-1H-benzo[d]imidazol-2-yl)propyl)(methyl)amino)ethyl)-6-fluoro-1-isopropyl-1,2,3,4-tetrahydronaphthalen-2-yl (2-methoxyethyl)carbamate;
(1S,2S)-2-(2-((3-(7-chloro-4-methoxy-1H-benzo[d]imidazol-2-yl)propyl)(methyl)amino)ethyl)-6-fluoro-1-isopropyl-1,2,3,4-tetrahydronaphthalen-2-yl dimethylcarbamate;
(1S,2S)-2-(2-((3-(4,6-bis(trifluoromethyl)-1H-benzo[d]imidazol-2-yl)propyl)(methyl)amino)ethyl)-6-fluoro-1-isopropyl-1,2,3,4-tetrahydronaphthalen-2-yl morpholine-4-carboxylate;
(1S,2S)-2-(2-((3-(1H-benzo[d]imidazol-2-yl)-3-methylbutyl)(methyl)amino)ethyl)-6-fluoro-1-isopropyl-1,2,3,4-tetrahydronaphthalen-2-yl morpholine-4-carboxylate;
(1S,2S)-2-(2-((3-(1H-benzo[d]imidazol-2-yl)-3-methylbutyl)(methyl)amino)ethyl)-6-fluoro-1-isopropyl-1,2,3,4-tetrahydronaphthalen-2-yl methylcarbamate;
(1S,2S)-2-(2-((3-(1H-benzo[d]imidazol-2-yl)-3-methylbutyl)(methyl)amino)ethyl)-6-fluoro-1-isopropyl-1,2,3,4-tetrahydronaphthalen-2-yl (2-(dimethylamino)ethyl)carbamate;
(1S,2S)-2-(2-((3-(1H-benzo[d]imidazol-2-yl)-3-methylbutyl)(methyl)amino)ethyl)-6-fluoro-1-isopropyl-1,2,3,4-tetrahydronaphthalen-2-yl (2-methoxyethyl)carbamate;
(1S,2S)-2-(2-((3-(1H-benzo[d]imidazol-2-yl)-3-methylbutyl)(methyl)amino)ethyl)-6-fluoro-1-isopropyl-1,2,3,4-tetrahydronaphthalen-2-yl (2-(pyrrolidin-1-yl)ethyl)carbamate;
(1S,2S)-2-(2-((3-(1H-benzo[d]imidazol-2-yl)-3-methylbutyl)(methyl)amino)ethyl)-6-fluoro-1-isopropyl-1,2,3,4-tetrahydronaphthalen-2-yl (2-(diethylamino)ethyl)carbamate;
(1S,2S)-2-(2-((3-(4,7-dimethyl-1H-benzo[d]imidazol-2-yl)
propyl)(methyl)amino)ethyl)-6-fluoro-1-isopropyl-1,2,3,4-tetrahydronaphthalen-2-yl morpholine-4-carboxylate;
(1S,2S)-2-(2-((3-(4,7-dimethyl-1H-benzo[d]imidazol-2-yl)
propyl)(methyl)amino)ethyl)-6-fluoro-1-isopropyl-1,2,3,4-tetrahydronaphthalen-2-yl dimethylcarbamate;
(1R,2R)-2-(2-((3-(4,7-dimethyl-1H-benzo[d]imidazol-2-yl)
propyl)(methyl)amino)ethyl)-6-fluoro-1-isopropyl-1,2,3,4-tetrahydronaphthalen-2-yl morpholine-4-carboxylate;
(1S,2S)-2-(2-((4-((2-amino-3,6-dimethylphenyl)amino)-4-oxobutyl)(ethyl)amino)ethyl)-6-fluoro-1-isopropyl-1,2,3,4-tetrahydronaphthalen-2-yl morpholine-4-carboxylate;
(1S,2S)-2-(2-((2-(1-(1H-benzo[d]imidazol-2-yl)cyclopropyl)ethyl)(methyl)amino)ethyl)-6-fluoro-1-isopropyl-1,2,3,4-tetrahydronaphthalen-2-yl morpholine-4-carboxylate;
(3S,4S)-3-(2-((3-(1H-benzo[d]imidazol-2-yl)propyl)
(methyl)amino)ethyl)-7-fluoro-4-isopropylchroman-3-yl methylcarbamate;
(3R,4S)-3-(2-((3-(1H-benzo[d]imidazol-2-yl)propyl)
(methyl)amino)ethyl)-7-fluoro-4-isopropylchroman-3-yl methylcarbamate;
(3S,4S)-3-(2-((3-(4,7-dimethyl-1H-benzo[d]imidazol-2-yl)
propyl)(methyl)amino)ethyl)-7-fluoro-4-isopropylchroman-3-yl methylcarbamate; and
(3R,4S)-3-(2-((3-(4,7-dimethyl-1H-benzo[d]imidazol-2-yl)
propyl)(methyl)amino)ethyl)-7-fluoro-4-isopropylchroman-3-yl methylcarbamate;
or a pharmaceutically acceptable salt thereof.

With respect to other compounds that may be disclosed in the art, the present compounds exhibit unexpected properties, such as with respect to duration of action and/or metabolism, such as increased metabolic stability, enhanced oral bioavailability or absorption, and/or decreased drug-drug interactions. The present compounds may exhibit decreased side-effect liability (e.g., with respect to cardiovascular side-effects such as those associated with inhibition of the hERG potassium channel).

III. SYNTHESIS

Compounds provided herein, including salts thereof, can be prepared using known organic synthesis techniques and can be synthesized according to any of numerous possible synthetic routes.

The compounds provided herein (e.g., compounds of any of Formulas I-XI), or pharmaceutically acceptable salts thereof, can be prepared, for example, according to the procedures shown in Scheme 1, wherein $Ag^1$ is a hydroxy activating group (e.g., tosyl, mesyl, and the like), R' is an alkyl group (e.g. a $C_{1-4}$ alkyl group such as methyl or tert-butyl) and variables X, Y, Z, $R^N$, Ar, and n are defined according to the definitions provided herein for compounds of Formula I.

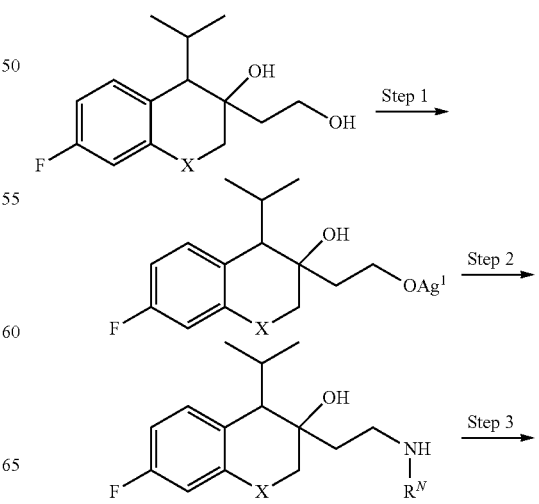

Scheme 1.

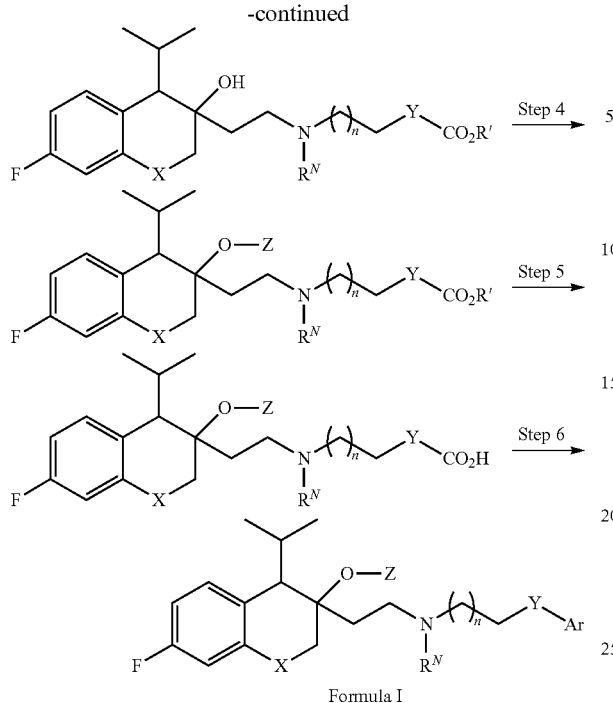

Formula I

The compounds provided herein, or pharmaceutically acceptable salts thereof, can be also prepared, for example, according to the procedures shown in Scheme 2, R' is an alkyl group (e.g. a $C_{1-4}$ alkyl group such as methyl or tert-butyl) and variables X, Y, Z, $R^N$, Ar, and n are defined according to the definitions provided herein for compounds of Formula I.

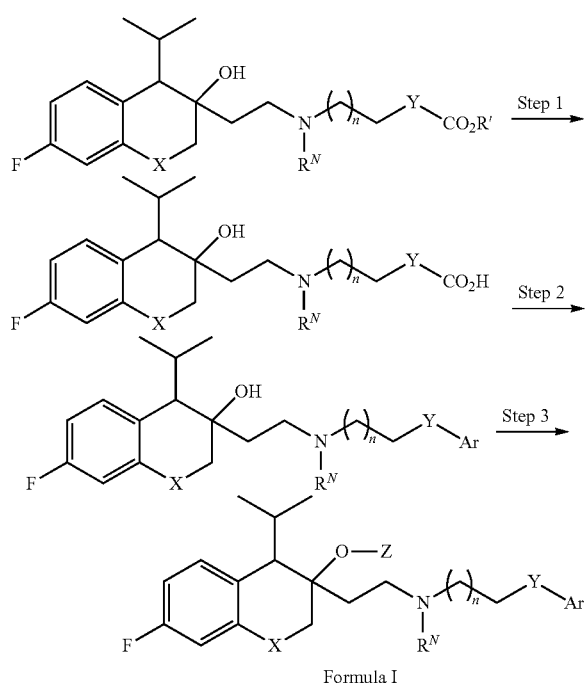

Formula I

The compounds provided herein, or pharmaceutically acceptable salts thereof, can also be prepared from commercially available starting materials such as mibefradil, as shown below in Scheme 3.

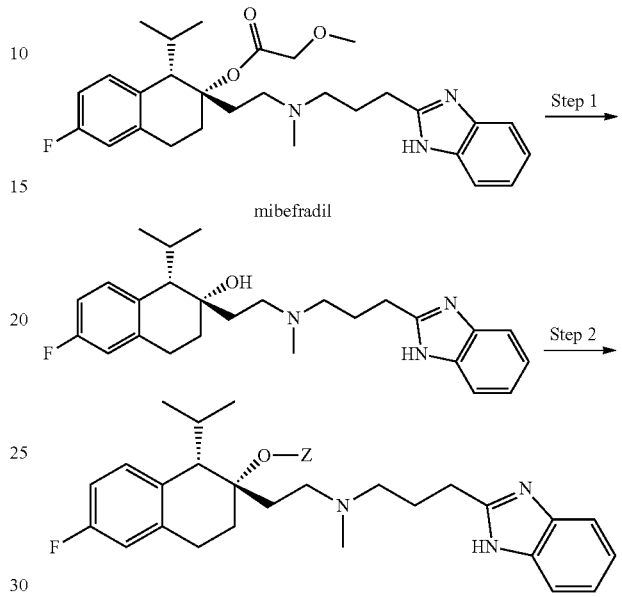

Preparation of compounds described herein can involve the protection and deprotection of various chemical groups. The need for protection and deprotection, and the selection of appropriate protecting groups, can be readily determined by one skilled in the art. The chemistry of protecting groups can be found, e.g., in *Protecting Group Chemistry*, 1$^{st}$ Ed., Oxford University Press, 2000; *March's Advanced Organic chemistry: Reactions, Mechanisms, and Structure*, 5$^{th}$ Ed., Wiley-Interscience Publication, 2001; and Peturssion et al., "Protecting Groups in Carbohydrate Chemistry," *J. Chem. Educ.*, 1997, 74(11), 1297.

The reactions for preparing compounds as described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) ("*Preparative LC-MS Purification: Improved Compound Specific Method*

*Optimization*" Blom, et al., *J. Combi. Chem.* 2004, 6(6) 874-883) and normal phase silica chromatography (Still et al., *J. Org. Chem.*, 1978, 43(14), 2923-25).

It will be appreciated by one skilled in the art that the processes described herein are not the exclusive means by which compounds provided herein may be synthesized and that a broad repertoire of synthetic organic reactions is available to be potentially employed in synthesizing compounds provided herein. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (Journal of Heterocyclic Chemistry, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, $2^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II,* (Pergamon Press, 1996); Smith et al., *March's Advanced Organic Chemistry: Reactions, Mechanisms, and Structure*, $6^{th}$ Ed. (Wiley, 2007); Trost et al. (Ed.), *Comprehensive Organic Synthesis* (Pergamon Press, 1991).

IV. METHODS OF USE

A. Inhibition of Calcium Channels

The present application further provides methods of blocking one or more isoforms of voltage-gated calcium channels. In some embodiments, the method is an in vitro method. In some embodiments, the method is an in vivo method.

In some embodiments, the method comprises blocking one or more isoforms of voltage-gated calcium channels in a cell sample or tissue sample, comprising contacting the cell sample or tissue sample with a compound provided herein (e.g., a compound of any of Formulas I-XI), or a pharmaceutically acceptable salt thereof.

In some embodiments, the method comprises blocking one or more isoforms of T-type voltage-gated calcium channels in the cell sample or tissue sample.

In some embodiments, the isoform is Cav3.1, Cav3.2, Cav3.3, or any combination thereof.

In some embodiments, the method comprises blocking the Cav3.2 isoform of T-type voltage-gated calcium channels in the cell sample or tissue sample.

The present application further provides a method of blocking one or more isoforms of voltage-gated calcium channels in a subject. The term "subject," refers to any animal, including mammals. Example subjects include, but are not limited to, mice, rats, rabbits, dogs, cats, swine, cattle, sheep, horses, primates, and humans. In some embodiments, the subject is a human. In some embodiments, the method comprises administering to the subject a therapeutically effective amount of a compound provided herein (e.g., a compound of any of Formulas I-XI), or a pharmaceutically acceptable salt thereof.

In some embodiments, the method comprises blocking one or more isoforms of T-type voltage gated calcium channels in the subject.

In some embodiments, the isoform is Cav3.1, Cav3.2, Cav3.3, or any combination thereof.

In some embodiments, the method comprises blocking the Cav3.2 isoform of T-type voltage-gated calcium channels in the subject.

The present application further provides a method of treating a disease associated with abnormal activity of one or more isoforms of voltage-gated calcium channels in a subject. In some embodiments, the method comprises administering to the subject a therapeutically effective amount of a compound provided herein (e.g., a compound of any of Formulas I-XI), or a pharmaceutically acceptable salt thereof.

In some embodiments, the disease is associated with abnormal activity of one or more isoforms of T-type voltage-gated calcium channels in the subject.

In some embodiments, disease is associated with abnormal activity of Cav3.1, Cav3.2, Cav3.3, or any combination thereof, in the subject.

In some embodiments, the disease is associated with abnormal activity of the Cav3.2 isoform of T-type voltage-gated calcium channels in the subject.

B. Cancer

Provided herein are methods of treating a cellular proliferative disorder in a patient. The method includes administering to the patient a therapeutically effective amount of a compound of formula (I), or a pharmaceutically acceptable salt thereof, or any of the embodiments thereof.

A cellular proliferative disorder can include cancer. Non-limiting examples of cancers include bladder cancer, brain cancer, breast cancer, colorectal cancer, cervical cancer, gastrointestinal cancer, genitourinary cancer, head and neck cancer, lung cancer, ovarian cancer, prostate cancer, renal cancer, skin cancer and testicular cancer.

More particularly, cancers that may be treated by the compound, compositions and methods described herein include, but are not limited to, the following:

1) Nervous system cancers, including, e.g., cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioma, glioblastoma, glioblastoma multiform, oligodendroglioma, schwannoma, retinoblastoma, and congenital tumors; and cancers of the spinal cord, e.g., neurofibroma, meningioma, glioma, and sarcoma.

2) Breast cancers, including, e.g., $ER^+$ breast cancer, $ER^-$ breast cancer, her2$^-$ breast cancer, her2+ breast cancer, stromal tumors such as fibroadenomas, phyllodes tumors and sarcomas and epithelial tumors such as large duct papillomas; carcinomas of the breast including in situ (non-invasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma; and miscellaneous malignant neoplasms. Further examples of breast cancers can include luminal A, luminal B, basal A, basal B, and triple negative breast cancer, which is estrogen receptor negative ($ER^-$), progesterone receptor negative, and her2 negative (her2$^-$). In some embodiments, the breast cancer may have a high risk Oncotype score.

3) Cardiac cancers, including, e.g., sarcoma, e.g., angiosarcoma, fibrosarcoma, rhabdomyosarcoma, and liposarcoma; myxoma; rhabdomyoma; fibroma; lipoma and teratoma.

4) Lung cancers, including, e.g., bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma.

5) Gastrointestinal cancer, including, e.g., cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma.

6) Genitourinary tract cancers, including, e.g., cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma.

7) Liver cancers, including, e.g., hepatoma, e.g., hepatocellular carcinoma; cholangiocarcinoma; hepatoblastoma; angiosarcoma; hepatocellular adenoma; and hemangioma.

8) Bone cancers, including, e.g., osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors.

9) Gynecological cancers, including, e.g., cancers of the uterus, e.g., endometrial carcinoma; cancers of the cervix, e.g., cervical carcinoma, and pre tumor cervical dysplasia; cancers of the ovaries, e.g., ovarian carcinoma, including serous cystadenocarcinoma, mucinous cystadenocarcinoma, unclassified carcinoma, granulosa thecal cell tumors, Sertoli Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma.

10) Hematologic cancers, including, e.g., cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non-Hodgkin's lymphoma (malignant lymphoma) and Waldenström's macroglobulinemia.

11) Skin cancers, including, e.g., malignant melanoma, basal cell carcinoma, squamous cell carcinoma, Kaposi's sarcoma, moles dysplastic nevi, lipoma, angioma, dermatofibroma, keloids, and psoriasis.

12) Adrenal gland cancers, including, e.g., neuroblastoma.

13) Pancreatic cancers, including, e.g., exocrine pancreatic cancers such as adenocarcinomas (M8140/3), adenosquamous carcinomas, signet ring cell carcinomas, hepatoid carcinomas, colloid carcinomas, undifferentiated carcinomas, and undifferentiated carcinomas with osteoclast-like giant cells; and exocrine pancreatic tumors.

Cancers may be solid tumors that may or may not be metastatic. Cancers may also occur, as in leukemia, as a diffuse tissue. Thus, the term "tumor cell" as provided herein, includes a cell afflicted by any one of the above identified disorders.

The compounds described herein can also be used for the treatment of non-cancer cellular proliferative disorders such as hemangiomatosis in newborns, secondary progressive multiple sclerosis, chronic progressive myelodegenerative disease, neurofibromatosis, ganglioneuromatosis, keloid formation, Paget's disease of the bone, fibrocystic disease of the breast, uterine fibroids, Peyronie's disease, Dupuytren's disease, restenoisis, and cirrhosis.

In some embodiments, the cancer is selected from the group consisting of brain cancer, breast cancer, colon cancer, glioma, glioblastoma, melanoma, ovarian cancer, and pancreatic cancer.

In some embodiments, the cancer is glioma or glioblastoma.

The present invention further provides a compound described herein (e.g., a compound of any of Formulas I-XI), or a pharmaceutically acceptable salt thereof, for use in any of the methods described herein.

The present invention further provides use of a compound described herein (e.g., a compound of any of Formulas I-XI), or a pharmaceutically acceptable salt thereof, for the preparation of a medicament for use in any of the methods described herein.

C. Other Diseases

In addition to cancer, T-type calcium channels have been implicated in a wide range of biological functions. This has suggested a potential role for these receptors in a variety of disease processes in humans or other species. The compounds of the present invention have utility in treating, preventing, ameliorating, controlling or reducing the risk of a variety of neurological and psychiatric disorders associated with calcium channels, including one or more of the following conditions or diseases: movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), chronic fatigue syndrome, fatigue, including Parkinson's fatigue, multiple sclerosis fatigue, fatigue caused by a sleep disorder or a circadian rhythm disorder, medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, seizure disorders, epilepsy, and dyskinesias [including tremor (such as rest tremor, essential tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), restless leg syndrome and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia); Angelman's Syndrome, Prader-Willi Syndrome, heart disease, abnormal heart rhythms and arrythmias, myocardial infarction, congestive heart failure, coronary heart disease, sudden death, stroke, sexual and reproductive dysfunction, such as impaired fertility, infertility, diseases or disorders where abnormal oscillatory activity occurs in the brain, including depression, migraine, neuropathic pain, Parkinson's disease, psychosis and schizophrenia, as well as diseases or disorders where there is abnormal coupling of activity, particularly through the thalamus; enhancing cognitive function; enhancing memory; increasing memory retention; increasing trained performance; increasing immune response; increasing immune function; hot flashes; night sweats; extending life span; schizophrenia; muscle-related disorders that are controlled by the excitation/relaxation rhythms imposed by the neural system such as cardiac rhythm and other disorders of the cardiovascular system; conditions related to proliferation of cells such as vasodilation or vasorestriction and blood pressure; cardiac arrhythmia; hypertension; congestive heart failure; conditions of the genital/urinary system; disorders of sexual function and fertility; adequacy of renal function; responsivity to anesthetics; sleep disorders, sleep disturbances, including enhancing sleep quality, improving sleep quality, increasing sleep efficiency, augmenting sleep maintenance; increasing the value which is calculated from the time that a subject sleeps divided by the time that a subject is attempting to sleep; improving sleep initiation; decreasing sleep latency or onset (the time it takes to fall asleep); decreasing difficulties in falling asleep; increasing sleep continuity; decreasing the number of awakenings during sleep; decreasing intermittent wakings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; increasing the amount of Delta sleep early in the sleep cycle, increasing REM sleep late in the sleep cycle; decreasing nocturnal arousals, especially early morning awakenings; increasing daytime alertness; reducing daytime drowsiness; treating or reducing excessive daytime sleepiness; increasing satisfaction with the intensity of sleep; increasing sleep maintenance; idiopathic insomnia; sleep problems; insomnia, hypersomnia, idiopathic hypersomnia, repeatability hypersomnia, intrinsic hypersomnia, narcolepsy, interrupted sleep, sleep apnea, obstructive sleep apnea, wakefulness, nocturnal myoclonus, REM sleep interruptions, jet-lag, shift workers' sleep disturbances, dyssomnias, night terror, insomnias associated with depression, emotional/mood disorders, Alzheimer's disease or cognitive impairment, as well as sleep walking and enuresis, and sleep disorders which accompany aging; Alzheimer's sundowning; conditions associated with circadian rhythmicity as well as mental and physical disorders associated with travel across time zones and with rotating shift-work schedules, conditions due to drugs which cause reductions in REM sleep as a side effect; fibromyalgia; syndromes which are manifested by non-restorative sleep and muscle pain or sleep apnea which is associated with respiratory disturbances during sleep; conditions which result from a diminished quality of sleep; mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder, mood disorders due to a general medical condition, and substance-induced mood disorders; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; acute neurological and psychiatric disorders such as cerebral deficits subsequent to cardiac bypass surgery and grafting, stroke, ischemic stroke, cerebral ischemia, spinal cord trauma, head trauma, perinatal hypoxia, cardiac arrest, hypoglycemic neuronal damage; Huntington's Chorea; amyotrophic lateral sclerosis; multiple sclerosis; ocular damage; retinopathy; cognitive disorders; idiopathic and drug-induced Parkinson's disease; muscular spasms and disorders associated with muscular spasticity including tremors, epilepsy, convulsions; cognitive disorders including dementia (associated with Alzheimer's disease, ischemia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics); attention deficit/hyperactivity disorder (ADHD); conduct disorder; migraine (including migraine headache); urinary incontinence; overactive bladder (OAB); urge urinary incontinence (UUI); lower urinary tract symptoms (LUTS); substance tolerance, substance withdrawal (including, substances such as opiates, nicotine, tobacco products, alcohol, benzodiazepines, cocaine, sedatives, hypnotics, etc.); psychosis; schizophrenia; anxiety (including generalized anxiety disorder, panic disorder, and obsessive compulsive disorder); mood disorders (including depression, mania, bipolar disorders); trigeminal neuralgia; hearing loss; tinnitus; neuronal damage including ocular damage; retinopathy; macular degeneration of the eye; emesis; brain edema; pain, including acute pain, chronic pain, severe pain, intractable pain, inflammatory pain, chronic inflammatory pain, diabetic neuropathy, chronic neuropathic pain, post-traumatic pain, bone and joint pain (osteoarthritis), repetitive motion pain, dental pain, cancer pain, myofascial pain (muscular injury, fibromyalgia), perioperative pain (general surgery, gynecological), chronic pain, neuropathic pain, post-traumatic pain, trigeminal neuralgia, migraine and migraine headache. Thus, in some embodiments, the compounds described herein, or any of the embodiments or examples thereof, can be used in a method of treating controlling, ameliorating or reducing the risk of any of the diseases mentioned above by administering a therapeutically effective amount of the compound to an individual in need of such treatment.

In some embodiments, the compounds described herein, or any of the embodiments or examples thereof, can be used in a method of treating, controlling, ameliorating or reducing the risk of epilepsy, including absence epilepsy; treating or controlling Parkinson's disease; treating essential tremor; treating or controlling pain, including neuropathic pain; enhancing the quality of sleep; augmenting sleep maintenance; increasing REM sleep; increasing slow wave sleep; decreasing fragmentation of sleep patterns; treating insomnia; enhancing cognition; increasing memory retention; treating or controlling depression; treating or controlling psychosis; or treating, controlling, ameliorating or reducing the risk of schizophrenia, in a mammalian patient in need thereof which comprises administering to the patient a therapeutically effective amount of the compound of the present invention. The subject compounds are further useful in a method for the prevention, treatment, control, amelioration, or reduction of risk of the diseases, disorders and conditions noted herein. The methods are carried out by administering a therapeutically effective amount of the compound to an individual in need of such treatment.

D. Methods of Imaging

In some embodiments, the compounds described herein, or any of the examples or embodiments thereof, may be useful for enhancing the efficacy of an imaging agent for imaging a disease such as cancer or a pre-cancerous disease or a cellular proliferative disorder, for example according to the methods described in WO 2011/109262. The method can be used to image various diseases or conditions, including unstable angina, hypertension, epilepsy, neuropathic pain, petit mal seizure, absence seizure, age related macular degeneration, cancer and pre-cancerous conditions. In other embodiments, the method can be used to image tumors and pre-cancerous tumors.

While not being limited by thereof, the method for imaging a disease or condition, the T-type calcium channel inhibitor, which can be any of the compounds described herein, or any of the embodiments or examples thereof, is first administered in an effective amount to stop proliferation of eukaryotic cells at the cell cycle checkpoint between the G1 and S phase (G1/S). Varying lengths of the cell cycle are determined predominately by the time spent in the G1 phase. The lengths of the S, G2 and M phases are relatively invariant. Because of this, any particular cell in a population will reside in G1 for a period of time before the cell enters the S phase of the cell cycle. To stop the cell cycle from continuing past a cell cycle checkpoint, the T-type calcium channel inhibitor can be administered. The administration of a cell cycle inhibitor causes asynchronously proliferating cancer cells in a population to accumulate at G1/S as they proceed through the cell cycle because their ability to proceed to the S phase is arrested by the cell cycle inhibitor. For a cell to move from G1 phase to S phase through the cell cycle checkpoint, the cell requires influx of extracellular calcium to trigger biochemical cascades that are necessary for the progression. Removal of calcium from the extracellular medium blocks cell cycle transit for each cell. Thus, each cell persists in G1 phase as long as it would in the presence of extracellular calcium, but becomes locked in place when G1/S is reached without calcium, thereby synchronizing cells at G1/S. Calcium influx to a cell is necessary for proliferation and transit through the cell cycle.

Administration of the T-type calcium channel inhibitor increases the percentage of cells at G1/S. To take advantage of the increase of cells at G1/S, the T-type calcium channel inhibitor can be administered to the imaging subject for a period of time before imaging. This period of time can be between about 1 day and about 10 days, (e.g., about 5 days and about 7 days, inclusively). Subsequent to administration of the T-type calcium channel inhibitor, there can be a period during which no T-type calcium channel inhibitor is administered (e.g., for a period from about 30 minutes to about 72 hours). This period can allow cells which have accumulated at G1/S to enter the S phase of the cell cycle (e.g., about 5% to about 25% can accumulate at G1/S). The increase in number of cells in the S phase makes a subsequent administered dose of an imaging marker more effective because a large percentage of cells will uptake the imaging marker in each dose.

Subsequent to the administration of the T-type calcium channel inhibitor, an imaging marker is administered that is targeted to be uptaken in the S phase of the cell cycle. The period between the first administration of the cell cycle inhibitor and the imaging marker allows the accumulation of cells at G1/S of the cell cycle. This method increases the percentage of the cells which are in the S phase, thereby increasing the uptake of imaging marker into those cells, thereby increasing the sensitivity of imaging.

Some of the examples of the possible imaging markers include $^{11}C$ Methionine, 2-deoxy-2-($^{18}F$)fluoro-D-glucose, tritiated 2-deoxy-2-fluoro-D-glucose and fluoro deoxythymidines such as [$^{18}F$]-3'-fluoro-3'-deoxy-L-thymidine).

After the imaging marker is administered to the mammal, the mammal is then imaged. The imaging marker can be administered at any suitable dose, for example about 100 mBq to about 600 mBq. The mammal can be imaged using any suitable imaging apparatus, for example an apparatus capable of gathering a magnetic resonance image (MRI), a positron emission tomogram (PET scan) or a computer tomogram (CT scan). The images gleaned by a suitable imaging apparatus will be more sensitive than images taken of mammals with no pre-treatment of a cell cycle inhibitor. The scans taken after administration of cell cycle inhibitors will be more sensitive because the diseased cells will have a higher uptake of the imaging markers as compared to uptake of imaging markers of cells that have not had an administration of a cell cycle inhibitor.

V. COMBINATION THERAPIES

The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention is envisioned. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is envisioned. Accordingly, the pharmaceutical compositions of the present invention include those that also contain one or more other active ingredients, in addition to a compound of the present invention.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, including about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

One or more additional therapeutic agents such as, for example, steroids, immunosuppressants, chemotherapeutic agents, radiation therapy, and anesthetics (e.g., for use in combination with a surgical procedure), can be used in combination with the compounds and salts provided herein.

Example steroids include, but are not limited to, corticosteroids such as cortisone, dexamethasone, hydrocortisone, methylprednisolone, prednisolone, and prednisone.

Example immunosuppressants include, but are not limited to, azathioprine, chlorambucil, cyclophosphamide, cyclosporine, daclizumab, infliximab, methotrexate, and tacrolimus.

Example chemotherapeutic agents include, but are not limited to, temozolomide, 5-fluorouracil, 6-mercaptopurine, bleomycin, carboplatin, cisplatin, dacarbazine, doxorubicin, epirubicin, etoposide, hydroxyurea, ifosfamide, irinotecan, topotecan, methotrexate, mitoxantrone, oxaliplatin, paclitaxel, docetaxel, vinblastine, vincristine, vinorelbine, vindesine, and mitomycin C.

Example anesthetics include, but are not limited, to local anesthetics (e.g., lidocaine, procain, ropivacaine) and general anesthetics (e.g., desflurane, enflurane, halothane, isoflurane, methoxyflurane, nitrous oxide, sevoflurane, mmobarbital, methohexital, thiamylal, thiopental, diazepam, lorazepam, midazolam, etomidate, ketamine, propofol, alfentanil, fentanyl, remifentanil, buprenorphine, butorphanol, hydromorphone levorphanol, meperidine, methadone, morphine, nalbuphine, oxymorphone, pentazocine).

For example, one or more of the following agents may be used in combination with the compounds provided herein and are presented as a non-limiting list: an alkylating agent, a cytostatic agent, cisplatin, doxorubicin, taxol, etoposide, irinotecan, topotecan, paclitaxel, docetaxel, epothilones, tamoxifen, 5-fluorouracil, methotrexate, temozolomide, cyclophosphamide, tipifarnib, gefitinib, erlotinib hydrochloride, antibodies to EGFR, imatinib mesylate, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, oxaliplatin, folinic acid, pentostatin, vinblastine, vincristine, vindesine, bleomycin, dactinomycin, daunorubicin, epirubicin, idarubicin, mithramycin, deoxycoformycin, mitomycin-C, L-asparaginase, teniposide, 17α-ethinylestradiol, diethylstilbestrol, testosterone, prednisone, fluoxymesterone, dromostanolone propionate, testolactone, megestrol acetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, carboplatin, hydroxyurea, amsacrine, procarbazine, mitotane, mitoxantrone, levamisole, vinorelbine, anastrazole, letrozole, capecitabine, reloxafine, hexamethylmelamine, bevacizumab, bexxar, velcade, zevalin, trisenox, xeloda, porfimer, erbitux, thiotepa, altretamine, trastuzumab, fulvestrant, exemestane, rituximab, alemtuzumab, clofarabine, cladribine, aphidicolin, sunitinib, dasatinib, tezacitabine, triapine, didox, trimidox, amidox, bendamustine, ofatumumab, and idelalisib.

The compounds described herein can further be used in combination with other methods of treating cancers, for example by chemotherapy, irradiation or surgery. The compounds can be administered in combination with one or more anti-cancer drugs, such as a chemotherapeutics. abarelix, aldesleukin, alemtuzumab, alitretinoin, allopurinol, altretamine, anastrozole, arsenic trioxide, asparaginase, azacitidine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat and zoledronate.

In some embodiments, the additional therapeutic agent is administered simultaneously with a compound or salt provided herein. In some embodiments, the additional therapeutic agent is administered after administration of the compound or salt provided herein. In some embodiments, the additional therapeutic agent is administered prior to administration of the compound or salt provided herein. In some embodiments, the compound or salt provided herein is administered during a surgical procedure. In some embodiments, the compound or salt provided herein is administered in combination with an additional therapeutic agent during a surgical procedure.

In some embodiments, the compounds described herein, or any of the examples or embodiments thereof, may be useful for enhancing the efficacy of a chemotherapeutic agent or radiation in killing proliferating cells in the treatment of a cellular proliferative disorder such as cancer, such as any of the types of cellular proliferative disorder or cancers described above, for example according to the methods described in WO2010/141842.

While not being limited by any theory, it is believed that administration of a T-type calcium channel inhibitor can cause asynchronously progressing or proliferating cancer cells in a population to accumulate at the G1/S checkpoint as they proceed through the cell cycle because their ability to proceed to the S phase is arrested by the cell cycle inhibitor. For a cell to move from G1 phase to S phase through the cell cycle checkpoint, the cell requires influx of extracellular calcium to trigger biochemical cascades that are necessary for the progression. Removal of calcium from the extracellular medium blocks cell cycle transit for each cell. This blocking can be accomplished through administration of a T type calcium channel inhibitor. Thus, each cell persists in G1 phase as long as it would in the presence of extracellular calcium, but becomes locked in place when G1/S is reached without calcium, thereby synchronizing cells at G1/S.

The administration of the cell cycle inhibitor increases the percentage of cells at G1/S. Subsequent to this administration, a dosage of at least one chemotherapeutic agent, a dosage of radiation, or a dosage of both can be administered, the dosage being targeted to kill cells in the S phase of the cell cycle. The dosage of at least one chemotherapeutic agent can be administered before, after or during a dosage of radiation. The dosage of radiation can be administered before, after or during a dosage of at least one chemotherapeutic. This method increases the percentage of the cells which are in the S or M phase, thereby increasing the effectiveness of the dosage of at least one chemotherapeutic agent, the dosage of radiation, or the dosage of both and subsequently reducing the toxic load required to kill a predetermined amount of eukaryotic cells. The chemotherapeutic agent can be any of the cancer chemotherapeutic agents described above or combinations thereof.

The compounds described herein may be employed in combination with an anti-seizure agent such as carbamazepine, clonazepam, divalproex, ethosuximide, felbamate, fosphenyloin, gabapentin, lamotrigine, levetiracetam, lorazepam, midazolam, oxcarbazepine, phenobarbital, phenyloin, primidone, tiagabine, topiramate, valproate, vigabatrin or zonisamide. In another embodiment, the subject compound may be employed in combination with acetophenazine, alentemol, benzhexyl, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, risperidone, sulpiride, tetrabenazine, trihexyphenidyl, thioridazine, thiothixene, trifluoperazine or valproic acid.

In another embodiment, the compounds of the present invention may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexyl)hydrochloride, COMT inhibitors such as entacapone, MOA-B inhibitors, antioxidants, A2a adenosine receptor antagonists, cholinergic agonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the compounds of the present invention may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form.

In another embodiment, the compounds of the present invention may be employed in combination with an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the subject compound may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antitussive such as codeine, hydrocodone, caramiphen, carbetapentane, or dextramethorphan; a diuretic; and a sedating or non-sedating antihistamine. In another embodiment, the subject compound may be employed in combination with an L-type calcium channel antagonist, such as amlodipine. In another embodiment, the subject compound may be employed in combination with an NK-1 receptor antagonists, a beta-3 agonist, a 5-alpha reductase inhibitor (such as finasteride or dutasteride), a M3 muscarinic receptor antagonist (such as darifenacin, fesoterodine, oxybutynin, solifenacin, tolterodine or trosipium) or duloxetine.

In another embodiment, the compounds of the present invention may be administered in combination with compounds which are known in the art to be useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, other orexin antagonists, orexin agonists, prokineticin agonists and antagonists, pyrazolopyrimidines, other T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

In another embodiment, the compounds of the present invention may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, .alpha.-adrenoreceptor antagonists, neurokinin-1 receptor antagonists, atypical anti-depressants, benzodiazepines, 5-HTiA agonists or antagonists, especially 5-HTiA partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

In another embodiment, the compounds of the present invention may be employed in combination with anti-Alzheimer's agents; beta-secretase inhibitors; gamma-secretase inhibitors; growth-hormone secretagogues; recombinant growth hormone; HMG-CoA reductase inhibitors; NSAID's including ibuprofen; vitamin E; anti-amyloid antibodies; CB-1 receptor antagonists or CB-1 receptor inverse agonists; antibiotics such as doxycycline and rifampin; N-methyl-D-aspartate (NMDA) receptor antagonists, such as memantine; cholinesterase inhibitors such as galantamine, rivastigmine, donepezil, and tacrine; growth hormone secretagogues such as ibutamoren, ibutamoren mesylate, and capromorelin; histamine H.sub.3 antagonists; AMPA agonists; PDE IV inhibitors; GABA.sub.A inverse agonists; or neuronal nicotinic agonists.

VI. FORMULATION, DOSAGE FORMS AND ADMINISTRATION

When employed as pharmaceuticals, the compounds and salts provided herein can be administered in the form of pharmaceutical compositions. These compositions can be prepared as described herein or elsewhere, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral, or parenteral. Parenteral administration includes intravenous, intraarterial, subcutaneous, intraperitoneal intramuscular or injection or infusion; or intracranial, (e.g., intrathecal or intraventricular, administration). Parenteral administration can be in the form of a single bolus dose, or may be, for example, by a continuous perfusion pump. In some embodiments, the compounds, salts, and pharmaceutical compositions provided herein are suitable for parenteral administration. In some embodiments, the compounds, salts, and pharmaceutical compositions provided herein are suitable for intravenous administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Also provided are pharmaceutical compositions which contain, as the active ingredient, a compound provided herein, or a pharmaceutically acceptable salt thereof, in combination with one or more pharmaceutically acceptable carriers (e.g., excipients). In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders.

Some examples of suitable excipients include, without limitation, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include, without limitation, lubricating agents such as talc, magnesium stearate, and mineral oil; wetting agents; emulsifying and suspending agents; preserving agents such as methyl- and propylhydroxy-benzoates; sweetening agents; flavoring agents, or combinations thereof.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual subject, the severity of the subject's symptoms, and the like.

EXAMPLES

The following examples are offered for illustrative purposes, and are not intended to limit the invention.

Intermediate 1. 2-((1S,2S)-6-Fluoro-2-hydroxy-1-isopropyl-1,2,3,4-tetrahydronaphthalen-2-yl)ethyl 4-methylbenzenesulfonate

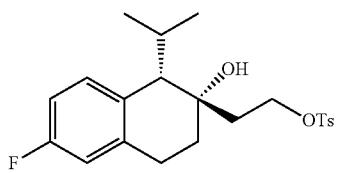 [SMILES: Cc1ccc(S(=O)(=O)OCC[C@@]2(O)CCc3cc(F)ccc3[C@@H]2C(C)C)cc1]

To a solution of (1S,2S)-6-fluoro-2-(2-hydroxyethyl)-1-isopropyl-1,2,3,4-tetrahydronaphthalen-2-ol (160 g, 627.45 mmol, 1.0 eq.) in DCM (1600 mL) were added triethylamine (132.5 mL, 941.17 mmol, 1.5 eq), DMAP (7.66 g, 62.74 mmol) and tosyl chloride (155.5 g, 815.68 mmol, 1.3 eq.) at rt. The reaction mixture was stirred at rt for 12 h. The reaction mixture was taken up in saturated NaHCO$_3$ solution (5000 mL), extracted with DCM (1500 mL×2). The combine organics were dried over Na$_2$SO$_4$ and concentrated to afford Intermediate 1 as a transparent semisolid which solidified upon standing overnight. (180 g, 70%). MS: 424.4 m/z (M+NH$_4$)+.

Intermediate 2. (1S,2S)-6-Fluoro-1-isopropyl-2-(2-(methylamino)ethyl)-1,2,3,4-tetrahydronaphthalen-2-ol

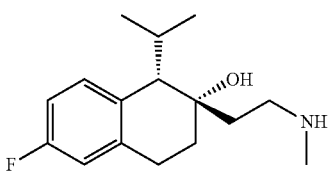 [SMILES: CNCC[C@@]1(O)CCc2cc(F)ccc2[C@@H]1C(C)C]

A mixture of Intermediate 1 (180 g, 443.34 mmol) and methylamine 2M in MeOH (900 mL) was stirred at 40° C. for 12 h under autoclave. The reaction mixture was taken up in ice cold water (4000 mL) to give solid precipitate. The precipitate was filtered, washed with water and dried under vacuum to obtain Intermediate 2 (115 g, 97%). MS: 266.3 m/z (M+H)+.

Intermediate 3. 3-(1H-Benzo[d]imidazol-2-yl)-3-methylbutanal

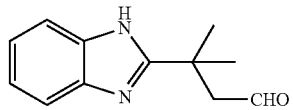

Step 1. 3,3-dimethyldihydrofuran-2(3H)-one

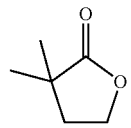

To a solution of dihydrofuran-2(3H)-one (2.0 g, 0.023 mol, 1.0 eq.) in dry THF was added sodium hydride (3.34 g, 0.069 mol, 3.0 eq.) portionwise at 0° C. and refluxed for 30 min. To the reaction mixture was added MeI (11.5 g, 0.081 mol, 3.5 eq.) slowly over 1 h under reflux. After 2 h the reaction mixture was diluted with Et$_2$O and acidified with 1N HCl and stirred for overnight. The organic layer was separated, concentrated under reduced pressure. The crude (350 mg) was used in the next step without any purification.

Step 2. 3-(1H-benzo[c]imidazol-2-yl)-3-methylbutan-1-ol

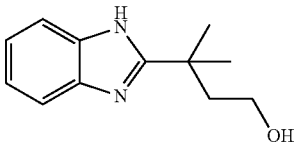

The crude mixture from Step 1 (5.0 g, 0.046 mol, 1.0 eq.) and o-phenylenediamine (10.5 g, 0.92 mol, 2 eq.) were taken in a flask and added 25 mL 5.5M HCl at rt then stirred for 12 h at 90° C. The reaction mixture was diluted with acetone and neutralized with sat. NaHCO$_3$, dried over Na$_2$SO$_4$. The organic layer was concentrated under reduced pressure and purified by flash column on silica gel 230-400 mesh to afforded 3-(1H-benzo[d]imidazol-2-yl)-3-methylbutan-1-ol (1.5 g, 17%) as a grey solid. MS: 205.0 m/z (M+H)+.

Step 3. 3-(1H-Benzo[c]imidazol-2-yl)-3-methylbutanal

To a solution of 3-(1H-benzo[d]imidazol-2-yl)-3-methylbutan-1-ol (1 g, 0.005 mol, 1 eq.) in DCM (20 mL) was added Dess Martin Periodinone (3.1 g, 0.007 mmol, 1.5 eq.)

at 0° C. The reaction was warmed to rt and stirred at rt for 3 h. The reaction mass was then quenched with sat. Solution of NaHCO₃ and extracted with DCM (100 mL×2). The combined organics were collected, washed with brine, dried Na₂SO₄ and evaporated to dryness. The residue was purified by flash column chromatography on silica gel using DCM/MeOH to afford Intermediate 3 (0.84 g, 84.84%) as a grey solid. MS: 203.2 m/z (M+H)+.

Example 1. (1S,2S)-2-(2-((3-(1H-Benzo[d]imidazol-2-yl)propyl)(methyl)amino)ethyl)-6-fluoro-1-isopropyl-1,2,3,4-tetrahydronaphthalen-2-yl methylcarbamate

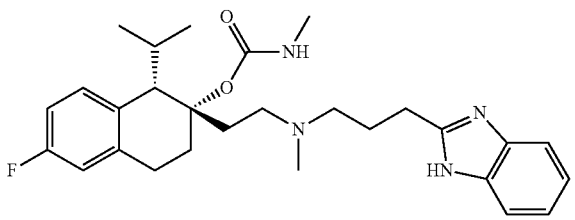 [SMILES: CNC(=O)O[C@]1(CCN(C)CCCc2nc3ccccc3[nH]2)CCc2cc(F)ccc2[C@@H]1C(C)C]

Step 1. (1S,2S)-2-(2-((3-(1H-Benzo[d]imidazol-2-yl)propyl)(methyl)amino)ethyl)-6-fluoro-1-isopropyl-1,2,3,4-tetrahydronaphthalen-2-ol

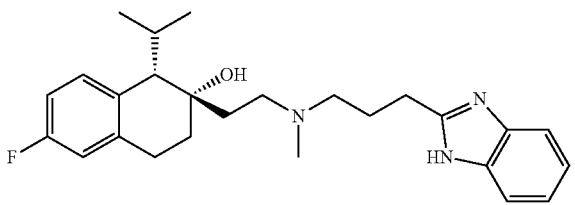 [SMILES: CC(C)[C@H]1c2ccc(F)cc2CC[C@]1(O)CCN(C)CCCc1nc2ccccc2[nH]1]

A mixture of mibefradil (2 g, 4.04 mmol, 1.0 eq.), EtOH (20 mL 10 vol.) and 1N NaOH 20 mL (10 vol), were taken in a sealed tube. The reaction mixture was stirred at 60° C. for 3.4 h. The reaction mixture was cool to rt and concentrated under reduced pressure. The residue was taken in water (20 mL) and extracted with DCM. The organic layer was dried over Na₂SO₄ and concentrated. The crude compound was purified on a COMBIFLASH® column using 2.6-3% MeOH in DCM as eluent to afford (1S,2S)-2-(2-((3-(1H-benzo[d]imidazol-2-yl)propyl)(methyl)amino)ethyl)-6-fluoro-1-isopropyl-1,2,3,4-tetrahydronaphthalen-2-ol (1.2 g, 60%). MS: 424.2 m/z (M+H)⁺.

Step 2. (1S,2S)-2-(2-((3-(1H-Benzo[d]imidazol-2-yl)propyl)(methyl)amino)ethyl)-6-fluoro-1-isopropyl-1,2,3,4-tetrahydronaphthalen-2-yl methylcarbamate To a solution of (1S,2S)-2-(2-((3-(1H-benzo[d]imidazol-2-yl)propyl)(methyl)amino)ethyl)-6-fluoro-1-isopropyl-1,2,3,4-tetrahydronaphthalen-2-ol (0.250 g, 0.59 mmol, 1 eq.) in DCM (2.5 mL) at 0° C., DIPEA (0.2 mL, 0.70 mmol, 1.2 eq.) and 4-nitrophenylchloroformate (0.180 g, 0.88 mmol, 1.5 eq.) were successively added. The solution was brought to rt and stirred for 3 h. The reaction mixture was then cooled to 0° C. and methylamine (33% in MeOH) (0.11 mL, 0.88 mmol, 1.5 eq.) was added and the mixture was stirred for 3 h at rt. The reaction mixture was diluted with water (20 mL) and extracted with DCM. The organic layer was dried over Na₂SO₄ and then concentrated. The crude compound was purified by column chromatography on silica gel (100-200 mesh) using 2.4-2.8% MeOH in DCM as eluent to afford Example 1 (0.060 g, 22%). MS: 481.5 m/z (M+H)⁺; 1H NMR: (400 MHz, CD₃OD) δ: 12.12 (s, 1H), 7.48 (bs, 1H), 7.38 (bs, 1H), 7.10 (d, J=4.0 Hz, 2H), 7.03 (dd, J=5.6, 8.8 Hz, 1H), 6.97 (d, J=4.4 Hz, 1H), 6.92-6.88 (m, 2H), 3.39 (s, 1H), 2.90 (dd, J=7.2, 18.4 Hz, 1H), 2.74 (t, J=8.0 Hz, 3H), 2.53 (s, 3H), 2.33-2.25 (m, 3H), 2.14-2.04 (m, 3H), 2.02 (s, 3H), 1.91-1.79 (m, 3H), 1.58-1.51 (m, 1H), 1.01 (d, J=6.8 Hz, 3H), 0.33 (d, J=6.8 Hz, 3H).

Example 2. (1S,2S)-2-(2-((3-(1H-Benzo[d]imidazol-2-yl)propyl)(methyl)amino)ethyl)-6-fluoro-1-isopropyl-1,2,3,4-tetrahydronaphthalen-2-yl methylcarbonate

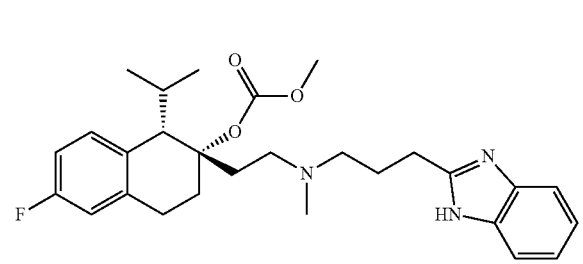 [SMILES: COC(=O)O[C@]1(CCN(C)CCCc2nc3ccccc3[nH]2)CCc2cc(F)ccc2[C@@H]1C(C)C]

To a solution of (1S,2S)-2-(2-((3-(1H-benzo[d]imidazol-2-yl)propyl)(methyl)amino)ethyl)-6-fluoro-1-isopropyl-1,2,3,4-tetrahydronaphthalen-2-ol (Example 1, Step 1, 0.250 g, 0.59 mmol, 1 eq.) in toluene was added K₂CO₃ (0.131 g, 0.949 mmol, 2 eq.) followed by methyl chloroformate (0.084 g, 0.885 mmol, 1.5 eq.) at 0° C. The reaction mixture was stirred for 16 h at rt. The reaction mixture was diluted with water (15 mL) and extracted with DCM. The combined organic layer was dried over Na₂SO₄ and then concentrated. The crude compound was purified by column chromatography on silica gel (100-200 mesh) using 3-3.8% MeOH in DCM as eluent to afford Example 2 (0.060 g, 21%). MS: 482.5 m/z (M+H)⁺; ¹H NMR: (400 MHz, CD₃OD) δ: 7.46 (dd, J=3.2, 6.0 Hz, 2H), 7.21 (dd, J=3.2, 6.0 Hz, 2H), 7.04 (dd, J=5.6, 8.4 Hz, 1H), 6.85 (td, J=8.4, 2.4 Hz, 1H), 6.78 (dd, J=2.4, 9.6 Hz, 1H), 3.72 (s, 3H), 3.01-2.70 (m, 8H), 2.41 (s, 3H), 2.36-2.28 (m, 1H), 2.15-1.88 (m, 6H), 1.08 (d, J=7.2 Hz, 3H), 0.44 (d, J=6.8 Hz, 3H).

Example 3. (1S,2S)-2-(2-((3-(4,7-Dimethyl-1H-benzo[d]imidazol-2-yl)propyl)(methyl)amino)ethyl)-6-fluoro-1-isopropyl-1,2,3,4-tetrahydronaphthalen-2-yl methylcarbamate

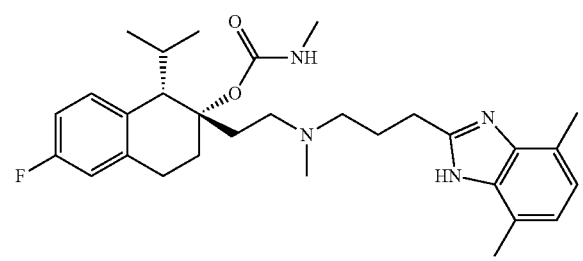 [SMILES: CNC(=O)O[C@]1(CCN(C)CCCc2nc3c(C)ccc(C)c3[nH]2)CCc2cc(F)ccc2[C@@H]1C(C)C]

Step 1. (1S,2S)-2-(2-((3-(4,7-Dimethyl-1H-benzo[d]imidazol-2-yl)propyl)(methyl)amino)ethyl)-6-fluoro-1-isopropyl-1,2,3,4-tetrahydronaphthalen-2-ol

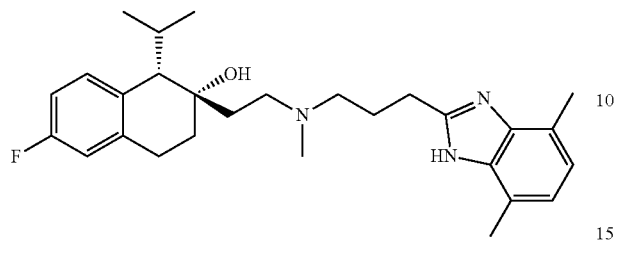

A solution of Intermediate 1 (0.5 g, 1.23 mmol, 1.0 eq.) and 3-(4,7-dimethyl-1H-benzo[d]imidazol-2-yl)-N-methylpropan-1-amine (0.320 g 1.476 mmol, 1.2 eq.) in triethylamine (25 mL) was stirred at 80° C. for 24 h. The reaction mixture was quenched with water (20 mL) and extracted in DCM (20 mL×3). The combined organics were collected, washed with brine, dried over $Na_2SO_4$ and evaporated to dryness. The crude compound was purified on a COMBIFLASH® column using 3-4% MeOH in DCM as eluent to afford (1S,2S)-2-(2-((3-(4,7-dimethyl-1H-benzo[d]imidazol-2-yl)propyl)(methyl)amino)ethyl)-6-fluoro-1-isopropyl-1,2,3,4-tetrahydronaphthalen-2-ol (0.300 g, 54%). MS: 452.5 m/z (M+H)$^+$.

Step 2. (1S,2S)-2-(2-((3-(4,7-Dimethyl-1H-benzo[d]imidazol-2-yl)propyl)(methyl)amino)ethyl)-6-fluoro-1-isopropyl-1,2,3,4-tetrahydronaphthalen-2-yl methylcarbamate To a solution of (1S,2S)-2-(2-((3-(4,7-dimethyl-1H-benzo[d]imidazol-2-yl)propyl)(methyl)amino)ethyl)-6-fluoro-1-isopropyl-1,2,3,4-tetrahydronaphthalen-2-ol (0.2 g, 0.44 mmol, 1 eq.) in DCM (2 mL) at 0° C., DIPEA (0.1 mL, 0.88 mmol, 2.0 eq.) and 4-nitrophenylchloroformate (0.133 g, 0.66 mmol, 1.5 eq.) were successively added. The solution was brought to rt and stirred for 3 h. The reaction mixture was then cooled to 0° C. and methylamine (33% in MeOH) (2 mL) was added and the reaction mixture was stirred for 3 h at rt. The reaction mixture was diluted with water (20 mL) and extracted with DCM. The organic layer was dried over $Na_2SO_4$ and evaporated to dryness. The crude compound was purified on a COMBIFLASH® column using 2.6-3% MeOH in DCM as eluent to afford Example 3 (0.060 g, 54%). MS: 509.5 m/z (M+H)$^+$; 1H NMR: (400 MHz, $CD_3OD$) δ: 6.99 (dd, J=5.6, 8.4 Hz, 1H), 6.88 (s, 2H), 6.81-6.73 (m, 2H), 3.38 (s, 1H), 2.88 (t, J=7.6 Hz, 2H), 2.80-2.71 (m, 1H), 2.66 (s, 3H), 2.61-2.55 (m, 1H), 2.49 (s, 6H), 2.44-2.38 (m, 2H), 2.30-2.15 (m, 5H), 2.07-1.93 (m, 4H), 1.09 (d, J=6.8 Hz, 3H), 0.42 (d, J=6.8 Hz, 3H).

Example 4. (1S,2S)-2-(2-((3-(4,7-Dimethyl-1H-benzo[d]imidazol-2-yl)propyl)(methyl)amino)ethyl)-6-fluoro-1-isopropyl-1,2,3,4-tetrahydronaphthalen-2-yl (2-(dimethylamino)ethyl)carbamate

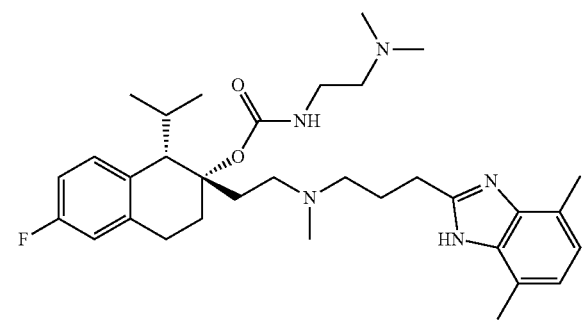 [SMILES: Cc1ccc(C)c2[nH]c(CCCN(C)CC[C@@]3(OC(=O)NCCN(C)C)CCc4cc(F)ccc4[C@@H]3C(C)C)nc12]

To a solution of (1S,2S)-2-(2-((3-(4,7-dimethyl-1H-benzo[d]imidazol-2-yl)propyl)(methyl)amino)ethyl)-6-fluoro-1-isopropyl-1,2,3,4-tetrahydronaphthalen-2-ol (Example 3, Step 1, 0.100 g, 0.222 mmol, 1 eq.) in DCM (1 mL) at 0° C. DIPEA (0.2 mL, 1.108 mmol, 5 eq.) and 4-nitrophenylchloroformate (0.111 g, 0.554 mmol, 2.5 eq.) were successively added. The solution was brought to rt and stirred for 3 h. The reaction mixture was then cooled to 0° C. and N,N-dimethylethylamine (0.024 g 0.333 mmol, 1.5 eq.) was added and the reaction mixture was stirred for 3 h at rt. The reaction mixture was then diluted with water (20 mL) and extracted with DCM. The combined organics were collected and dried over $Na_2SO_4$. The crude compound was purified by column chromatography on silica gel (230-400 mesh) using 20% MeOH in DCM as eluent to afford Example 4 (0.012 g, 10%). MS: 566.76 m/z (M+H)$^+$; $^1$H NMR: (400 MHz, $CD_3OD$) δ: 7.00 (dd, J=5.6, 8.0 Hz, 1H), 6.89 (s, 2H), 6.82 (td, J=2.8, 8.8 Hz, 1H), 6.76 (d, J=9.6 Hz, 1H), 3.39 (s, 1H), 3.22-3.17 (m, 2H), 2.94-2.53 (m, 6H), 2.49 (s, 6H), 2.46-2.29 (m, 5H), 2.22 (s, 3H), 2.21 (s, 6H), 2.07-1.96 (m, 4H), 1.76-1.70 (m, 1H), 1.09 (d, J=6.8 Hz, 3H), 1.01 (t, J=6.8 Hz, 3H), 0.41 (d, J=7.2 Hz, 3H).

Example 5. (1S,2S)-2-(2-((3-(4,7-Dimethoxy-1H-benzo[d]imidazol-2-yl)propyl)(methyl)amino)ethyl)-6-fluoro-1-isopropyl-1,2,3,4-tetrahydronaphthalen-2-yl methylcarbamate

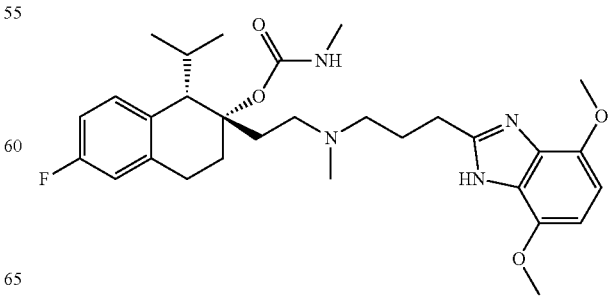

Step 1. (1S,2S)-2-(2-((3-(4,7-Dimethoxy-1H-benzo[d]imidazol-2-yl)propyl)(methyl)amino)ethyl)-6-fluoro-1-isopropyl-1,2,3,4-tetrahydronaphthalen-2-ol

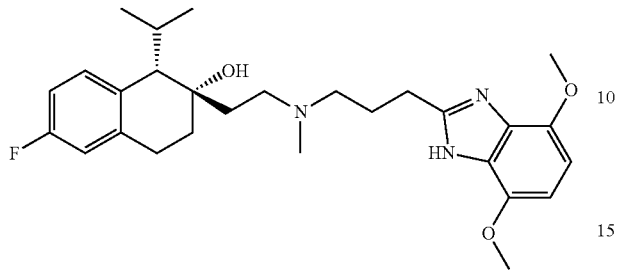

The title compound was prepared using a procedure similar to Example 3. To a solution of Intermediate 1 (0.6 g, 1.41 mmol, 1.0 eq.) in triethylamine (5 mL) was added compound 3-(4,7-dimethoxy-1H-benzo[d]imidazol-2-yl)-N-methylpropan-1-amine (0.4 g, 1.69 mmol, 1.2 eq.) at 0° C. The reaction mixture was stirred at 50° C. for 12 h. The solvents were evaporated and resulting residue was diluted with EtOAc and water. The organic layer was washed with brine, dried over sodium sulfate, and the solvents were then evaporated under reduced pressure. The resulting residue was purified by flash column chromatography to yield title alcohol (0.6 g, 84.05%) as a colorless liquid. MS: 484.5 m/z (M+H)$^+$.

Step 2. (1S,2S)-2-(2-((3-(4,7-Dimethoxy-1H-benzo[d]imidazol-2-yl)propyl)(methyl)amino)ethyl)-6-fluoro-1-isopropyl-1,2,3,4-tetrahydronaphthalen-2-yl methylcarbamate The alcohol from Step 1 (0.3 g, 0.62 mmol, 1.0 eq.) was dissolved in dry DCM (5 mL) and 4-nitrophenylchloroformate (0.12 g, 1.24 mmol, 2.0 eq.), followed by DIPEA (0.5 mL, 2.5 eq.) were added at 0° C. and the resulting mixture was stirred for 2 h. Next, methylamine in MeOH (2 mL, 2.0 eq.) was added to the reaction mixture at 0° C. The reaction mixture was warmed to rt and stirred for 1 h. The reaction mixture was quenched by water and extracted with ethyl acetate (60 mL×2). The combined organics were collected, washed with brine, dried over Na$_2$SO$_4$, and evaporated to dryness. The crude residue was purified by Prep HPLC to furnish pure Example 5 (0.052 g, 15%) as a white solid. MS: 541.5 m/z (M+H)$^+$ $^1$H NMR (400 MHz, CD$_3$OD) δ 7.03-7.00 (m, 1H), 7.84-6.74 (m, 2H), 6.61 (s, 2H), 3.92 (d, J=6.0 Hz, 6H), 3.39 (s, 1H), 2.96-2.71 (m, 4H), 2.67 (s, 3H), 2.66-2.60 (m, 1H), 2.59-2.46 (m, 3H), 2.43-2.40 (m, 1H), 2.31-2.19 (m, 4H), 2.17-2.07 (m, 2H), 2.05-1.91 (m, 1H), 1.77-1.74 (m, 1H), 0.91 (d, J=6.8 Hz, 3H), 0.42 (d, J=6.8 Hz, 3H).

Example 6. (1S,2S)-2-(2-((3-(4,7-Dimethoxy-1H-benzo[d]imidazol-2-yl)propyl)(methyl)amino)ethyl)-6-fluoro-1-isopropyl-1,2,3,4-tetrahydronaphthalen-2-yl (2-methoxyethyl)carbamate

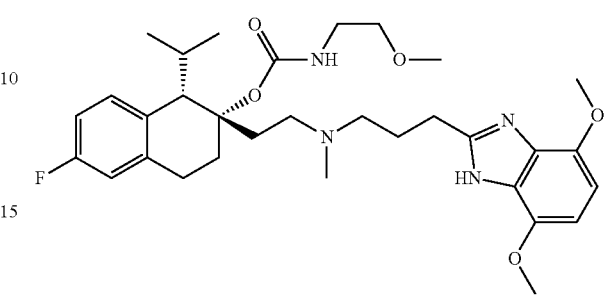

(1S,2S)-2-(2-((3-(4,7-dimethoxy-1H-benzo[d]imidazol-2-yl)propyl)(methyl)amino)ethyl)-6-fluoro-1-isopropyl-1,2,3,4-tetrahydronaphthalen-2-ol (Example 5, Step 1, 0.3 g, 0.62 mmol, 1.0 eq.) was dissolved in dry DCM (2.5 mL) and 4-nitrophenylchloroformate (0.27 g, 1.24 mmol, 2.0 eq.) followed by DIPEA (0.22 mL, 2.0 eq.) were added at 0° C. and stirred for 2 h. Next, methoxyethylamine in DCM (2 mL, 2.0 eq.) was added to the reaction mixture at 0° C. The reaction mixture was warmed to rt and stirred for 1 h. The reaction mixture was quenched by water and extracted with ethyl acetate. The combined organics were collected, washed with brine, dried over Na$_2$SO$_4$, and evaporated to dryness. The crude residue was purified by Prep HPLC to furnish pure Example 6 (0.07 g, 20.87%) as a white solid. MS: 585.6 m/z (M+H)$^+$ $^1$H NMR (400 MHz, CD$_3$OD) δ 7.00 (dd, J=6.0, 8.4 Hz, 1H), 6.84-6.75 (m, 2H), 6.61 (s, 2H), 3.90 (s, 6H), 3.42-3.38 (m, 3H), 3.34-3.32 (m, 3H), 3.25-3.20 (m, 2H), 2.95-2.86 (m, 1H), 2.86-2.82 (m, 2H), 2.79-2.73 (m, 1H), 2.60-2.54 (m, 1H), 2.49-2.40 (m, 3H), 2.26-2.18 (m, 4H), 2.07-2.02 (m, 2H), 1.98-1.90 (m, 2H), 1.74-1.67 (m, 1H), 1.09 (d, J=7.2 Hz, 3H), 0.42 (d, J=6.8 Hz, 3H).

Example 7. (1S,2S)-2-(2-((3-(7-Chloro-4-methoxy-1H-benzo[d]imidazol-2-yl)propyl)(methyl)amino)ethyl)-6-fluoro-1-isopropyl-1,2,3,4-tetrahydronaphthalen-2-yl dimethylcarbamate

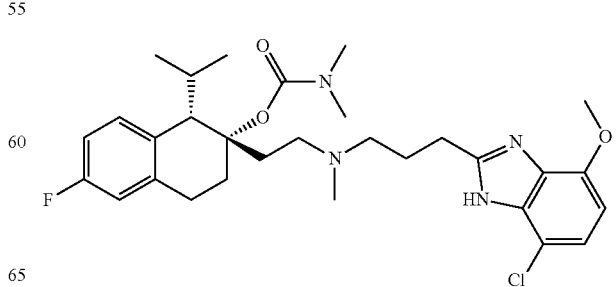

Step 1. (1S,2S)-2-(2-((3-(7-Chloro-4-methoxy-1H-benzo[d]imidazol-2-yl)propyl)(methyl)amino)ethyl)-6-fluoro-1-isopropyl-1,2,3,4-tetrahydronaphthalen-2-ol

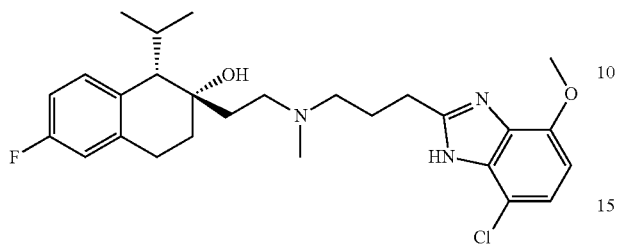

The title compound was prepared using a procedure similar to Example 3. A solution of Intermediate 1 (0.5 g, 1.23 mmol, 1.0 eq.) and 3-(7-chloro-4-methoxy-1H-benzo[d]imidazol-2-yl)-N-methylpropan-1-amine (0.374 g 1.48 mmol, 1.2 eq.) in triethylamine (2.5 mL) and MeCN (2.5 mL) was stirred at 60° C. for 12 h. The reaction mixture was quenched with water (25 mL) and extracted in DCM (25 mL×3). The combined organics were collected, washed with brine, dried over $Na_2SO_4$ and evaporated to dryness. The crude compound was purified on a COMBIFLASH® column by using 4-5% MeOH in DCM as eluent to afford alcohol (0.25 g 42%). MS: 488.4 m/z $(M+H)^+$

Step 2. (1S,2S)-2-(2-((3-(7-Chloro-4-methoxy-1H-benzo[d]imidazol-2-yl)propyl)(methyl)amino)ethyl)-6-fluoro-1-isopropyl-1,2,3,4-tetrahydronaphthalen-2-yl dimethylcarbamate To a solution of the alcohol product from Step 1 (0.250 g, 0.513 mmol, 1 eq.) in DCM at 0° C., DIPEA (0.3 mL, 2.56 mmol, 5 eq.) and 4-nitrophenylchloroformate (0.330 g, 1.79 mmol, 3.5 eq.) were successively added. The solution was brought to rt and stirred for 3 h. The reaction mixture was then cooled to 0° C. and N,N-dimethylamine in MeOH (2.5 mL, 10 vol.) was added and the reaction mixture was stirred for 3 h at rt. The reaction mixture was diluted with water (20 mL) and extracted with DCM (3×20 mL) dried over $Na_2SO_4$, and concentrated. The crude compound was purified by column chromatography on silica gel (100-200 mesh) using 3-4% MeOH in DCM as eluent to afford Example 7 (0.050 g, 18%). MS: 559.7 m/z $(M+H)^+$; $^1H$ NMR: (400 MHz, $CD_3OD$) δ: 7.13 (d, J=8.4 Hz, 1H), 7.01 (dd, J=5.6, 8.4 Hz, 1H), 6.84-6.76 (m, 2H), 6.72 (d, J=8.4 Hz, 1H), 3.96 (s, 3H), 3.40 (s, 1H), 2.98-2.86 (m, 10H), 2.67-2.56 (m, 1H), 2.45-2.23 (m, 4H), 2.20 (s, 3H), 2.18-1.76 (m, 6H), 1.08 (d, J=7.2 Hz, 3H), 0.42 (d, J=6.8 Hz, 3H).

Example 8. (1S,2S)-2-(2-((3-(4,6-Bis(trifluoromethyl)-1H-benzo[d]imidazol-2-yl)propyl)(methyl)amino)ethyl)-6-fluoro-1-isopropyl-1,2,3,4-tetrahydronaphthalen-2-yl morpholine-4-carboxylate

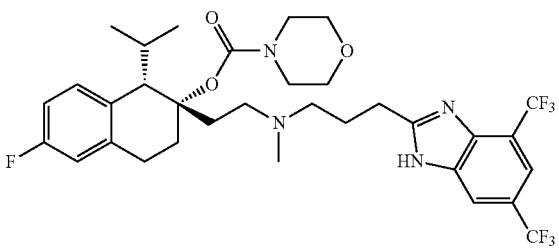 [SMILES: CC(C)[C@H]1c2ccc(F)cc2CC[C@@]1(CCN(C)CCCc1nc2c(C(F)(F)F)cc(C(F)(F)F)cc2[nH]1)OC(=O)N1CCOCC1]

Step 1. (1S,2S)-2-(2-((3-(4,6-Bis(trifluoromethyl)-1H-benzo[d]imidazol-2-yl)propyl)(methyl)amino)ethyl)-6-fluoro-1-isopropyl-1,2,3,4-tetrahydronaphthalen-2-ol

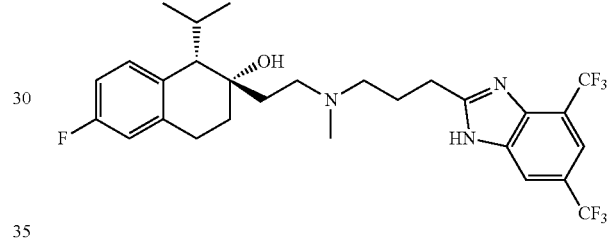

The title compound was prepared using a procedure similar to Example 3. A solution of Intermediate 1 (0.2 g, 0.492 mmol, 1.0 eq.) and 3-(4,6-bis(trifluoromethyl)-1H-benzo[d]imidazol-2-yl)-N-methylpropan-1-amine (0.147 g 0.563 mmol, 1.2 eq.) in triethylamine (1 mL) and MeCN (2 mL) was stirred at 60° C. for 12 h. The reaction mixture was quenched with water (20 mL) and extracted in DCM (20 mL×3). The combined organics were collected, washed with brine, dried over $Na_2SO_4$, and evaporated to dryness. The crude compound was purified on a COMBIFLASH® column using 4-5% MeOH in DCM as eluent to afford the title alcohol (0.1 g 36%). MS: 560.3 m/z $(M+H)^+$.

Step 2. (1S,2S)-2-(2-((3-(4,6-Bis(trifluoromethyl)-1H-benzo[d]imidazol-2-yl)propyl)(methyl)amino)ethyl)-6-fluoro-1-isopropyl-1,2,3,4-tetrahydronaphthalen-2-yl morpholine-4-carboxylate To a solution of the alcohol product from Step 1 (0.075 g, 0.134 mmol, 1 eq.) in DCM at 0° C., DIPEA (0.1 mL, 0.67 mmol, 5 eq.) and 4-nitrophenylchloroformate (0.067 g, 0.335 mmol, 2.5 eq.) were successively added. The solution was brought to rt and stirred for 3 h. The reaction mixture was then cooled to 0° C. and morpholine (0.06 mL, 0.067 mmol, 5 eq.) was added and stirred for 3 h at rt. The reaction mixture was diluted with water (15 mL) and extracted with DCM. The combined organic layers were dried over $Na_2SO_4$ and then concentrated. The crude compound was purified by preparative TLC using 10% MeOH in DCM as mobile phase to afford Example 8 (0.025 g, 25%). MS: 673.4 m/z $(M+H)^+$; 1H NMR: (400 MHz, $CD_3OD$) δ: 8.09 (s, 1H), 7.78 (s, 1H), 7.00 (dd, J=6.0, 7.6 Hz, 1H), 6.84-6.79 (m, 2H), 3.65-3.60 (m, 4H), 3.47-3.40 (m, 4H), 3.03 (t, J=7.2 Hz, 2H), 2.96 (bs, 1H), 2.88-2.76 (m, 2H), 2.66-2.63 (m, 3H), 2.38 (s, 3H), 2.33 (bs, 1H), 2.12-2.05 (m, 5H), 1.86-1.78 (m, 1H), 1.09 (d, J=6.8 Hz, 3H), 0.43 (d, J=7.2 Hz, 3H).

Example 9. (1S,2S)-2-(2-((3-(1H-Benzo[d]imidazol-2-yl)-3-methylbutyl)(methyl)amino)ethyl)-6-fluoro-1-isopropyl-1,2,3,4-tetrahydronaphthalen-2-yl morpholine-4-carboxylate

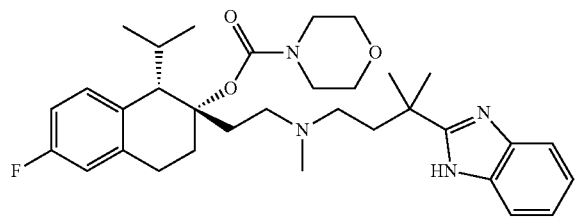 [SMILES: CC(C)[C@H]1c2ccc(F)cc2CC[C@@]1(CCN(C)CCC(C)(C)c1nc2ccccc2[nH]1)OC(=O)N1CCOCC1]

Step 1. (1S,2S)-2-(2-((3-(1H-Benzo[d]imidazol-2-yl)-3-methylbutyl)(methyl)amino)ethyl)-6-fluoro-1-isopropyl-1,2,3,4-tetrahydronaphthalen-2-ol

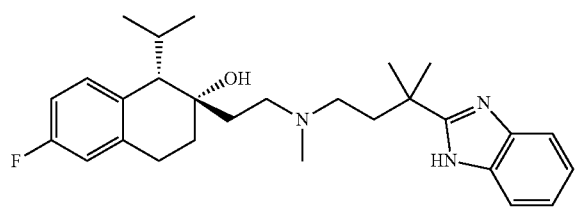 [SMILES: CC(C)[C@H]1c2ccc(F)cc2CC[C@]1(O)CCN(C)CCC(C)(C)c1nc2ccccc2[nH]1]

The title compound was prepared using a procedure similar to Example 3. To a solution of Intermediate 2 (0.365 g, 1.8 mmol, 1.2 eq.) and Intermediate 3 (0.4 g, 1.51 mmol, 1.0 eq.) in DCM was added sodium triacetoxyborohydride (STAB, 1.01 g, 4.53 mmol, 3.0 eq.) portionwise at 0° C. and the reaction mixture was stirred for 2 h. The reaction was quenched with water and diluted with DCM. The aqueous layer was extracted with DCM, dried over Na$_2$SO$_4$, and concentrated in vacuo. The resulting residue was purified by column chromatography on silica gel using DCM/MeOH. The reaction mixture was warmed to rt and stirred for 2 h. The reaction was diluted with DCM and water was added (40 mL). The organic layer was washed with brine, dried over Na$_2$SO$_4$, and evaporated to dryness. The crude material was purified by column chromatography using DCM/MeOH as the eluent to produce the desired alcohol (0.42 g, 47%) as a white solid. MS: 452.4 m/z (M+H)$^+$.

Step 2. (1S,2S)-2-(2-((3-(1H-Benzo[d]imidazol-2-yl)-3-methylbutyl)(methyl)amino)ethyl)-6-fluoro-1-isopropyl-1,2,3,4-tetrahydronaphthalen-2-yl morpholine-4-carboxylate To a solution of alcohol product from Step 1 (0.28 g, 0.620 mmol, 1 eq.) in DCM at 0° C., DIPEA (0.4 mL, 2.172 mmol, 3.50 eq.) and 4-nitrophenylchloroformate (0.310 g, 1.55 mmol, 2.5 eq.) were added. The resulting solution was stirred for 3 h at rt then morpholine (0.002 mL, 2.172 mmol, 3.5 eq.) was added at 0° C. and the mixture was stirred for 3 h at rt. The reaction mixture was diluted with water and extracted with DCM. The combined organic layer was then dried over Na$_2$SO$_4$ and concentrated. The crude compound was purified by Combiflash chromatography using 7-8% MeOH in DCM as eluent to afford pure Example 9 (10 mg, 3%). MS: 565.86 m/z (M+H)$^+$; $^1$H NMR (CD$_3$OD): δ 7.68 (d, J=7.6 Hz, 1H), 7.47-7.34 (m, 3H), 6.98 (t, J=7.6 Hz, 1H), 6.84-6.78 (m, 2H), 3.95-3.84 (m, 4H), 3.68-3.57 (m, 4H), 3.21 (bs, 2H), 3.10-2.70 (m, 5H), 2.54 (m, 6H), 2.39-1.92 (m, 4H), 1.73-1.47 (m, 11H), 1.30 (s, 6H), 1.15-1.06 (m, 3H), 0.45-0.40 (m, 3H).

Example 10. (1S,2S)-2-(2-((3-(1H-Benzo[d]imidazol-2-yl)-3-methylbutyl)(methyl)amino)ethyl)-6-fluoro-1-isopropyl-1,2,3,4-tetrahydronaphthalen-2-yl methylcarbamate

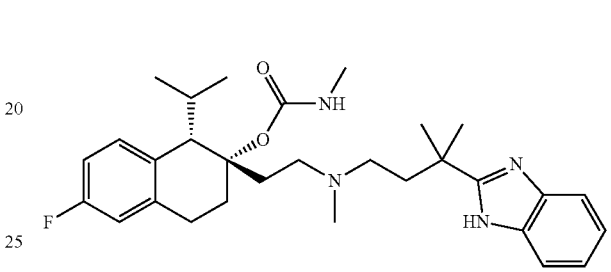

To a solution of (1S,2S)-2-(2-((3-(1H-benzo[d]imidazol-2-yl)-3-methylbutyl)(methyl)amino)ethyl)-6-fluoro-1-isopropyl-1,2,3,4-tetrahydronaphthalen-2-ol (Example 9, Step 1, 0.3 g, 0.665 mmol, 1 eq.) in DCM at 0° C., DIPEA (0.4 mL, 2.328 mmol, 3.5 eq.) and 4-nitrophenylchloroformate (0.334 g, 1.662 mmol, 2.5 eq.) were successively added. The solution was brought to rt and stirred for 3 h. The reaction mixture was then cooled to 0° C. and methyl amine in MeOH (10 vol.) was added. The reaction mixture was brought to rt and stirred for 6 h. The reaction mixture was diluted with water (30 mL) and extracted with DCM (30 mL×2). The combined organic layer was dried over Na$_2$SO$_4$ and concentrated. The crude compound was purified by Combiflash chromatography using 7-8% MeOH in DCM as eluent to afford Example 10. MS: 509.8 m/z (M+H)$^+$; $^1$H NMR (CD$_3$OD): δ 7.48 (dd, J=3.2, 6.0 Hz, 2H), 7.22 (dd, J=3.2, 6.0 Hz, 2H), 6.99 (dd, J=6.0, 8.0 Hz, 1H), 6.82 (td, J=2.4, 8.4 Hz, 1H), 6.74 (d, J=9.6 Hz, 1H), 2.93-2.70 (m, 4H), 2.67 (s, 3H), 2.59 (bs, 2H), 2.36 (s, 3H), 2.35-1.77 (m, 7H), 1.47 (s, 6H), 1.09 (d, J=6.8 Hz, 3H), 0.41 (d, J=6.8 Hz, 3H).

Example 11. (1S,2S)-2-(2-((3-(1H-Benzo[d]imidazol-2-yl)-3-methylbutyl)(methyl)amino)ethyl)-6-fluoro-1-isopropyl-1,2,3,4-tetrahydronaphthalen-2-yl (2-(dimethylamino)ethyl)carbamate

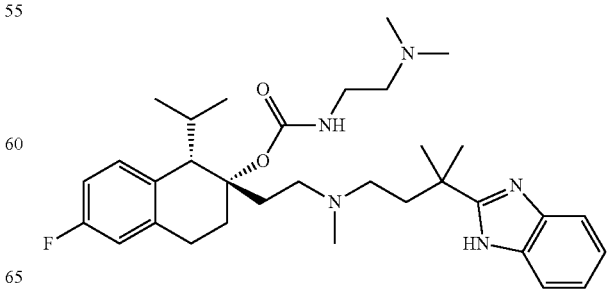

To a solution of (1S,2S)-2-(2-((3-(1H-benzo[d]imidazol-2-yl)-3-methylbutyl)(methyl)amino)ethyl)-6-fluoro-1-isopropyl-1,2,3,4-tetrahydronaphthalen-2-ol (Example 9, Step 1, 0.120 g, 0.266 mmol, 1 eq.) in DCM (1.2 ml) at 0° C., DIPEA (0.1 mL, 0.532 mmol, 2 eq.) and 4-nitrophenylchloroformate (0.160 g, 0.798 mmol, 3 eq.) were successively added. The solution was brought to rt and stirred for 3 h. The reaction mixture was then cooled to 0° C. and N',N'-dimethylethane-1,2-diamine (0.93 g, 1.064 mmol, 4 eq.) was added and stirred for 9 h at rt. The reaction mixture was diluted with water (20 mL) and extracted with DCM. The organic layer was dried over Na$_2$SO$_4$, concentrated, and the crude compound was purified by COMBIFLASH® using 3-3.4% MeOH in DCM as eluent to afford Example 11 (0.050 g, 34%). MS: 566.3 m/z (M+H)$^+$; $^1$H NMR (CD$_3$OD): δ 7.52 (dd, J=3.2, 5.6 Hz, 2H), 7.22 (dd, J=3.2, 6.0 Hz, 2H), 6.98 (dd, J=6.0, 8.4 Hz, 1H), 6.83-6.76 (m, 2H), 3.36 (s, 1H), 2.93-2.48 (m, 3H), 2.41 (t, J=6.8 Hz, 3H), 2.23-1.89 (m, 16H), 1.70-1.62 (m, 1H), 1.46 (s, 6H), 1.09 (d, J=7.2 Hz, 3H), 0.41 (d, J=6.8 Hz, 3H).

Example 12. (1S,2S)-2-(2-((3-(1H-Benzo[d]imidazol-2-yl)-3-methylbutyl)(methyl)amino)ethyl)-6-fluoro-1-isopropyl-1,2,3,4-tetrahydronaphthalen-2-yl (2-methoxyethyl)carbamate

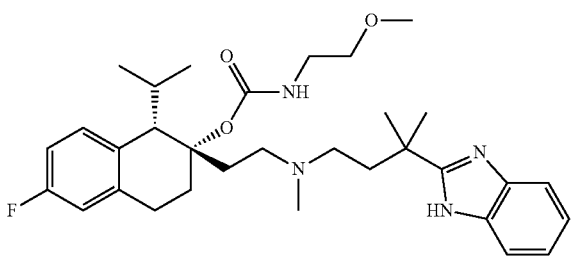 [SMILES: COCCNC(=O)O[C@]1(CCN(C)CCC(C)(C)c2nc3ccccc3[nH]2)CCc2cc(F)ccc2[C@@H]1C(C)C]

To a solution of (1S,2S)-2-(2-((3-(1H-benzo[d]imidazol-2-yl)-3-methylbutyl)(methyl)amino)ethyl)-6-fluoro-1-isopropyl-1,2,3,4-tetrahydronaphthalen-2-ol (Example 9, Step 1, 0.4 g, 0.88 mmol, 1.0 eq.) in DCM at 0° C., DIPEA (0.5 mL 3.10 mmol 3.5 eq.) and 4-nitrophenylchloroformate (0445 g 2.21 mmol, 2.5 eq.) were added. The solution was stirred for 3 h then 2-methyoxyethylamine was added at 0° C. and the mixture was stirred for 3 hours at rt. The reaction mixture was diluted with water (10 mL) and extracted with DCM (3×20 mL). The combined organic layer was dried over Na$_2$SO$_4$ and concentrated. The crude compound was purified by Combiflash chromatography using 2.6-3% MeOH in DCM as eluent to afford Example 12 (50 mg, 10%). MS: 553.4 m/z (M+H)$^+$; $^1$H NMR (CD$_3$OD): δ 7.48 (dd, J=3.2, 6.0 Hz, 2H), 7.22 (dd, J=3.2, 6.0 Hz, 2H), 6.98 (t, J=6.0 Hz, 1H), 6.82 (d, J=2.4, 8.4 Hz, 1H), 6.74 (d, J=9.6 Hz, 1H), 3.42-3.23 (m, 7H), 2.6-3.0 (m, 6H), 2.44 (bs, 3H), 2.4-2.0 (m, 6H), 1.49-1.46 (m, 9H), 1.08 (d, J=6.8 Hz, 3H), 0.42 (d, J=6.8 Hz, 3H).

Example 13. (1S,2S)-2-(2-((3-(1H-Benzo[d]imidazol-2-yl)-3-methylbutyl)(methyl)amino)ethyl)-6-fluoro-1-isopropyl-1,2,3,4-tetrahydronaphthalen-2-yl (2-(pyrrolidin-1-yl)ethyl)carbamate

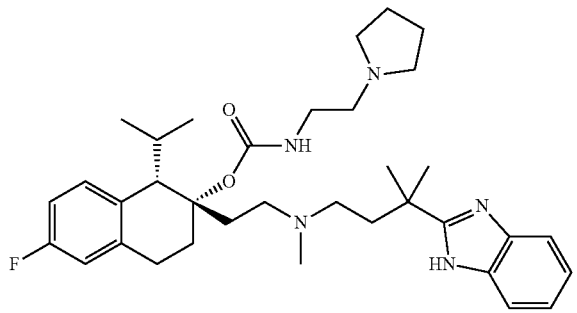 [SMILES: CC(C)[C@H]1c2ccc(F)cc2CC[C@@]1(CCN(C)CCC(C)(C)c1nc2ccccc2[nH]1)OC(=O)NCCN1CCCC1]

To a solution of (1S,2S)-2-(2-((3-(1H-benzo[d]imidazol-2-yl)-3-methylbutyl)(methyl)amino)ethyl)-6-fluoro-1-isopropyl-1,2,3,4-tetrahydronaphthalen-2-ol (Example 9, Step 1, 0.080 g, 0.177 mmol, 1 eq.) in DCM at 0° C., DIPEA (0.2 mL, 0.88 mmol, 5 eq.) and 4-nitrophenylchloroformate (2.0 g, 0.443 mmol, 2.5 eq.) were successively added. The solution was brought to rt and stirred for 2 h. The reaction mixture was then cooled to 0° C. and 2-(pyrrolidin-1-yl)ethan-1-amine (0.040 g, 0.443 mmol, 2.5 eq.) was added and the mixture was stirred for 2 h at rt. The reaction mixture was diluted with water (15 mL) and extracted with DCM. The combined organic layer was dried over Na$_2$SO$_4$ and then concentrated. The crude compound was purified by preparative TLC using 10% MeOH in DCM as mobile phase to afford Example 13 (0.020 g, 19%). MS: 592.4 m/z (M+H)$^+$; $^1$H NMR: (400 MHz, CD$_3$OD) δ: 7.50 (dd, J=3.2, 6.0 Hz, 2H), 7.22 (dd, J=3.2, 6.0 Hz, 2H), 6.99 (dd, J=6.0, 8.4 Hz, 1H), 6.84-6.75 (m, 2H), 3.25 (t, J=6.8 Hz, 1H), 2.95-2.90 (m, 1H), 2.77-66 (m, 6H), 2.45-2.43 (m, 1H), 2.29 (s, 3H), 2.20-1.92 (m, 4H), 1.83 (bs, 4H), 1.47 (d, J=2.8 Hz, 6H), 1.09 (d, J=6.8 Hz, 3H), 0.42 (d, J=6.8 Hz, 3H).

Example 14. (1S,2S)-2-(2-((3-(1H-Benzo[d]imidazol-2-yl)-3-methylbutyl)(methyl)amino)ethyl)-6-fluoro-1-isopropyl-1,2,3,4-tetrahydronaphthalen-2-yl (2-(diethylamino)ethyl)carbamate

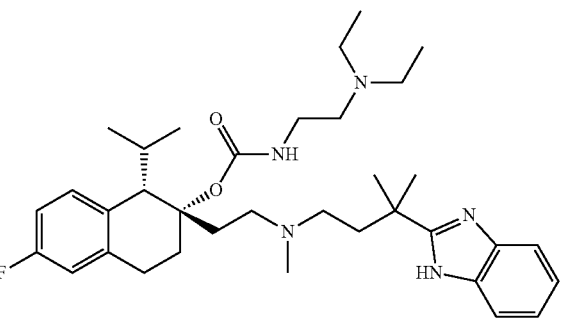 [SMILES: CCN(CC)CCNC(=O)O[C@]1(CCN(C)CCC(C)(C)c2nc3ccccc3[nH]2)CCc2cc(F)ccc2[C@@H]1C(C)C]

To a solution of (1S,2S)-2-(2-((3-(1H-benzo[d]imidazol-2-yl)-3-methylbutyl)(methyl)amino)ethyl)-6-fluoro-1-isopropyl-1,2,3,4-tetrahydronaphthalen-2-ol (Example 9, Step 1, 0.060 g, 0.133 mmol, 1 eq.) in DCM at 0° C., DIPEA (0.1 mL, 0.66 mmol, 5 eq.) and 4-nitrophenylchloroformate (2.0 g, 0.332 mmol, 2.5 eq.) were successively added. The solution was brought to rt and stirred for 2 h. The reaction mixture was then cooled to 0° C. and N1,N1-diethylethane-1,2-diamine (0.040 g, 0.332 mmol, 2.5 eq.) was added and stirred for 2 h at rt. The reaction mixture was diluted with water (15 mL) and extracted with DCM. Combined organic layer was dried over Na$_2$SO$_4$ and then concentrated. The crude compound was purified by preparative TLC using 10% MeOH in DCM as mobile phase to afford Example 14 (0.025 g, 32%). MS: 594.4 m/z (M+H)$^+$; $^1$H NMR: (400 MHz, CD$_3$OD) δ: 7.49 (dd, J=3.2, 5.6 Hz, 2H), 7.22 (dd, J=3.2, 5.6 Hz, 2H), 6.99 (t, J=8.0 Hz, 1H), 6.82-6.75 (m, 2H), 3.36 (s, 1H), 3.23-3.20 (m, 2H), 2.95-2.90 (m, 1H), 2.74-67 (m, 7H), 2.46 (m, 1H), 2.31 (s, 3H), 2.17 (m, 1H), 2.05-1.99 (m, 6H), 1.47 (s, 3H), 1.30 (s, 3H), 1.09 (bs, 9H), 0.42 (d, J=6.8 Hz, 3H).

Example 15. (1S,2S)-2-(2-((3-(4,7-Dimethyl-1H-benzo[d]imidazol-2-yl)propyl)(methyl)amino)ethyl)-6-fluoro-1-isopropyl-1,2,3,4-tetrahydronaphthalen-2-yl morpholine-4-carboxylate

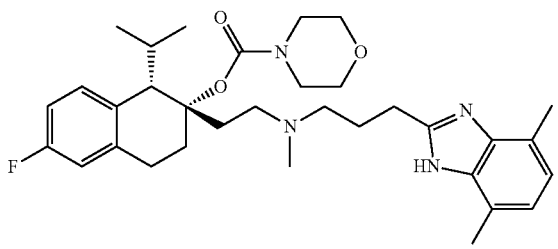 [SMILES: Cc1ccc(C)c2[nH]c(CCCN(C)CC[C@@]3(OC(=O)N4CCOCC4)CCc4cc(F)ccc4[C@@H]3C(C)C)nc12]

Step 1. Methyl 4-((2-((1S,2S)-6-fluoro-2-hydroxy-1-isopropyl-1,2,3,4-tetrahydronaphthalen-2-yl)ethyl)(methyl)amino)butanoate

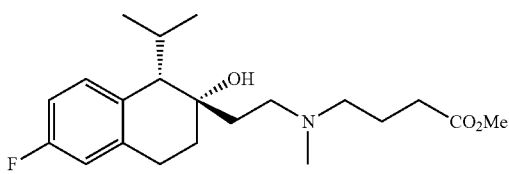 [SMILES: COC(=O)CCCN(C)CC[C@@]1(O)CCc2cc(F)ccc2[C@@H]1C(C)C]

To a solution of (1S,2S)-6-fluoro-1-isopropyl-2-(2-(methylamino)ethyl)-1,2,3,4-tetrahydronaphthalen-2-ol (11.5 g, 43.39 mmol, 1 eq.) in a mixture of MeCN (230 mL) and triethylamine (26.3 mL, 216.98 mmol, 5 eq.) was added methyl-4-butyrate (9.20 g, 52.07 mmol, 1.2 eq.) and KI (3.6 g, 21.69 mmol 0.5 eq.). The reaction mixture was stirred at 60° C. for 12 hours. The reaction mixture was then diluted with water (500 mL) and extracted with DCM. The combined organic layer was then dried over Na$_2$SO$_4$ and concentrated. The crude compound was purified by column chromatography on silica gel (230-400 mesh) using 2.1-2.5% MeOH in DCM as eluent to afford methyl 4-((2-((1S,2S)-6-fluoro-2-hydroxy-1-isopropyl-1,2,3,4-tetrahydronaphthalen-2-yl)ethyl)(methyl)amino)butanoate (12.0 g, 75%). MS: 366.2 m/z (M+H)$^+$ Step 2. (1S,2S)-6-Fluoro-1-isopropyl-2-(2(4-methoxy-4-oxobutyl)(methyl)amino)ethyl)-1,2,3,4-tetrahydronaphthalen-2-yl morpholine-4-carboxylate

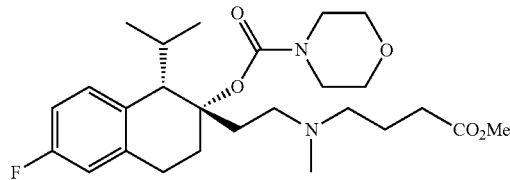 [SMILES: COC(=O)CCCN(C)CC[C@@]1(OC(=O)N2CCOCC2)CCc2cc(F)ccc2[C@@H]1C(C)C]

To a solution of methyl 4-((2-((1S,2S)-6-fluoro-2-hydroxy-1-isopropyl-1,2,3,4-tetrahydronaphthalen-2-yl)ethyl)(methyl)amino)butanoate (11.5 g, 31.50 mmol, 1 eq.) in DCM (115 mL) at 0° C., DIPEA (26.91 mL, 157.53 mmol, 5 eq.) and 4-nitrophenylchloroformate (15.83 g, 78.76 mmol, 2.5 eq.) were successively added. The solution was brought to rt and stirred for 3 h. The reaction mixture was then cooled to 0° C. and morpholine (27.52 mL, 315.06 mmol, 10 eq.) was added and stirred for 3 h at rt. The reaction mixture was diluted with water (150 mL) and extracted with DCM (2×150 mL). The organic layer was dried over Na$_2$SO$_4$ and concentrated. The crude compound was purified on a COMBIFLASH® column using 2.6-3% MeOH in DCM as eluent to afford (1S,2S)-6-fluoro-1-isopropyl-2-(2-((4-methoxy-4-oxobutyl)(methyl)amino)ethyl)-1,2,3,4-tetrahydronaphthalen-2-yl morpholine-4-carboxylate (11.0 g, 70%). MS: 479.4 m/z (M+H)$^+$ Step 3. 4-((2-((1S,2S)-6-Fluoro-1-isopropyl-2-((morpholine-4-carbonyl)oxy)-1,2,3,4-tetrahydronaphthalen-2-yl)ethyl)(methyl)amino)butanoic acid

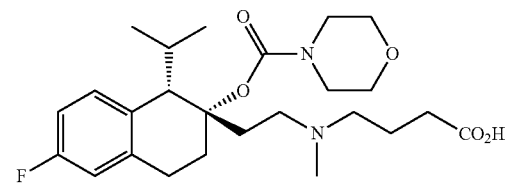 [SMILES: CC(C)[C@H]1c2ccc(F)cc2CC[C@@]1(CCN(C)CCCC(=O)O)OC(=O)N1CCOCC1]

To a solution of (1S,2S)-6-fluoro-1-isopropyl-2-(2-((4-methoxy-4-oxobutyl)(methyl)amino)ethyl)-1,2,3,4-tetrahydronaphthalen-2-yl morpholine-4-carboxylate (11.0 g, 23.01 mmol, 1 eq.) in THF (55.0 mL) and H$_2$O (55.0 mL), LiOH (1.65 g, 69.03 mmol, 3 eq.) was added and the reaction mixture was stirred for 2 h at rt. The reaction mixture was diluted with saturated solution of citric acid to an acidic pH and then extracted with 10% MeOH in DCM. The combined organic layer was dried over Na$_2$SO$_4$ and concentrated to obtain 4-((2-((1S,2S)-6-fluoro-1-isopropyl-2-((morpholine-4-carbonyl)oxy)-1,2,3,4-tetrahydronaphthalen-2-yl)ethyl)(methyl)amino)butanoic acid (95 g, 89%). MS: 465.7 m/z (M+H)$^+$.

Step 4. (1S,2S)-2-(2-((3-(4,7-Dimethyl-1H-benzo[d]imidazol-2-yl)propyl)(methyl)amino)ethyl)-6-fluoro-1-isopropyl-1,2,3,4-tetrahydronaphthalen-2-yl morpholine-4-carboxylate To a cooled solution of 4-((2-((1S,2S)-6-fluoro-1-isopropyl-2-((morpholine-4-carbonyl)oxy)-1,2,3,4-tetrahydronaphthalen-2-yl)ethyl)(methyl)amino)butanoic acid (9.5 g, 20.47 mmol, 1 eq.) in DMF (95.0 mL) at 0° C., HATU (9.33 g, 24.56 mmol, 1.2 eq.) was added and stirred for 30 minutes at 0° C. under N2 atmosphere. 1,2-Benzendiamine, 3,6-dimethyl (3.89 g, 28.66 mmol, 1.4 eq.) and DIPEA (8.7 mL, 51.18 mmol, 2.5 eq.) were added and the reaction mixture was brought to rt and stirred for 12 h. The reaction mixture was diluted with water (1 L) and extracted with DCM. The combined organic layer was washed with cold water (1000 mL×2), dried over $Na_2SO_4$ and concentrated to obtain crude amide (90 g, 75%). MS: 583.4 m/z $(M+H)^+$.

To a mixture of above crude amide (9.0 g, 15.46 mmol, 1 eq.) and PPTS (0.778 g, 3.1 mmol, 0.2 eq.) in toluene (270 mL) was heated at reflux over Dean-Stark apparatus for 4 h. The reaction mixture was concentrated under reduced pressure the residue was diluted with sat. $NaHCO_3$(250 mL) and extracted with DCM. The combined organic layer was dried over $Na_2SO_4$ and concentrated under reduced pressure. The residue was purified by column chromatography using 2.9-3.2% MeOH in DCM as eluent to obtain Example 15 6.2 g, 71%). MS: 565.4 m/z $(M+H)^+$.

To a mixture of Example 15 (6.0 g, 10.61 mmol, 1 eq.) in DCM (60.0 mL) at 0° C., (2.54 mL, 12.74 mmol, 1.2 eq.), 5 molar HCl in dioxane was added and the mixture was stirred for 1 h at rt. The reaction mixture was concentrated under reduced pressure to give residue which was triturated with diethyl ether to give Example 15-HCl salt (6.0 g) as a colorless powder. MS: 565.4 m/z $(M+H)^+$; $^1H$ NMR: (400 MHz, $CD_3OD$) δ: 7.24 (s, 2H), 7.03 (dd, J=6.4, 8.4 Hz, 1H), 6.88-6.85 (m, 2H), 3.67-3.38 (m, 9H), 3.28-2.93 (m, 7H), 2.86 (s, 3H), 2.61-2.55 (m, 7H), 2.36-2.34 (m, 2H), 2.15-1.97 (m, 4H), 1.10 (d, J=7.2 Hz, 3H), 0.44 (d, J=6.8 Hz, 3H).

Example 16. (1S,2S)-2-(2-((3-(4,7-dimethyl-1H-benzo[d]imidazol-2-yl)propyl)(methyl)amino)ethyl)-6-fluoro-1-isopropyl-1,2,3,4-tetrahydronaphthalen-2-yl dimethylcarbamate

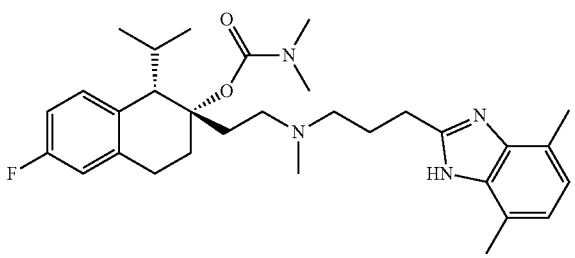 [SMILES: Cc1ccc(C)c2[nH]c(CCCN(C)CC[C@@]3(OC(=O)N(C)C)CCc4cc(F)ccc4[C@@H]3C(C)C)nc12]

Step 1. Methyl 4-((2-(((1S,2S)-2-((dimethylcarbamoyl)oxy)-6-fluoro-1-isopropyl-1,2,3,4-tetrahydronaphthalen-2-yl)ethyl)(methyl)amino)butanoate

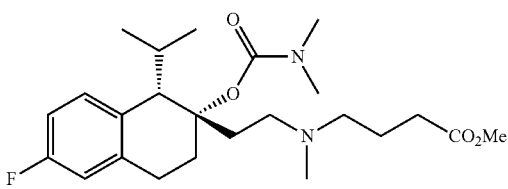 [SMILES: COC(=O)CCCN(C)CC[C@@]1(OC(=O)N(C)C)CCc2cc(F)ccc2[C@@H]1C(C)C]

To a solution of methyl 4-((2-(((1S,2S)-6-fluoro-2-hydroxy-1-isopropyl-1,2,3,4-tetrahydronaphthalen-2-yl)ethyl)(methyl)amino)butanoate (Example 15, Step 1, 0.3 g, 0.828 mmol, 1 eq.) in DCM (3 mL) at 0° C., DIPEA (0.7 mL, 4.14 mmol, 5 eq.) and 4-nitrophenylchloroformate (0.416 g, 2.07 mmol, 2.5 eq.) were successively added. The solution was brought to rt and stirred for 3 h. The reaction mixture was then cooled to 0° C. and dimethyl amine in MeOH (3 mL) was added and the mixture was stirred for 3 h at rt. The reaction mixture was diluted with water (20 mL) and extracted with DCM. The organic layer was dried over $Na_2SO_4$ and concentrated. The crude compound was purified by Combiflash chromatography using 4-5% MeOH in DCM as eluent to afford methyl 4-((2-(((1S,2S)-2-((dimethylcarbamoyl)oxy)-6-fluoro-1-isopropyl-1,2,3,4-tetrahydronaphthalen-2-yl)ethyl)(methyl)amino)butanoate (0.190 g, 53%). MS: 437.7 m/z $(M+H)^+$ Step 2. 4-((2-(((1S,2S)-2-((Dimethylcarbamoyl)oxy)-6-fluoro-1-isopropyl-1,2,3,4-tetrahydronaphthalen-2-yl)ethyl)(methyl)amino)butanoic acid

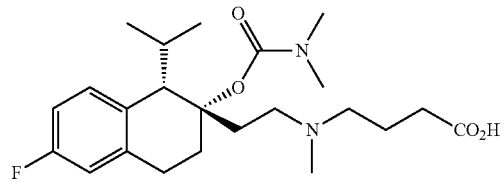 [SMILES: CC(C)[C@H]1c2ccc(F)cc2CC[C@@]1(CCN(C)CCCC(=O)O)OC(=O)N(C)C]

To a solution of methyl 4-((2-(((1S,2S)-2-((dimethylcarbamoyl)oxy)-6-fluoro-1-isopropyl-1,2,3,4-tetrahydronaphthalen-2-yl)ethyl)(methyl)amino)butanoate (0.180 g, 0.412 mmol, 1 eq.) in THF (1 mL) and $H_2O$ (1 mL), LiOH (0.052 g, 1.23 mmol, 3 eq.) was added and the mixture was stirred for 2 h at rt. The reaction mixture was diluted with saturated solution of citric acid to an acidic pH and extracted with 10% MeOH in DCM. The combined organic layer was dried over $Na_2SO_4$ and concentrated to obtain 4-((2-(((1S,2S)-2-((dimethylcarbamoyl)oxy)-6-fluoro-1-isopropyl-1,2,3,4-tetrahydronaphthalen-2-yl)ethyl)(methyl)amino)butanoic acid (0.140 g, 80%). MS: 421.6 m/z $(M-H)^-$.

Step 3. (1S,2S)-2-(2-((3-(4,7-Dimethyl-1H-benzo[d]imidazol-2-yl)propyl)(methyl)amino)ethyl)-6-fluoro-1-isopropyl-1,2,3,4-tetrahydronaphthalen-2-yl dimethylcarbamate To a cooled solution of 4-((2-(((1S,2S)-2-((dimethylcarbamoyl)oxy)-6-fluoro-1-isopropyl-1,2,3,4-tetrahydronaphthalen-2-yl)ethyl)(methyl)amino)butanoic acid (0.130 g, 0.307 mmol, 1 eq.) in DMF (1.5 mL) at 0° C., HATU (0.140 g, 0.368 mmol, 1.2 eq.) was added and the mixture was stirred for 30 minutes at 0° C. under N2 atmosphere. 1,2-Benzendiamine, 3,6-dimethyl (0.062 g, 0.460 mmol, 1.5 eq.) and DIPEA (0.2 mL, 1.07 mmol, 3.5 eq.) were added and the reaction mixture was brought to rt and stirred for 12 h. The reaction mixture was diluted with water (15 mL) and extracted with DCM. Combined organic layer was then dried over $Na_2SO_4$ and concentrated to obtain crude amide (0.070 g, 42%). MS: 541.4 m/z $(M+H)^+$.

To a mixture of the above crude amide (0.070, 0.129 mmol, 1 eq.) and p-toluenesulfonic acid (PTSA, 0.016 g, 0.064 mmol, 0.5 eq.) in toluene (30 mL) was heated at reflux over a Dean-Stark apparatus for 4 h. The reaction mixture was then concentrated under reduced pressure. The residue was diluted with sat. NaHCO$_3$(15 mL) and extracted with DCM. The combined organic layer was dried over Na$_2$SO$_4$ and concentrated under reduced pressure. The residue was purified by Combiflash chromatography using 4-6% MeOH in DCM as eluent to obtain Example 16 (0.015 mg, 22%). MS: 523.2 m/z (M+H)$^+$; $^1$H NMR: (400 MHz, CD$_3$OD) δ: 7.00 (dd, J=6.0, 8.4 Hz, 1H), 6.89 (s, 2H), 6.81-6.73 (m, 2H), 3.39 (s, 1H), 2.95-2.59 (m, 11H), 2.49-2.46 (m, 8H), 2.30-1.96 (m, 9H), 1.81-1.73 (m, 1H), 1.08 (d, J=6.8 Hz, 3H), 0.42 (d, J=6.8 Hz, 3H).

Example 17. (1R,2R)-2-(2-((3-(4,7-Dimethyl-1H-benzo[d]imidazol-2-yl)propyl)(methyl)amino)ethyl)-6-fluoro-1-isopropyl-1,2,3,4-tetrahydronaphthalen-2-yl morpholine-4-carboxylate

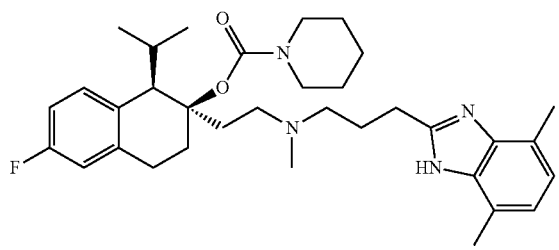 [SMILES: Cc1ccc(C)c2[nH]c(CCCN(C)CC[C@]3(OC(=O)N4CCCCC4)CCc4cc(F)ccc4[C@H]3C(C)C)nc12]

Step 1. 2-((1R,2R)-6-Fluoro-2-hydroxy-1-isopropyl-1,2,3,4-tetrahydronaphthalen-2-yl)ethyl 4-methylbenzenesulfonate

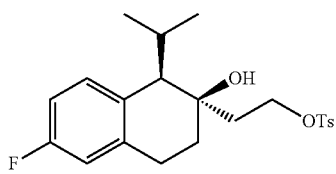 [SMILES: Cc1ccc(S(=O)(=O)OCC[C@]2(O)CCc3cc(F)ccc3[C@H]2C(C)C)cc1]

To a solution of (1R,2R)-6-fluoro-2-(2-hydroxyethyl)-1-isopropyl-1,2,3,4-tetrahydronaphthalen-2-ol (2 g, 7.93 mmol, 1.0 eq) in DCM (20 mL) was added tosyl chloride (2.0 g, 11.11 mmol, 1.4 eq.) and triethylamine (1.6 mL, 11.11 mmol, 1.4 eq.). The reaction mixture was stirred at rt for 24 h. The reaction mixture was added to water (50 mL), extracted with ethyl acetate (50 mL×3). The combined organics were dried over Na$_2$SO$_4$ and concentrated. The crude compound was purified by column chromatography on silica gel (230-400 mesh) using 50% ethyl acetate/hexane as eluent to afford 2-((1R,2R)-6-fluoro-2-hydroxy-1-isopropyl-1,2,3,4-tetrahydronaphthalen-2-yl)ethyl 4-methylbenzenesulfonate as a transparent semisolid (1.4 g, 44%).

Step 2. (1R,2R)-6-Fluoro-1-isopropyl-2-(2-(methylamino)ethyl)-1,2,3,4-tetrahydronaphthalen-2-ol

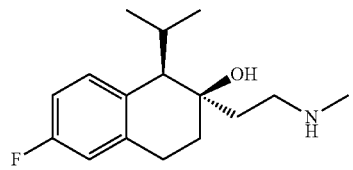 [SMILES: CNCC[C@]1(O)CCc2cc(F)ccc2[C@H]1C(C)C]

A mixture of 2-((1R,2R)-6-fluoro-2-hydroxy-1-isopropyl-1,2,3,4-tetrahydronaphthalen-2-yl)ethyl 4-methylbenzenesulfonate (1 g, 2.46 mmol) and methylamine 2M in MeOH (10 mL) was stirred at 40° C. in a sealed tube for 12 h. The reaction mixture was then added to ice cold water (50 mL) and solid precipitate was filtered, washed with water, and dried under reduced vacuum pressure to obtain (1R,2R)-6-fluoro-1-isopropyl-2-(2-(methylamino)ethyl)-1,2,3,4-tetrahydronaphthalen-2-ol (630 mg, 97%). MS: 266.5 m/z (M+H)$^+$.

Step 3. Methyl 4-((2-((1R,2R)-6-fluoro-2-hydroxy-1-isopropyl-1,2,3,4-tetrahydronaphthalen-2-yl)ethyl)(methyl)amino)butanoate

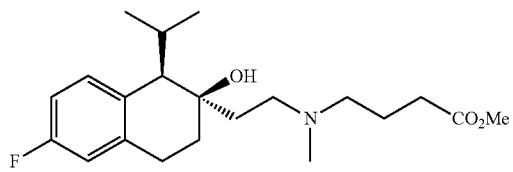 [SMILES: COC(=O)CCCN(C)CC[C@]1(O)CCc2cc(F)ccc2[C@H]1C(C)C]

To a solution of (1R,2R)-6-fluoro-1-isopropyl-2-(2-(methylamino)ethyl)-1,2,3,4-tetrahydronaphthalen-2-ol (1 g, 3.77 mmol, 1 eq.) in a mixture of MeCN (3 mL) and triethylamine (4 mL, 18.06 mmol, 5 eq.) was added 4-bromobutanoic acid methyl ester (0.615 g, 4.52 mmol, 1.2 eq.) and KI (0.313 g, 1.88 mmol 0.5 eq.). The reaction mixture was stirred at 60° C. for 12 hours. The reaction mixture was diluted with water (50 mL) and extracted with DCM. The combined organic layer was then dried over Na$_2$SO$_4$ and concentrated. The crude compound was purified by column chromatography on silica gel (230-400 mesh) using 2.2-2.6% MeOH in DCM as eluent to afford methyl 4-((2-((1R,2R)-6-fluoro-2-hydroxy-1-isopropyl-1,2,3,4-tetrahydronaphthalen-2-yl)ethyl)(methyl)amino)butanoate (0.800 g. 56%). MS: 366.4

Step 4. (1R,2R)-6-Fluoro-1-isopropyl-2-(2-((4-methoxy-4-oxobutyl)(methyl)amino)ethyl)-1,2,3,4-tetrahydronaphthalen-2-yl morpholine-4-carboxylate

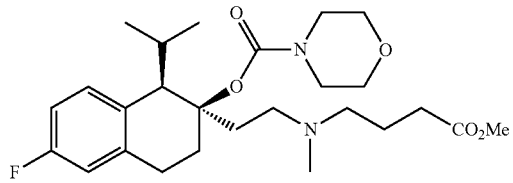 [SMILES: COC(=O)CCCN(C)CC[C@]1(OC(=O)N2CCOCC2)CCc2cc(F)ccc2[C@H]1C(C)C]

To a solution of methyl 4-((2-((1R,2R)-6-fluoro-2-hydroxy-1-isopropyl-1,2,3,4-tetrahydronaphthalen-2-yl)ethyl)(methyl)amino)butanoate (0.450 g, 1.23 mmol, 1 eq.) in DCM at 0° C., DIPEA (0.1 mL, 6.16 mmol, 5 eq.) and 4-nitrophenylchloroformate (0.619 g, 3.08 mmol, 2.5 eq.) were successively added. The solution was brought to rt and stirred for 3 h. The reaction mixture was then cooled to 0° C. and morpholine (1.1 mL, 12.32 mmol, 10 eq.) was added and stirred for 3 h at rt. The reaction mixture was diluted with water (20 mL) and extracted with DCM. The organic layer was dried over $Na_2SO_4$ and concentrated. The crude compound was purified by COMBIFLASH® chromatography using 2.6-3% MeOH in DCM as the eluent to afford (1R,2R)-6-fluoro-1-isopropyl-2-(2-((4-methoxy-4-oxobutyl)(methyl)amino)ethyl)-1,2,3,4-tetrahydronaphthalen-2-yl morpholine-4-carboxylate (0.451 g, 70%). MS: 479.4

Step 5. 4-((2-((1R,2R)-6-Fluoro-1-isopropyl-2-((morpholine-4-carbonyl)oxy)-1,2,3,4-tetrahydronaphthalen-2-yl)ethyl)(methyl)amino)butanoic acid

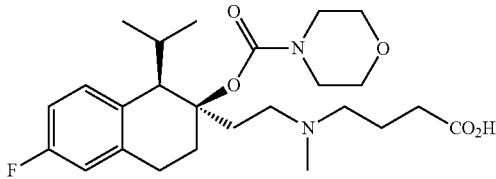 [SMILES: CC(C)[C@@H]1c2ccc(F)cc2CC[C@]1(CCN(C)CCCC(=O)O)OC(=O)N1CCOCC1]

To a solution of (1R,2R)-6-fluoro-1-isopropyl-2-(2-((4-methoxy-4-oxobutyl)(methyl)amino)ethyl)-1,2,3,4-tetrahydronaphthalen-2-yl morpholine-4-carboxylate (0.415 g, 0.86 mmol, 1 eq.) in THF (3 mL) and $H_2O$ (3 mL), LiOH (0.159 g, 2.60 mmol, 3 eq.) was added and stirred for 2 h at rt. The reaction mixture was diluted with a saturated solution of citric acid to an acidic pH and then extracted with 10% MeOH in DCM. The combined organics were dried over $Na_2SO_4$ and concentrated to obtain 4-((2-((1R,2R)-6-fluoro-1-isopropyl-2-((morpholine-4-carbonyl)oxy)-1,2,3,4-tetrahydronaphthalen-2-yl)ethyl)(methyl)amino)butanoic acid (0.360 g, 89%). MS: 465.2 m/z $(M+H)^+$.

Step 6. (1R,2R)-2-(2-((3-(4,7-Dimethyl-1H-benzo[d]imidazol-2-yl)propyl)(methyl)amino)ethyl)-6-fluoro-1-isopropyl-1,2,3,4-tetrahydronaphthalen-2-yl morpholine-4-carboxylate To a cooled solution of 4-((2-((1R,2R)-6-fluoro-1-isopropyl-2-((morpholine-4-carbonyl)oxy)-1,2,3,4-tetrahydronaphthalen-2-yl)ethyl)(methyl)amino)butanoic acid (0.360 g, 0.77 mmol, 1 eq.) in DMF (3.6 mL) at 0° C., HATU (0.442 g, 0.92 mmol, 1.2 eq.) was added and stirred for 30 minutes at 0° C. under N2 atmosphere. 1,2-Benzendiamine, 3,6-dimethyl (0.147 g, 1.08 mmol, 1.4 eq.) and DIPEA (0.4 mL, 1.93 mmol, 2.5 eq.) were added and the reaction mixture was brought to rt and stirred for 12 h. The reaction mixture was diluted with water (25 mL) and extracted with DCM. The combined organic layer was then dried over $Na_2SO_4$ and concentrated to obtain crude amide (0.330 g, 73%). MS: 583.4 m/z $(M+H)^+$.

To a mixture of above crude amide (0.330 g, 0.56 mmol, 1 eq.) and pyridinium p-toluenesulfonate (PPTS, 0.071 g, 0.28 mmol, 0.5 eq.) in toluene (16 mL) was heated at reflux over a Dean-Stark apparatus for 4 h. The reaction mixture was concentrated under reduced pressure the residue was diluted with sat. $NaHCO_3$ (25 mL) and extracted with DCM. The combined organic layer was dried over $Na_2SO_4$ and concentrated under reduced pressure. The residue was purified on Combiflash column using 2.9-3.2% MeOH in DCM as eluent to obtain Example 17 (0.100 g, 32%). MS: 565.4 m/z $(M+H)^+$; $^1H$ NMR: (400 MHz, $CD_3OD$) δ: 7.29 (s, 2H), 7.03 (bs, 1H), 6.91-6.85 (m, 2H), 3.67-2.78 (m, 16H), 2.61 (s, 6H), 2.37 (bs, 2H), 2.16-1.99 (m, 4H), 1.10 (d, J=6.8 Hz, 3H), 0.44 (d, J=6.8 Hz, 3H).

Example 18. (1S,2S)-2-(2-((4-((2-Amino-3,6-dimethylphenyl)amino)-4-oxobutyl)(ethyl)amino)ethyl)-6-fluoro-1-isopropyl-1,2,3,4-tetrahydronaphthalen-2-yl morpholine-4-carboxylate

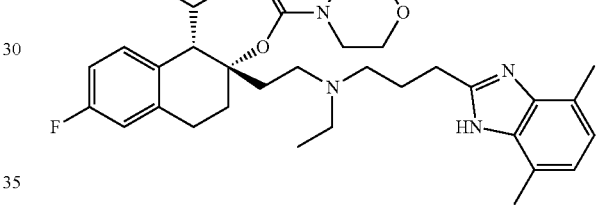

Step 1. (1S,2S)-2-(2-(Ethylamino)ethyl)-6-fluoro-1-isopropyl-1,2,3,4-tetrahydronaphthalen-2-ol

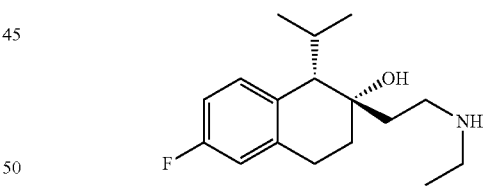

A mixture of Intermediate 1 (1 g, 2.46 mmol) and ethylamine (2M) in MeOH (10 mL) was stirred at 40° C. in a sealed tube for 12 h. The reaction mixture was added to ice cold water (50 mL) and solid precipitate was filtered, washed with water, and dried under vacuum to obtain a (1S,2S)-2-(2-(ethylamino)ethyl)-6-fluoro-1-isopropyl-1,2,3,4-tetrahydronaphthalen-2-ol (618 mg, 90%). $^1H$ NMR (DMSO-d6): δ 7.01 (dd, J=6.4, 9.2 Hz, 1H), 6.89-6.85 (m, 2H), 2.85 (dd, J=6.4, 18.0 Hz, 1H), 2.71-2.62 (m, 3H), 2.5-2.33 (m, 4H) 1.89-1.74 (m, 2H), 1.62 (dd, J=8.0, 13.6 Hz, 1H), 1.38-1.28 (m, 2H), 1.04 (d, J=6.8 Hz, 3H), 0.97 (t, J=7.2 Hz, 3H), 0.34 (d, J=7.2 Hz, 3H).

Step 2. Methyl 4-(ethyl(2-((1S,2S)-6-fluoro-2-hydroxy-1-isopropyl-1,2,3,4-tetrahydronaphthalen-2-yl)ethyl)amino)butanoate

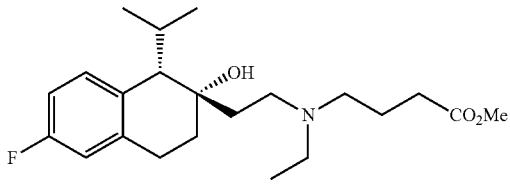 [SMILES: CCN(CCCC(=O)OC)CC[C@@]1(O)CCc2cc(F)ccc2[C@@H]1C(C)C]

To a solution of (1S,2S)-2-(2-(ethylamino)ethyl)-6-fluoro-1-isopropyl-1,2,3,4-tetrahydronaphthalen-2-ol (1.4 g, 5.01 mmol, 1 eq.) in a mixture of MeCN (3 mL) and triethylamine (4 mL, 25.08 mmol, 5 eq.) was added 4-bromomethylbutyrate (1.09 g, 6.02 mmol, 1.2 eq.) and KI (0.416 g, 2.50 mmol 0.5 eq.). The reaction mixture was stirred at 60° C. for 12 hours. The reaction mixture was then diluted with water (50 mL) and extracted with DCM. The combined organic layer was then dried over $Na_2SO_4$ and concentrated. The crude compound was purified by column chromatography on silica gel (230-400 mesh) using 2.2-2.6% MeOH in DCM as eluent to afford methyl 4-(ethyl(2-((1S,2S)-6-fluoro-2-hydroxy-1-isopropyl-1,2,3,4-tetrahydronaphthalen-2-yl)ethyl)amino)butanoate (1.2 g. 63%). MS: 380.2 m/z $(M+H)^+$

Step 3. (1S,2S)-2-(2-(Ethyl(4-methoxy-4-oxobutyl)amino)ethyl)-6-fluoro-1-isopropyl-1,2,3,4-tetrahydronaphthalen-2-yl morpholine-4-carboxylate

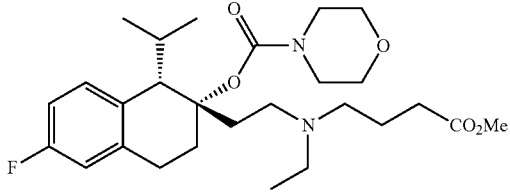 [SMILES: CCN(CCCC(=O)OC)CC[C@@]1(OC(=O)N2CCOCC2)CCc2cc(F)ccc2[C@@H]1C(C)C]

To a solution of methyl 4-(ethyl(2-((1S,2S)-6-fluoro-2-hydroxy-1-isopropyl-1,2,3,4-tetrahydronaphthalen-2-yl)ethyl)amino)butanoate (0.5 g, 1.31 mmol, 1 eq.) in DCM at 0° C., DIPEA (0.5 mL, 4.61 mmol, 3.5 eq.) and 4-nitrophenylchloroformate (2.0 g, 3.29 mmol, 2.5 eq.) were successively added. The solution was brought to rt and stirred for 3 h. The reaction mixture was then cooled to 0° C. and morpholine (0.1 mL, 13.1 mmol, 10 eq.) was added and the mixture was stirred for 3 h at rt. The reaction mixture was diluted with water (20 mL) and extracted with DCM. The organic layer was then concentrated and dried over $Na_2SO_4$. The crude compound was purified by Combiflash chromatography using 2.6-3% MeOH in DCM as eluent to afford (1S,2S)-2-(2-(ethyl(4-methoxy-4-oxobutyl)amino)ethyl)-6-fluoro-1-isopropyl-1,2,3,4-tetrahydronaphthalen-2-yl morpholine-4-carboxylate (0.35 g, 54%). MS: 493.4 m/z $(M+H)^+$

Step 4. 4-(ethyl(2-((1S,2S)-6-Fluoro-1-isopropyl-2-((morpholine-4-carbonyl)oxy)-1,2,3,4-tetrahydronaphthalen-2-yl)ethyl)amino)butanoic acid

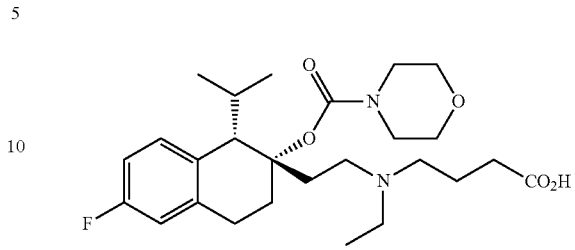

To a solution of (1S,2S)-2-(2-(ethyl(4-methoxy-4-oxobutyl)amino)ethyl)-6-fluoro-1-isopropyl-1,2,3,4-tetrahydronaphthalen-2-yl morpholine-4-carboxylate (0.59 g, 1.19 mmol, 1 eq.) in THF (3 mL) and $H_2O$ (3 mL), LiOH (0.151 g, 3.59 mmol, 3 eq.) was added and stirred for 2 h at rt. The reaction mixture was diluted with a saturated solution of citric acid to an acidic pH and then extracted with 10% MeOH in DCM. The combined organic layer was dried over $Na_2SO_4$ and concentrated to obtain 4-(ethyl(2-((1S,2S)-6-fluoro-1-isopropyl-2-((morpholine-4-carbonyl)oxy)-1,2,3,4-tetrahydronaphthalen-2-yl)ethyl)amino)butanoic acid (0.57 g, 99%). MS: 479.4 m/z $(M+H)^+$.

Step 5. (1S,2S)-2-(2-((4-((2-Amino-3,6-dimethylphenyl)amino)-4-oxobutyl)(ethyl)amino)ethyl)-6-fluoro-1-isopropyl-1,2,3,4-tetrahydronaphthalen-2-yl morpholine-4-carboxylate To a cooled solution of 4-(ethyl(2-((1S,2S)-6-fluoro-1-isopropyl-2-((morpholine-4-carbonyl)oxy)-1,2,3,4-tetrahydronaphthalen-2-yl)ethyl)amino)butanoic acid (0.570 g, 1.19 mmol, 1 eq.) in DMF (5.7 mL) at 0° C., HATU (0.543 g, 1.43 mmol, 1.2 eq.) was added and stirred for 30 minutes at 0° C. under N2 atmosphere. 1,2-Benzendiamine, 3,6-dimethyl (0.243 g, 1.78 mmol, 1.5 eq.) and DIPEA (0.7 mL, 4.17 mmol, 3.5 eq.) were added and the reaction mixture was brought to rt and stirred for 12 h. The reaction mixture was diluted with water (25 mL) and extracted with DCM. The combined organic layer was then dried over $Na_2SO_4$ and concentrated to obtain crude amide (0.57 g, 80%). MS: 598.07 m/z $(M+H)^+$.

To a mixture of above crude amide (0.570, 0.95 mmol, 1 eq.) and PTSA (0.024 g, 0.095 mmol, 0.1 eq.) in toluene (30 mL) was heated at reflux over a Dean-Stark apparatus for 4 h. The reaction mixture was then concentrated under reduced pressure. The residue was diluted with sat. $NaHCO_3$ (25 mL) and extracted with DCM. The combined organic layer was dried over $Na_2SO_4$ and concentrated under reduced pressure. The residue was purified by Combiflash chromatography using 2.9-3.2% MeOH in DCM as eluent to obtain compound Example 18 (65 mg, 12%). MS: 579.5 m/z $(M+H)^+$; 1H NMR: (400 MHz, $CD_3OD$) δ: 6.98 (dd, J=5.6, 8.4 Hz, 1H), 6.90 (s, 2H), 6.80 (td, J=2.8, 8.4 Hz, 1H), 6.71 (d, J=9.6 Hz, 1H), 3.6-3.4 (m, 8H), 2.94-2.87 (m, 3H), 2.76-2.63 (m, 2H), 2.55-2.50 (m, 10H), 2.28-1.95 (m, 6H), 1.74-1.67 (m, 1H), 1.08 (d, J=6.8 Hz, 3H), 1.01 (t, J=6.8 Hz, 3H), 0.41 (d, J=6.8 Hz, 3H).

Example 19. (1S,2S)-2-(2-((2-(1-(1H-Benzo[d]imidazol-2-yl)cyclopropyl)ethyl)(methyl)amino)ethyl)-6-fluoro-1-isopropyl-1,2,3,4-tetrahydronaphthalen-2-yl morpholine-4-carboxylate

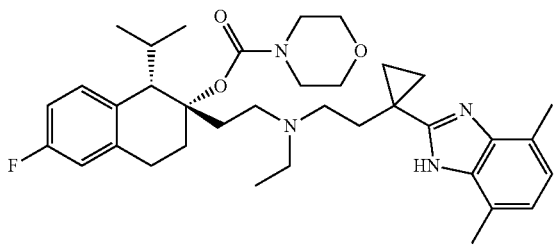 [SMILES: CCN(CCC1(c2nc3c(C)ccc(C)c3[nH]2)CC1)CC[C@@]1(OC(=O)N2CCOCC2)CCc2cc(F)ccc2[C@@H]1C(C)C]

Step 1. tert-Butyl 1-allylcyclopropane-1-carboxylate

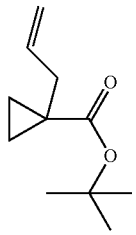

To a cooled solution (−40° C.) of DIPEA (4.1 mL, 29.57 mmol, 2.1 eq) in THF (25 mL), was added n-BuLi (2.5M in hexanes, 11.2 mL, 28.36 mmol, 2 eq.) drop wise and the mixture was then stirred for 0.5 hr and then cooled to −78° C. Next, a solution of tert-butyl cyclopropanecarboxylate (2 g, 14.08 mmol, 1 eq.) in THF (5 mL) was added and the reaction mixture was stirred for 4 h at −78° C. 1-Propene, 3-bromo-(3.6 mL 42.25 mmol, 3 eq.) was added and reaction mixture was stirred for 2 h at −78° C. The reaction was then quenched with NH$_4$C$_1$ (30 mL) and extracted with DCM. The organic layer was dried over Na$_2$SO$_4$ and concentrated to give tert-butyl 1-allylcyclopropane-1-carboxylate (1.5 g, 58%). $^1$H NMR: (400 MHz, CDCl$_3$) δ: 5.92-5.81 (m, 1H), 5.07-5.00 (m, 2H), 2.28 (d, J=6.8 Hz, 2H), 1.45 (s, 9H), 1.15 (dd, J=4.0, 3.2 Hz, 2H), 0.67 (dd, 4.0, 2.8 Hz, 2H).

Step 2. tert-Butyl 1-(2-oxoethyl)cyclopropane-1-carboxylate

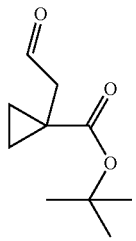

To a solution of tert-butyl 1-allylcyclopropane-1-carboxylate (1 g, 5.49 mmol, 1 eq.) in DCM (12 mL), O$_3$ gas was added at −78° C. until a blue color appeared and remained consistent. Next, N2 gas was added to the reaction mixture until the blue color disappeared and the solution became colorless, then dimethyl sulfide (DMS, 1.14 g, 5.49 mmol, 3.68 eq.) and triethylamine (1.8 mL, 5.36 mmol, 10 eq.) were added and the mixture was stirred for 1 h at rt. The reaction mixture was then diluted with water (20 mL) and extracted with DCM. The organic layer was dried over Na$_2$SO$_4$. The combined organic layer was concentrated to half volume and used in the next step without any further purification.

Step 3. ter t-Butyl 1-(2-((2-(((1 S,2S)-6-fluoro-2-hydroxy-1-isopropyl-1,2,3,4-tetrahydronaphthalen-2-yl)ethyl)(methyl)amino)ethyl)cyclopropane-1-carboxylate

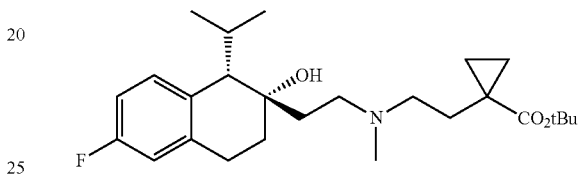

To a solution of Intermediate 2 (0.700 g, 2.73 mmol, 1 eq.) in MeOH and catalytic AcOH was added solution of tert-butyl 1-(2-oxoethyl)cyclopropane-1-carboxylate from Step 2 in DCM and stirred for 1 h at rt. NaBH$_3$CN (0.508 g, 8.20 mmol, 3.0 eq.) was then added in portions at 0° C., over 30 min, and the resulting mixture was stirred for an additional 2 h. The reaction was quenched with sat. NaHCO$_3$(30 mL) and extracted with DCM. The combined organic layer was dried over Na$_2$SO$_4$ and concentrated. The crude compound was purified by column chromatography on silica gel (60-120 mesh) using 2.4-2.8% MeOH in DCM as eluent to afford tert-butyl 1-(2-((2-(((1S,2S)-6-fluoro-2-hydroxy-1-isopropyl-1,2,3,4-tetrahydronaphthalen-2-yl)ethyl)(methyl)amino)ethyl)cyclopropane-1-carboxylate (0.650 g, 56%). MS: 434.4 m/z (M+H)$^+$.

Step 4. 1-(2-((2-(((1S,2S)-6-Fluoro-2-hydroxy-1-isopropyl-1,2,3,4-tetrahydronaphthalen-2-yl)ethyl)(methyl)amino)ethyl)cyclopropane-1-carboxylic acid

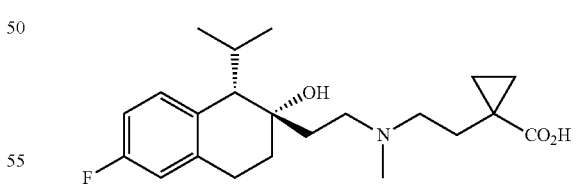

A solution of tert-butyl 1-(2-((2-(((1S,2S)-6-fluoro-2-hydroxy-1-isopropyl-1,2,3,4-tetrahydronaphthalen-2-yl)ethyl)(methyl)amino)ethyl)cyclopropane-1-carboxylate (0.630 g, 1.50 mmol, 1 eq.) in 4M HCl in dioxane in (7 mL) was stirred for 2 h at rt. The reaction mixture was diluted with saturated NaHCO$_3$ and washed with DCM and the aqueous layer was acidified with citric acid to pH 6 and extracted with 10% MeOH in DCM. The combined organic layer was dried over Na$_2$SO$_4$ and concentrated to obtain 1-(2-((2-(((1S, 2S)-6-fluoro-2-hydroxy-1-isopropyl-1,2,3,4-tetrahydronaphthalen-2-yl)ethyl)(methyl)amino)ethyl)cyclopropane-1-carboxylic acid (0.450 g, 72%). MS: 378.2 m/z (M+H)+.

Step 5. (1S,2S)-2-(2-((2-(1-(1H-Benzo[d]imidazol-2-yl)cyclopropyl)ethyl)(methyl)amino)ethyl)-6-fluoro-1-isopropyl-1,2,3,4-tetrahydronaphthalen-2-ol

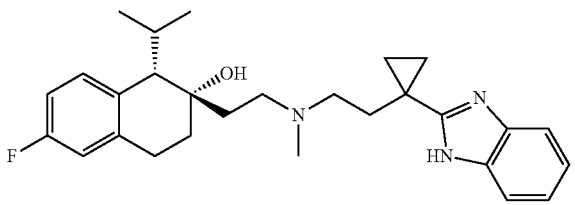 [SMILES: CC(C)[C@H]1c2ccc(F)cc2CC[C@]1(O)CCN(C)CCC1(c2nc3ccccc3[nH]2)CC1]

To a solution of 1-(2-((2-(((1S,2S)-6-fluoro-2-hydroxy-1-isopropyl-1,2,3,4-tetrahydronaphthalen-2-yl)ethyl)(methyl)amino)ethyl)cyclopropane-1-carboxylic acid (0.450 g, 1.19 mmol, 1 eq) in DMF (3 mL) and pyridine (3 mL) at rt, carbonyldimidazole (CDI, 290.05 g, 1.79 mmol, 1.2 eq.) was added and the mixture was stirred for 2 h at 45° C. The reaction mixture was then cooled to rt and o-phenyldiamine (0.130 g, 1.19 mmol, 1 eq.) was added and the reaction mixture was stirred for 12 h. The reaction mixture was diluted with water (25 mL) and extracted with DCM. The combined organic layer was then dried over $Na_2SO_4$ and concentrated to obtain crude amide (0.350 g, 66%). MS: 468.3 m/z (M+H)+.

A solution of above crude amide (0.350 g, 7.79 mmol, 1 eq.) and PPTS (0.094 g, 3.74 mmol, 0.5 eq.) in toluene (17.5 mL) was refluxed over Dean Stark for 4 h. The reaction mixture was concentrated under reduced pressure the residue was diluted with sat. $NaHCO_3$ (25 mL) and extracted with DCM. Combined organic layer was dried over $Na_2SO_4$ and concentrated under reduced pressure. The residue was purified by combi-flash using 2.9-3.2% MeOH in DCM as eluent to obtain (1S,2S)-2-(2-((2-(1-(1H-benzo[d]imidazol-2-yl)cyclopropyl)ethyl)(methyl)amino)ethyl)-6-fluoro-1-isopropyl-1,2,3,4-tetrahydronaphthalen-2-ol (0.250 g, 74%). MS: 450.2 m/z (M+H)+.

Step 6. (1S,2S)-2-(2-((2-(1-(1H-Benzo[d]imidazol-2-yl)cyclopropyl)ethyl)(methyl)amino)ethyl)-6-fluoro-1-isopropyl-1,2,3,4-tetrahydronaphthalen-2-yl morpholine-4-carboxylate To a solution of (1S,2S)-2-(2-((2-(1-(1H-benzo[d]imidazol-2-yl)cyclopropyl)ethyl)(methyl)amino)ethyl)-6-fluoro-1-isopropyl-1,2,3,4-tetrahydronaphthalen-2-ol (0.250 g, 0.556 mmol, 1 eq.) in DCM at 0° C., DIPEA (0.4 mL, 1.94 mmol, 3.5 eq) and 4-nitrophenylchloroformate (0.279 g, 1.39 mmol, 2.5 eq.) were successively added. The solution was brought to rt and stirred for 3 h. The reaction mixture was then cooled to 0° C. and morpholine (0.5 mL, 5.36 mmol, 10 eq.) was added and the mixture was stirred for 3 h at rt. The reaction mixture was diluted with water (20 mL) and extracted with DCM. The organic layer was dried over $Na_2SO_4$ and concentrated. The crude compound was purified by COMBIFLASH® chromatography using 2.6-3% MeOH in DCM as eluent to afford Example 19 (0.015 g, 05%). MS: 563.4 m/z (M+H)+; 1H NMR: (400 MHz, $CD_3OD$) δ: 7.41 (bs, 2H), 7.20-7.17 (m, 2H), 7.01 (dd, J=6.0, 8.4 Hz, 1H), 6.83 (td, J=8.4, 2.4 Hz, 1H), 6.75 (dd, J=2.0, 9.6 Hz, 1H), 3.59 (bs, 4H), 3.43-3.47 (m, 4H), 2.95 (dd, J=6.4, 18.0 Hz, 1H), 2.82-2.32 (m, 7H), 2.25 (s, 3H), 2.11-2.03 (m, 4H), 1.95 (t, J=7.2 Hz, 2H), 1.81-1.74 (m, 1H), 1.39-1.21 (m, 4H), 1.09 (d, J=6.8 Hz, 3H), 0.94-0.90 (m, 2H), 0.43 (d, J=7.2 Hz, 3H).

Examples 20A and 20B. (4S)-3-(2-((3-s(1H-Benzo[d]imidazol-2-yl)propyl)(methyl)amino)ethyl)-7-fluoro-4-isopropylchroman-3-yl methylcarbamate (Two Diastereoisomers)

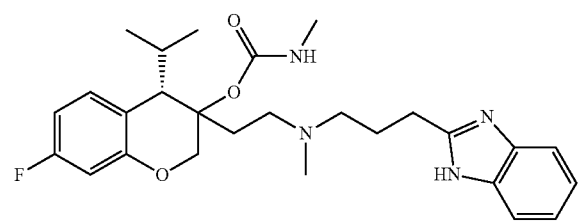 [SMILES: CNC(=O)OC1(CCN(C)CCCc2nc3ccccc3[nH]2)COc2cc(F)ccc2[C@@H]1C(C)C]

Step 1. (4S)-3-(2-((3-(1H-benzo[d]imidazol-2-yl)propyl)(methyl)amino)ethyl)-7-fluoro-4-isopropyl-chroman-3-ol (Mixture of Diastereoisomers)

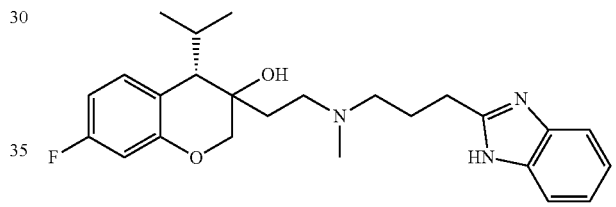

A solution of 2-((4S)-7-fluoro-3-hydroxy-4-isopropylchroman-3-yl)ethyl 4-methylbenzenesulfonate (0.150 g, 0.367 mmol, 1.0 eq.) and 3-(1H-benzo[d]imidazol-2-yl)-N-methylpropan-1-amine (0.069 g, 0.367 mmol, 1 eq.) in triethylamine (1 mL) was stirred at 60° C. for 24 h. The reaction mixture was quenched with water (20 mL) and extracted in DCM. The combined organics were, washed with brine, dried over $Na_2SO_4$, and concentrated. The crude compound was purified by column chromatography on silica gel (230-400 mesh) using 3-4% MeOH in DCM as eluent to afford (4S)-3-(2-((3-(1H-benzo[d]imidazol-2-yl)propyl) (methyl)amino)ethyl)-7-fluoro-4-isopropylchroman-3-ol as a mixture of diastereoisomers (0.050 g). MS: 426.55 m/z (M+H)+. The two diastereoisomers can be designated as (3S,4S)-3-(2-((3-(1H-benzo[d]imidazol-2-yl)propyl) (methyl)amino)ethyl)-7-fluoro-4-isopropylchroman-3-ol and (3R,4S)-3-(2-((3-(1H-benzo[d]imidazol-2-yl)propyl) (methyl)amino)ethyl)-7-fluoro-4-isopropylchroman-3-ol.

Step 2. (4S)-3-(2-((3-(1H-Benzo[d]imidazol-2-yl)propyl)(methyl)amino)ethyl)-7-fluoro-4-isopropyl-chroman-3-yl methylcarbamate (Two Diastereoisomers)

To a solution of (4S)-3-(2-((3-(1H-benzo[d]imidazol-2-yl)propyl)(methyl)amino)ethyl)-7-fluoro-4-isopropylchroman-3-ol from Step 1 (0.050 g, 0.117 mmol, 1 eq.) in DCM (1.5 mL) at 0° C., DIPEA (0.08 mL, 0.587 mmol, 5 eq.) and 4-nitrophenylchloroformate (0.071 g, 0.352 mmol, 3 eq.)

were successively added. The solution was brought to rt and stirred for 3 h. The reaction mixture was then cooled to 0° C. and 33% MeNH₂ in MeOH (1.1 mL) was added and the mixture was stirred for 3 h at rt. The reaction mixture was then diluted with water (20 mL) and extracted with DCM. The organic layer was dried over Na₂SO₄ and concentrated. The crude product was purified by preparative TLC using 10% MeOH in DCM as the mobile phase to obtain Examples 20A and 20B as individual diastereoisomers (0.015 g, 26%). MS: 483.6 m/z (M+H)⁺; 1H-NMR (CD₃OD): δ 7.49 (dd, J=3.2, 6.0 Hz, 2H), 7.20 (dd, J=3.2, 6.0 Hz, 2H), 7.03 (dd, J=6.4, 8.4 Hz, 1H), 6.61 (td, J=8.4, 2.4 Hz, 1H), 6.50 (dd, J=2.4, 10.4 Hz, 1H), 4.26 (dd, J=2.0, 11.2 Hz, 1H), 4.03 (d, J=11.2 Hz, 1H), 2.89 (t, J=7.2 Hz, 2H), 2.70-2.43 (m, 7H), 2.30-1.84 (m, 8H), 1.12 (d, J=6.8 Hz, 3H), 0.56 (d, J=6.8 Hz, 3H). The diastereoisomers can be designated as (3S,4S)-3-(2-((3-(1H-benzo[d]imidazol-2-yl)propyl)(methyl)amino)ethyl)-7-fluoro-4-isopropylchroman-3-ylmethylcarbamate and (3R,4S)-3-(2-((3-(1H-benzo[d]imidazol-2-yl)propyl)(methyl)amino)ethyl)-7-fluoro-4-isopropylchroman-3-yl methylcarbamate.

Examples 21A and 21B. (4S)-3-(2-((3-(4,7-Dimethyl-1H-benzo[d]imidazol-2-yl)propyl)(methyl)amino)ethyl)-7-fluoro-4-isopropylchroman-3-yl methylcarbamate (Two Diastereoisomers)

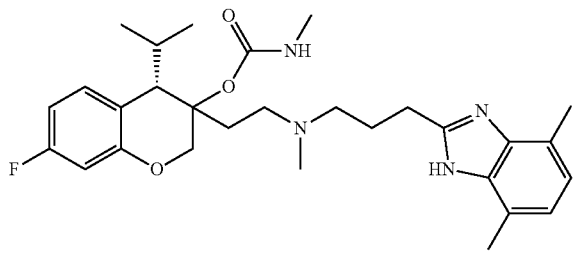 [SMILES: CNC(=O)OC1(CCN(C)CCCc2nc3c(C)ccc(C)c3[nH]2)COc2cc(F)ccc2[C@@H]1C(C)C]

Step 1. (4S)-3-(2-((3-(4,7-dimethyl-1H-benzo[d]imidazol-2-yl)propyl)(methyl)amino)ethyl)-7-fluoro-4-isopropylchroman-3-ol (Mixture of Diastereoisomers)

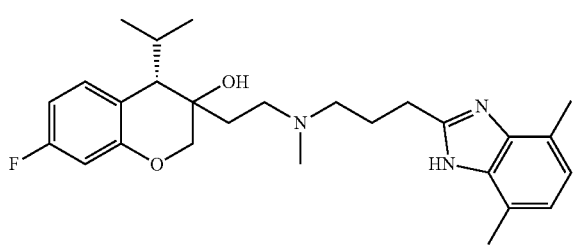 [SMILES: Cc1ccc(C)c2[nH]c(CCCN(C)CCC3(O)COc4cc(F)ccc4[C@@H]3C(C)C)nc12]

The title compound was prepared using a procedure similar to Example 20. A solution of 2-((4S)-7-fluoro-3-hydroxy-4-isopropylchroman-3-yl)ethyl 4-methylbenzenesulfonate (0.170 g, 0.416 mmol, 1.0 eq.) and 3,6-dimethyldianiline (0.145 g, 0.416 mmol, 1 eq.) in triethylamine (1 mL) was stirred at 60° C. for 24 h. The reaction mixture was diluted with water (20 mL) and extracted in DCM. The combined organics were washed with brine, dried over Na₂SO₄, and concentrated. The crude compound was purified by column chromatography on silica gel (230-400 mesh) using 3-4% DCM/MeOH as eluent to afford (4S)-3-(2-((3-(4,7-dimethyl-1H-benzo[d]imidazol-2-yl)propyl)(methyl)amino)ethyl)-7-fluoro-4-isopropylchroman-3-ol as a mixture of diastereoisomers (0.060 g, 32%). MS: 454.65 m/z (M+H)⁺. The diastereoisomers can be designated as (3S,4S)-3-(2-((3-(4,7-dimethyl-1H-benzo[d]imidazol-2-yl)propyl)(methyl)amino)ethyl)-7-fluoro-4-isopropylchroman-3-ol and (3R,4S)-3-(2-((3-(4,7-dimethyl-1H-benzo[d]imidazol-2-yl)propyl)(methyl)amino)ethyl)-7-fluoro-4-isopropylchroman-3-ol.

Step 2. (4S)-3-(2-((3-(4,7-Dimethyl-1H-benzo[d]imidazol-2-yl)propyl)(methyl)amino)ethyl)-7-fluoro-4-isopropylchroman-3-yl methylcarbamate (Two Diastereoisomers)

To a solution of (4S)-3-(2-((3-(4,7-dimethyl-1H-benzo[d]imidazol-2-yl)propyl)(methyl)amino)ethyl)-7-fluoro-4-isopropylchroman-3-ol from Step 1 (0.060 g, 0.132 mmol, 1 eq.) in DCM (1.2 mL) at 0° C., DIPEA (0.1 mL, 0.662 mmol, 5 eq.) and 4-nitrophenylchloroformate (0.075 g, 0.375 mmol, 3 eq.) were successively added. The solution was brought to rt and stirred for 3 h. The reaction mixture was then cooled to 0° C. and 33% MeNH₂ in MeOH (1 mL) was added and the mixture was stirred for 3 h at rt. The reaction mixture was diluted with water (20 mL) and extracted with DCM. The organic layer was dried over Na₂SO₄ and concentrated. The crude material was purified by preparative TLC using 10% MeOH in DCM as mobile phase to obtain Examples 21A and 21B as individual diastereoisomers (0.010 g, 13%). MS: 511.4 m/z (M+H)⁺; 1H-NMR (CD₃OD): δ 7.00 (dd, J=6.8, 8.4 Hz, 1H), 6.90 (s, 2H), 6.60 (td, J=11.2, 2.4 Hz, 1H), 6.40 (dd, J=2.4, 10.0 Hz, 1H), 4.22 (dd, J=2.0, 11.2 Hz, 1H), 4.03 (d, J=11.2 Hz, 1H), 3.30 (s, 1H), 2.99 (t, J=11.2 Hz, 2H), 2.87-2.30 (m, 16H), 2.14-1.93 (m, 4H), 1.11 (d, J=6.8 Hz, 3H), 0.55 (d, J=7.2 Hz, 3H). The diastereoisomers can be designated as (3S,4S)-3-(2-((3-(4,7-dimethyl-1H-benzo[d]imidazol-2-yl)propyl)(methyl)amino)ethyl)-7-fluoro-4-isopropylchroman-3-yl methylcarbamate and (3R,4S)-3-(2-((3-(4,7-dimethyl-1H-benzo[d]imidazol-2-yl)propyl)(methyl)amino)ethyl)-7-fluoro-4-isopropylchroman-3-yl methylcarbamate.

Example A. Cell Proliferation Assay by CCK-8 Reagent

Human Glioma cancer cell line U251 was maintained in DMEM (Gibco, Cat #10569-10) supplemented with 10% fetal bovine serum inactivated at 56° C. (Gibco, Cat #10082-147), 100 U/mL penicillin, and 100 μg/mL streptomycin (Gibco, Cat #15140-122) at 37° C. and 1% MEM non-essential amino acid (Sigma, Cat #M7145) in a humid atmosphere containing 5% CO₂. The cells were seeded at 2.5×103 cells/well in a 96 well plate (BD falcon, Cat #353072) with 200 pt volume/well and kept in 37° C./5% CO₂ incubator for 0/N incubation. The seeding density was optimized previously based on growth curve. On the next day, plated cells were incubated with each test compounds at eight different concentrations (100, 50, 25, 12.5, 6.25, 3.125, 1.5 and 0.78) in triplicates. DMSO was used as a Vehicle control and Culture medium was used as blank control for the assay in each plate. The percentage of DMSO was kept uniform across the plate as <1%. The compound treated cells were incubated in 37° C./5% CO₂ incubator for 72 hours. After incubation period, 104/well CCK-8 reagent (Dojindo, Cat #CK04) was added in all the wells and plate was kept in 37° C./5% $CO_2$ incubator for 3 hours. After CCK-8 incubation, absorbance was measured @ 450 nm using Spectrophotometer (BMG, Omega Polar Star). % Viability values at each concentration were calculated with respect to Vehicle control and $EC_{50}$ values were calculated using graph pad prism software and are shown in Table A.

TABLE A

| Example | U251 ($EC_{50}$/μM) |
|---|---|
| 1 | 6 |
| 2 | 10 |
| 3 | 6 |
| 4 | 2.5 |
| 5 | 10 |
| 6 | 15 |
| 7 | 7.7 |
| 8 | 6.8 |
| 9 | 68 |
| 10 | 9.5 |
| 11 | 2.5 |
| 12 | 12 |
| 13 | 4.6 |
| 14 | 3.8 |
| 15 | 4.8 |
| 16 | 6 |
| 17 | 4.3 |
| 18 | 28 |
| 19 | 23 |
| 20A | 54 |
| 20B | 12 |
| 21A | 7 |
| 21B | 9 |
| Mibefradil | 12 |

Example B. Cytochrome P450-3A4 using Human Liver Microsomes

The CYP3A4 inhibition assays were conducted using Human Liver Microsomes purchased from Invitrogen and designed to screen potential inhibitors of Cytochrome P450 in physiological condition. Initially the following reagents/mixtures were prepared: (i) Assay buffer: 0.1 M Phosphate buffer pH—7.4 (ii) Cofactor: 15 mM stock was prepared in assay buffer. Final concentration in assay—1.5 mM (iii) Substrate—50 mM DMSO stock was prepared for testosterone. From this a 10 mM sub-stock was prepared in MeCN. Further, a working stock solution of 700 μM was prepared in assay buffer. Final concentration in assay—70 μM (iv) Enzyme: 20 mg/mL stock was provided by manufacturer. Final concentration in assay was 0.5 mg/mL. At the start of the experiment, various concentrations of compound (7 different concs.) or positive control (Ketoconazole at a single concentration) were prepared in assay buffer. For 100 μL of final reaction system, 2.5 μL of HLM (20 mg/ml), 50 μL of test compound/reference compound from each concentration was added. Subsequently, 10 μL of substrate (testosterone 700 μM) and 10 μL of Cofactor (NADPH; 15 mM) were added. The volume was increased to 100 μL by adding assay buffer. DMSO concentration was kept as 0.5% uniform across all the reactions. The reaction was then allowed to incubate for 45 min at 37° C. After completion of the incubation period, the reaction was terminated by addition of 200 μL of chilled MeCN containing internal standard (Dexamethasone). The samples were than centrifuged and supernatants were analyzed using LCMS/MS. The data normalization was performed with respect to internal standard and % inhibition was calculated with respect to DMSO control. The $IC_{50}$ values were calculated using Graph Pad Prism software and are shown in Table B.

Example C. Cytochrome P450-2D6 Using Human Liver Microsomes

The CYP2D6 inhibition assays were conducted using Human Liver Microsomes purchased from Invitrogen and designed to screen potential inhibitors of Cytochrome P450 in physiological condition. Initially the following reagents/mixtures were prepared: (i) Assay buffer: 0.1 M Phosphate buffer pH—7.4 (ii) Cofactor: 15 mM stock was prepared in assay buffer. Final concentration in assay—1.5 mM (iii) Substrate—50 mM DMSO stock was prepared for Bufuralol. From this, a 10 mM sub-stock was prepared in MeCN. Further, a working stock solution of 50 μM was prepared in assay buffer. Final concentration in assay 5 μM (iv) Enzyme: 20 mg/mL stock was provided by the manufacturer. Final concentration in assay is 0.25 mg/mL. At the start of the experiment, various concentrations of compound (7 different concs.) or positive control (Quinidine at a single concentration) were prepared in assay buffer. For 1004 of final reaction system, 1.254 of HLM (20 mg/ml), 504 of 2× stock of test compound/reference compound (from each concentration) was added. Subsequently, 104 of substrate (Bufuralol—50 μM) and 104 of Cofactor (NADPH; 15 mM) were added. The volume was increased to 1004 by adding assay buffer. The reaction was then incubated for 10 min at 37° C. After completion of the incubation period, the reaction was terminated by addition of 2004 of chilled MeOH containing internal standard (Propranolol). The samples were than centrifuged and supernatants were analyzed using LCMS/MS. The data normalization was performed with respect to internal standard and % inhibition was calculated with respect to DMSO control. The $IC_{50}$ values were calculated using Graph Pad Prism software and are shown in Table B.

TABLE B

| Example | CYP3A4 | CYP2D6 |
|---|---|---|
| 1 | 19 | 0.5 |
| 2 | 16 | 3 |
| 3 | 25 | 5 |
| 4 | 20 | 24 |
| 5 | 6 | 19 |
| 6 | 13 | 2 |
| 7 | nt | nt |
| 8 | nt | nt |
| 9 | 26 | nt |
| 10 | 9 | nt |
| 11 | >30 | 12 |
| 12 | 7.9 | nt |
| 13 | nt | nt |
| 14 | nt | nt |
| 15 | 27 | 18 |
| 16 | 19 | 7 |
| 17 | nt | nt |
| 18 | nt | nt |
| 19 | nt | nt |
| 20A/20B | nt | nt |
| 21A/21B | 15 | 3 |
| Mibefradil | 0.72 | 0.72 | nt = not tested

Example D. $C_{v3}$ Patch Clamp Recording

Whole-cell voltage clamp recordings were performed on cultured HEK293 cells expressing T-type channels (encoded by $Ca_{v3.1}$, $Ca_{v3.2}$, or $Ca_{v3.3}$ channels). All experiments were performed at room temperature. Whole-cell currents were recorded using a MultiClamp 700B amplifier and analyzed offline with pCLAMP10.4 software (Molecular Devices, LLC, Sunnyvale Calif., USA). To record calcium currents in HEK293 cells, the external solution was composed (in mM) of 115 choline-CL, 20 TEA-Cl, 2 CaCl2, 10 glucose and 10 HEPES (pH 7.3-7.4 adjusted with TEA-OH. Calcium currents were recorded at a holding potential of −100 mV and then depolarized to −30 mV for 100 ms to activate either Cav3.1, Cav3.2, or Cav3.3 expressed in HEK cells. An interpulse interval of 10 seconds allowed the channel recovery from inactivation, and achieved stable current recordings. The tip of resistance was 3-4 MΩ in batch and the series resistance was less than 10 MΩ after whole cell configuration. Test compounds were usually applied via a rapid solution exchange system with 8 fine polyplastic tubings glued in a holder in parallel and located closely to the recorded cells. The current responses were normalized to the control, percent inhibition was calculated and sigmoidal dose-response curettes we're generated using XLFIT (IDBS, Surrey, UK) or Prism (GraphPad Software, LA Jola, Calif., US) to calculate IC50 values and Hill slopes using the following equation Y=Bottom+(Top−Bottom)/1+10((Log EC50-X)−HillsSlope)). Representative results for T-type Cav3 channel inhibition are provided in Table C. IC50 values are given in micromolar units.

TABLE C

| Example | IC50 (uM) | | |
|---|---|---|---|
| | $Ca_{v3.1}$ | $Ca_{v3.2}$ | $Ca_{v3.3}$ |
| mibefradil | 0.341 | 0.727 | 0.198 |
| 15 | 0.139 | 0.335 | 0.212 |

OTHER EMBODIMENTS

Various modifications of the invention, in addition to those described herein, will be apparent to those skilled in the art from the foregoing description. It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

Each reference cited herein, including without limitation all patent, patent applications, and publications, cited in the present application is incorporated herein by reference in its entirety.

What is claimed is:
1. A compound of Formula I:

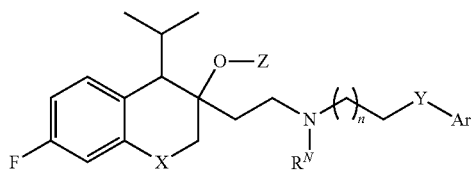

I or a pharmaceutically acceptable salt thereof, wherein:
X is O or $CH_2$;
Y is $CR^1R^2$, $NR^3$, C(=O), C(=O)NH, or NH(C=O);
Z is $C(=O)OR^{Z1}$, or $C(=O)NR^{Z2}R^{Z3}$;
n is 0, 1, 2, or 3;

$R^N$ is H or an optionally substituted $C_{1-4}$ alkyl;
$R^1$ is H or an optionally substituted $C_{1-4}$ alkyl;
$R^2$ is H or an optionally substituted $C_{1-4}$ alkyl; or
$R^1$ and $R^2$ in combination form a $C_{2-4}$ alkylene group which, together with the carbon atom to they are attached, form a 3-6-membered optionally substituted cycloalkyl ring;
$R^3$ is H or an optionally substituted $C_{1-4}$ alkyl;
$R^{Z1}$ is methyl;
$R^{Z2}$ is H or an optionally substituted $C_{1-4}$ alkyl;
$R^{Z3}$ is H or an optionally substituted $C_{1-4}$ alkyl; or
$R^{Z2}$ and $R^{Z3}$ in combination with the nitrogen atom to which they are attached form an optionally substituted 4-6 membered heterocycloalkyl ring; and
Ar is optionally substituted $C_{6-10}$ aryl, or a 5-10 membered optionally substituted heteroaryl; wherein each substituted $C_{1-4}$ alkyl is substituted by 1, 2, 3, 4 or 5 substituents, each independently selected from halo, $C_{1-4}$ alkyl, $C_{2-4}$ alkenyl, $C_{2-4}$ alkynyl, $C_{1-4}$ haloalkyl, $C_{1-4}$ alkoxy, OH, CN, $NO_2$, amino, $C_{1-4}$ alkylamino, di($C_{1-4}$ alkyl)amino, oxo, optionally substituted $C_{3-10}$ cycloalkyl, optionally substituted $C_{6-10}$ aryl, optionally substituted 4-10 membered heterocycloalkyl, and optionally substituted 5-10 membered heteroaryl; each substituted cycloalkyl and heterocycloalkyl is substituted by 1, 2, 3, 4 or 5 substituents, each independently selected from halo, $C_{1-4}$ alkyl, $C_{2-4}$ alkenyl, $C_{2-4}$ alkynyl, $C_{1-4}$ haloalkyl, $C_{1-4}$ alkoxy, OH, CN, $NO_2$, amino, $C_{1-4}$ alkylamino, di($C_{1-4}$ alkyl)amino and oxo; and each substituted aryl and heteroaryl is substituted by 1, 2, 3, 4, or 5 substituents, each independently selected from halo, $C_{1-4}$ alkyl, $C_{2-4}$ alkenyl, $C_{2-4}$ alkynyl, $C_{1-4}$ haloalkyl, $C_{1-4}$ alkoxy, OH, CN, $NO_2$, amino, $C_{1-4}$ alkylamino, and di($C_{1-4}$ alkyl)amino;
wherein when Ar is a 5-10 membered optionally substituted heteroaryl,
$R^1$ and $R^2$ are each an optionally substituted $C_{1-4}$ alkyl, or
$R^1$ and $R^2$ in combination form a $C_{2-4}$ alkylene group which, together with the carbon atom to they are attached, form a 3-6-membered optionally substituted cycloalkyl ring, or
$R^{Z2}$ is H or an unsubstituted $C_{1-4}$ alkyl and $R^{Z3}$ is methyl, N,N-dimethylaminoethyl, N,N-diethylaminoethyl, methoxyethyl, pyrrolidinylethyl, 2-(N,N-dimethylamino)ethyl, 2-(N,N-diethylamino)ethyl, 2-methoxyethyl, or 2-(pyrrolidin-1-yl)ethyl, or
$R^{Z2}$ and $R^{Z3}$ in combination with the nitrogen atom to which they are attached form an optionally substituted 4-6 membered heterocycloalkyl ring.

2. The compound of claim 1, or a pharmaceutically acceptable salt thereof, wherein Y is $CR^1R^2$.

3. The compound of claim 1, or a pharmaceutically acceptable salt thereof, wherein $R^N$ is an optionally substituted $C_{1-4}$ alkyl, and wherein said optionally substituted $C_{1-4}$ alkyl is methyl or ethyl.

4. The compound of claim 1, or a pharmaceutically acceptable salt thereof, wherein $R^1$ and $R^2$ are each H.

5. The compound of claim 1, or a pharmaceutically acceptable salt thereof, wherein $R^1$ and $R^2$ are each an optionally substituted $C_{1-4}$ alkyl, and wherein said optionally substituted $C_{1-4}$ alkyl is methyl.

6. The compound of claim 1, or a pharmaceutically acceptable salt thereof, wherein $R^1$ and $R^2$ in combination form a $C_{2-4}$ alkylene group which, together with the carbon atom to they are attached, form a 3-6-membered optionally substituted cycloalkyl ring, and wherein said optionally substituted cycloalkyl ring is an unsubstituted cyclopropyl ring.

7. The compound of claim 1, or a pharmaceutically acceptable salt thereof, wherein $R^3$ is an optionally substituted $C_{1-4}$ alkyl, and wherein said optionally substituted $C_{1-4}$ alkyl is an unsubstituted $C_{1-4}$ alkyl.

8. The compound of claim 1, or a pharmaceutically acceptable salt thereof, wherein Z is $C(=O)NR^{Z2}R^{Z3}$, wherein $R^{Z2}$ is methyl, and wherein $R^{Z3}$ is methyl, N,N-dimethylaminoethyl, N,N-diethylaminoethyl, methoxyethyl, pyrrolidinylethyl, 2-(N,N-dimethylamino)ethyl, 2-(N,N-diethylamino)ethyl, 2-methoxyethyl, or 2-(pyrrolidin-1-yl)ethyl.

9. The compound of claim 1, or a pharmaceutically acceptable salt thereof, wherein $R^{Z2}$ and $R^{Z3}$ in combination with the nitrogen atom to which they are attached form an optionally substituted 4-6 membered heterocycloalkyl ring, and wherein said is a morpholinyl ring.

10. The compound of claim 1, or a pharmaceutically acceptable salt thereof, wherein Ar is an optionally substituted aryl, and wherein said optionally substituted aryl is a phenyl or a naphthyl.

11. The compound of claim 1, or a pharmaceutically acceptable salt thereof, wherein Ar is a 5-10 membered heteroaryl optionally substituted heteroaryl, and wherein said optionally substituted heteroaryl is substituted by 1, 2, 3, or 4 groups independently selected from chloro, methyl, methoxy, and trifluoromethyl.

12. The compound of claim 1, or a pharmaceutically acceptable salt thereof, wherein Ar is:

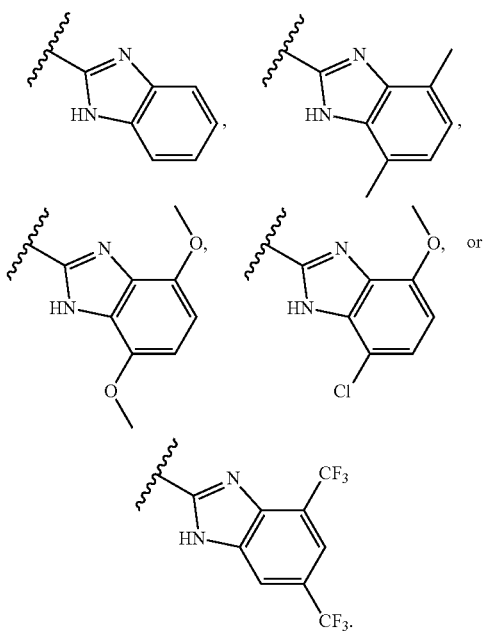

13. The compound of claim 1, or a pharmaceutically acceptable salt thereof, wherein:
X is O or $CH_2$;
Y is $CR^1R^2$;
Z is $C(=O)OR^{Z1}$, or $C(=O)NR^{Z2}R^{Z3}$;
$R^N$ is an unsubstituted $C_{1-4}$ alkyl;
$R^1$ is H or unsubstituted $C_{1-4}$ alkyl;
$R^2$ is H or unsubstituted $C_{1-4}$ alkyl; or
$R^1$ and $R^2$ in combination form a $C_{2-4}$ alkylene group which, together with the carbon atom to they are attached, form a 3-6-membered optionally substituted cycloalkyl ring;
n is 0, 1, 2, or 3;
$R^{Z1}$ is methyl;
$R^{Z2}$ is H or an unsubstituted $C_{1-4}$ alkyl;
$R^{Z3}$ is an optionally substituted $C_{1-4}$ alkyl; or
$R^{Z2}$ and $R^{Z3}$ in combination with the nitrogen atom to which they are attached form an optionally substituted 4-6 membered heterocycloalkyl ring; and
Ar is optionally substituted phenyl, optionally substituted naphthyl, or a 5-10 membered optionally substituted heteroaryl.

14. The compound of claim 1, or a pharmaceutically acceptable salt thereof, wherein:
X is O or $CH_2$;
Y is $CR^1R^2$;
Z is $C(=O)OR^{Z1}$, or $C(=O)NR^{Z2}R^{Z3}$;
$R^N$ is an unsubstituted $C_{1-4}$ alkyl;
$R^1$ is H or unsubstituted $C_{1-4}$ alkyl;
$R^2$ is H or unsubstituted $C_{1-4}$ alkyl; or
$R^1$ and $R^2$ in combination form a $C_{2-4}$ alkylene group which, together with the carbon atom to they are attached, form a 3-6-membered optionally substituted cycloalkyl ring;
n is 1;
$R^{Z1}$ is methyl;
$R^{Z2}$ is H or an unsubstituted $C_{1-4}$ alkyl;
$R^{Z3}$ is methyl, N,N-dimethylaminoethyl, N,N-diethylaminoethyl, methoxyethyl, pyrrolidinylethyl, 2-(N,N-dimethylamino)ethyl, 2-(N,N-diethylamino)ethyl, 2-methoxyethyl, or 2-(pyrrolidin-1-yl)ethyl, or $R^{Z2}$ and $R^{Z3}$ in combination with the nitrogen atom to which they are attached form an optionally substituted 4-6 membered heterocycloalkyl ring; and
Ar is a 5-10 membered optionally substituted heteroaryl.

15. The compound of claim 1, or a pharmaceutically acceptable salt thereof, wherein:
X is O or $CH_2$;
Y is $CR^1R^2$;
Z is $C(=O)OR^{Z1}$, or $C(=O)NR^{Z2}R^{Z3}$;
$R^N$ is an unsubstituted $C_{1-4}$ alkyl;
$R^1$ is H or methyl;
$R^2$ is H or methyl; or
$R^1$ and $R^2$ in combination form an ethylene group which, together with the carbon atom to they are attached, form a cyclopropyl ring;
n is 1;
$R^{Z1}$ is methyl;
$R^{Z2}$ is H or an unsubstituted $C_{1-4}$ alkyl;
$R^{Z3}$ is methyl, N,N-dimethylaminoethyl, N,N-diethylaminoethyl, methoxyethyl, pyrrolidinylethyl, 2-(N,N-dimethylamino)ethyl, 2-(N,N-diethylamino)ethyl, 2-methoxyethyl, or 2-(pyrrolidin-1-yl)ethyl, or $R^{Z2}$ and $R^{Z3}$ in combination with the nitrogen atom to which they are attached form an optionally substituted 4-6 membered heterocycloalkyl ring; and
Ar is a 5-10 membered heteroaryl optionally substituted by 1, 2, 3, or 4 groups independently selected from halo, $C_{1-4}$ alkyl, $C_{1-4}$ haloalkyl, and $C_{1-4}$ alkoxy.

16. The compound of claim 1, wherein the compound of Formula I is selected from the group consisting of:

a compound of Formula II:

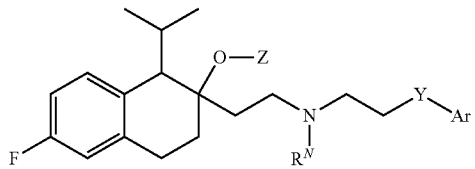

II or a pharmaceutically acceptable salt thereof, a compound of Formula III:

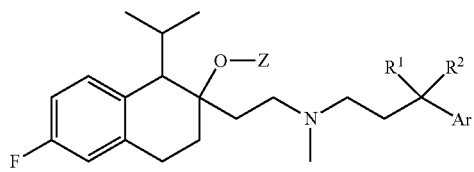

III or a pharmaceutically acceptable salt thereof;

a compound of Formula IV:

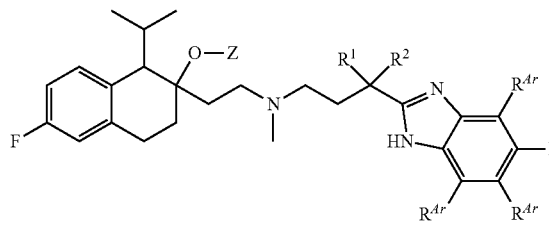

IV or a pharmaceutically acceptable salt thereof, wherein each $R^A r$ is independently selected from H, halo, $C_{1-4}$ alkyl, $C_{1-4}$ haloalkyl, and $C_{1-4}$ alkoxy;

a compound of Formula V:

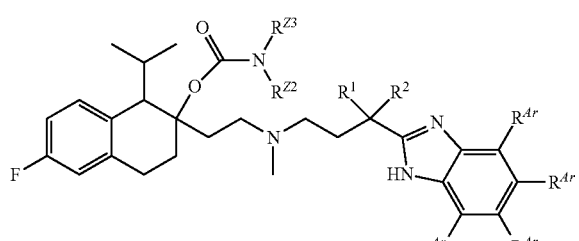

V or a pharmaceutically acceptable salt thereof, wherein each $R^A r$ is independently selected from H, halo, $C_{1-4}$ alkyl, $C_{1-4}$ haloalkyl, and $C_{1-4}$ alkoxy; and a compound of Formula I-a, I-b, II-a, II-b, III-a, III-b, IV-a, IV-b, V-a, or V-b:

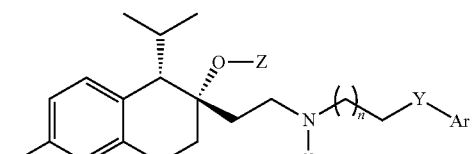

I-a

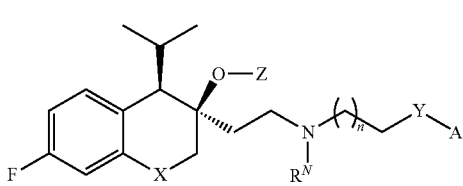

I-b

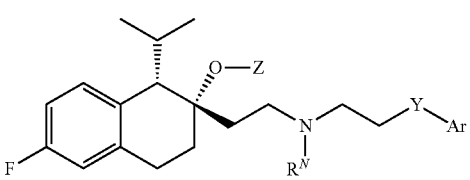

II-a

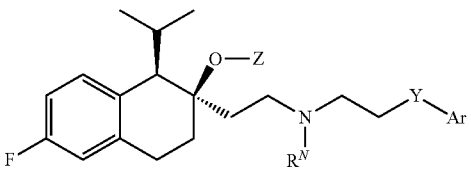

II-b

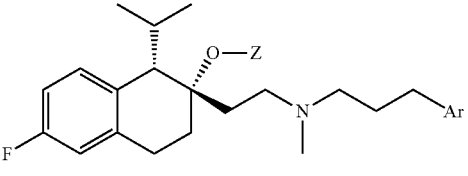

III-a

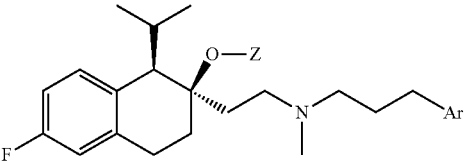

III-b

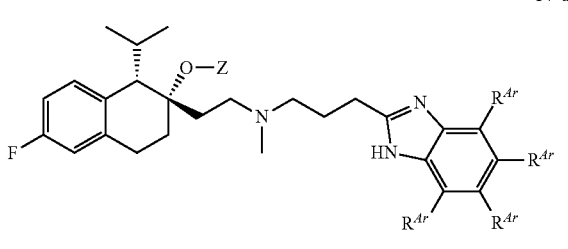

IV-a

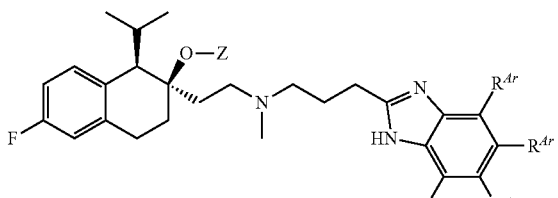

IV-b

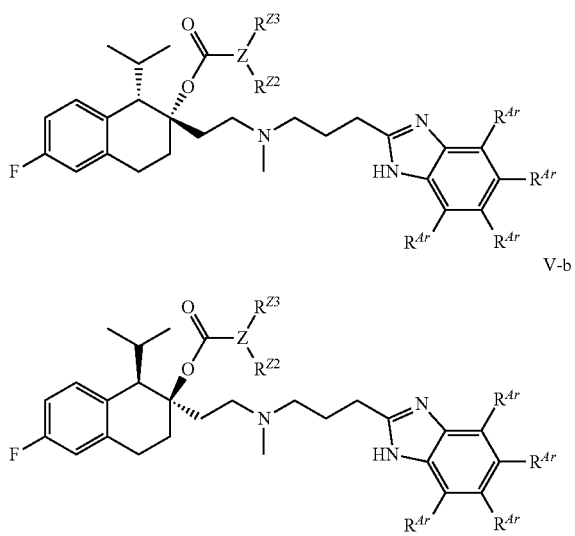

V-a

V-b or a pharmaceutically acceptable salt thereof, wherein each $R^Ar$ is independently selected from H, halo, $C_{1-4}$ alkyl, $C_{1-4}$ haloalkyl, and $C_{1-4}$ alkoxy.

17. The compound of claim 1, wherein the compound is selected from: 2-(2-((3-(1H-benzo[d]imidazol-2-yl)propyl)(methyl)amino)ethyl)-6-fluoro-1-isopropyl-1,2,3,4-tetrahydronaphthalen-2-yl methylcarbamate;
- 2-(2-((3-(1H-benzo[d]imidazol-2-yl)propyl)(methyl)amino)ethyl)-6-fluoro-1-isopropyl-1,2,3,4-tetrahydronaphthalen-2-yl methylcarbonate;
- 2-(2-((3-(4,7-dimethyl-1H-benzo[d]imidazol-2-yl)propyl)(methyl)amino)ethyl)-6-fluoro-1-isopropyl-1,2,3,4-tetrahydronaphthalen-2-yl methylcarbamate;
- 2-(2-((3-(4,7-dimethyl-1H-benzo[d]imidazol-2-yl)propyl)(methyl)amino)ethyl)-6-fluoro-1-isopropyl-1,2,3,4-tetrahydronaphthalen-2-yl (2-(dimethylamino)ethyl)carbamate;
- 2-(2-((3-(4,7-dimethoxy-1H-benzo[d]imidazol-2-yl)propyl)(methyl)amino)ethyl)-6-fluoro-1-isopropyl-1,2,3,4-tetrahydronaphthalen-2-yl methylcarbamate;
- 2-(2-((3-(4,7-dimethoxy-1H-benzo[d]imidazol-2-yl)propyl)(methyl)amino)ethyl)-6-fluoro-1-isopropyl-1,2,3,4-tetrahydronaphthalen-2-yl (2-methoxyethyl)carbamate;
- 2-(2-((3-(7-chloro-4-methoxy-1H-benzo [d]imidazol-2-yl)propyl)(methyl)amino)ethyl)-6-fluoro-1-isopropyl-1,2,3,4-tetrahydronaphthalen-2-yl dimethylcarbamate;
- 2-(2-((3-(4, 6-bi s(trifluoromethyl)-1H-benzo[d]imidazol-2-yl)propyl)(methyl)amino)ethyl)-6-fluoro-1-isopropyl-1,2,3,4-tetrahydronaphthalen-2-yl morpholine-4-carboxylate;
- 2-(2-((3-(1H-benzo[d]imidazol-2-yl)-3-methylbutyl)(methyl)amino)ethyl)-6-fluoro-1-isopropyl-1,2,3,4-tetrahydronaphthalen-2-yl morpholine-4-carboxylate;
- 2-(2-((3-(1H-benzo[d]imidazol-2-yl)-3-methylbutyl)(methyl)amino)ethyl)-6-fluoro-1-isopropyl-1,2,3,4-tetrahydronaphthalen-2-yl methylcarbamate;
- 2-(2-((3-(1H-benzo[d]imidazol-2-yl)-3-methylbutyl)(methyl)amino)ethyl)-6-fluoro-1-isopropyl-1,2,3,4-tetrahydronaphthalen-2-yl (2-(dimethylamino)ethyl)carbamate;
- 2-(2-((3-(1H-benzo[d]imidazol-2-yl)-3-methylbutyl)(methyl)amino)ethyl)-6-fluoro-1-isopropyl-1,2, 3,4-tetrahydronaphthalen-2-yl (2-methoxyethyl)carbamate;
- 2-(2-((3-(1H-benzo[d]imidazol-2-yl)-3-methylbutyl)(methyl)amino)ethyl)-6-fluoro-1-isopropyl-1,2,3,4-tetrahydronaphthalen-2-yl (2-(pyrrolidin-1-yl)ethyl)carbamate;
- 2-(2-((3-(1H-benzo[d]imidazol-2-yl)-3-methylbutyl)(methyl)amino)ethyl)-6-fluoro-1-isopropyl-1,2,3,4-tetrahydronaphthalen-2-yl (2-(diethylamino)ethyl)carbamate;
- 2-(2-((3-(4, 7-dimethyl-1H-benzo[d]imidazol-2-yl)propyl)(methyl)amino)ethyl)-6-fluoro-1-isopropyl-1,2,3, 4-tetrahydronaphthalen-2-yl morpholine-4-carboxylate;
- 2-(2-((3-(4, 7-dimethyl-1H-benzo[d]imidazol-2-yl)propyl)(methyl)amino)ethyl)-6-fluoro-1-isopropyl-1,2,3, 4-tetrahydronaphthalen-2-yl dimethylcarbamate;
- 2-(2-((4-((2-amino-3, 6-dimethy 1 pheny 1)amino)-4-oxobuty 1)(ethy 1)amino)ethy 1)-6-fluoro-1-isopropyl-1,2,3,4-tetrahydronaphthalen-2-yl morpholine-4-carboxylate;
- 2-(2-((2-(1-(1H-benzo[d]imidazol-2-yl)cyclopropyl)ethyl)(methyl)amino)ethyl)-6-fluoro-1-isopropyl-1,2, 3,4-tetrahydronaphthalen-2-yl morpholine-4-carboxylate;
- 3-(24(3-(1H-benzo[d]imidazol-2-yl)propyl)(methyl)amino)ethyl)-7-fluoro-4 isopropylchroman-3-yl methylcarbamate;
- 3-(24(3-(4, 7-dimethyl-1H-benzo[d]imidazol-2-yl)propyl)(methyl)amino)ethyl)-7-fluoro-4-isopropylchroman-3-yl methylcarbamate;
- (1S,2S)-2-(2-((3-(1H-benzo[d]imidazol-2-yl)propyl)(methyl)amino)ethyl)-6-fluoro-1-isopropyl-1,2,3,4-tetrahydronaphthalen-2-yl methylcarbamate;
- (1S,2S)-2-(2-((3-(1H-benzo[d]imidazol-2-yl)propyl)(methyl)amino)ethyl)-6-fluoro-1-isopropyl-1,2,3,4-tetrahydronaphthalen-2-yl methylcarbonate;
- (1S,2S)-2-(2-((3-(4,7-dimethyl-1H-benzo[d]imidazol-2-yl)propyl)(methyl)amino)ethyl)-6-fluoro-1-isopropyl-1,2,3,4-tetrahydronaphthalen-2-yl methylcarbamate;
- (1S,2S)-2-(2-((3-(4,7-dimethyl-1H-benzo[d]imidazol-2-yl)propyl)(methyl)amino)ethyl)-6-fluoro-1-isopropyl-1,2,3,4-tetrahydronaphthalen-2-yl (2-(dimethylamino)ethyl)carbamate;
- (1S,2S)-2-(2-((3-(4,7-dimethoxy-1H-benzo[d]imidazol-2-yl)propyl)(methyl)amino)ethyl)-6-fluoro-1-isopropyl-1,2,3,4-tetrahydronaphthalen-2-yl methylcarbamate;
- (1S,2S)-2-(2-((3-(4,7-dimethoxy-1H-benzo[d]imidazol-2-yl)propyl)(methyl)amino)ethyl)-6-fluoro-1-isopropyl-1,2,3,4-tetrahydronaphthalen-2-yl (2-methoxyethyl)carbamate;
- (1S,2S)-2-(2-((3-(7-chloro-4-methoxy-1H-benzo [d]imidazol-2-yl)propyl)(methyl)amino)ethyl)-6-fluoro-1-isopropyl-1,2,3,4-tetrahydronaphthalen-2-yl dimethylcarbamate;
- (1S,2S)-2-(2-((3-(4,6-bis(trifluoromethyl)-1H-benzo[d]imidazol-2-yl)propyl)(methyl)amino)ethyl)-6-fluoro-1-isopropyl-1,2,3,4-tetrahydronaphthalen-2-yl morpholine-4-carboxylate;
- (1S,2S)-2-(2-((3-(1H-benzo[d]imidazol-2-yl)-3-methylbutyl)(methyl)amino)ethyl)-6-fluoro-1-isopropyl-1,2, 3,4-tetrahydronaphthalen-2-yl morpholine-4-carboxylate;
- (1S,2S)-2-(2-((3-(1H-benzo[d]imidazol-2-yl)-3-methylbutyl)(methyl)amino)ethyl)-6-fluoro-1-isopropyl-1,2, 3,4-tetrahydronaphthalen-2-yl methylcarbamate;

(1S,2S)-2-(2-((3-(1H-benzo[d]imidazol-2-yl)-3-methylbutyl)(methyl)amino)ethyl)-6-fluoro-1-isopropyl-1,2,3,4-tetrahydronaphthalen-2-yl (2-(dimethylamino)ethyl)carbamate;

(1S,2S)-2-(2-((3-(1H-benzo[d]imidazol-2-yl)-3-methylbutyl)(methyl)amino)ethyl)-6-fluoro-1-isopropyl-1,2,3,4-tetrahydronaphthalen-2-yl (2-methoxyethyl)carbamate;

(1S,2S)-2-(2-((3-(1H-benzo[d]imidazol-2-yl)-3-methylbutyl)(methyl)amino)ethyl)-6-fluoro-1-isopropyl-1,2,3,4-tetrahydronaphthalen-2-yl (2-(pyrrolidin-1-yl)ethyl)carbamate;

(1S,2S)-2-(2-((3-(1H-benzo[d]imidazol-2-yl)-3-methylbutyl)(methyl)amino)ethyl)-6-fluoro-1-isopropyl-1,2,3,4-tetrahydronaphthalen-2-yl (2-(diethylamino)ethyl) carbamate;

(1S,2S)-2-(2-((3-(4,7-dimethyl-1H-benzo[d]imidazol-2-yl)propyl)(methyl)amino)ethyl)-6-fluoro-1-isopropyl-1,2,3,4-tetrahydronaphthalen-2-yl morpholine-4-carboxylate;

(1S,2S)-2-(2-((3-(4,7-dimethyl-1H-benzo[d]imidazol-2-yl)propyl)(methyl)amino)ethyl)-6-fluoro-1-isopropyl-1,2,3,4-tetrahydronaphthalen-2-yl dimethylcarbamate;

(1R,2R)-2-(2-((3-(4,7-dimethyl-1H-benzo[d]imidazol-2-yl)propyl)(methyl)amino)ethyl)-6-fluoro-1-isopropyl-1,2,3,4-tetrahydronaphthalen-2-yl morpholine-4-carboxylate;

(1S,2S)-2-(2-((4-((2-amino-3,6-dimethylphenyl)amino)-4-oxobutyl)(ethyl)amino)ethyl)-6-fluoro-1-isopropyl-1,2,3,4-tetrahydronaphthalen-2-yl morpholine-4-carboxylate;

(1S,2S)-2-(24(2-(1-(1H-benzo[d]imidazol-2-yl)cyclopropyl)ethyl)(methyl)amino)ethyl)-6-fluoro-1-isopropyl-1,2,3,4-tetrahydronaphthalen-2-yl morpholine-4-carboxylate;

(3S,4S)-3-(24(3-(1H-benzo[d]imidazol-2-yl)propyl)(methyl)amino)ethyl)-7-fluoro-4-isopropylchroman-3-yl methylcarbamate;

(3R,4S)-3-(24(3-(1H-benzo[d]imidazol-2-yl)propyl)(methyl)amino)ethyl)-7-fluoro-4-isopropylchroman-3-yl methylcarbamate;

(3 S,4S)-3-(2-((3-(4,7-dimethyl-1H-benzo[d]imidazol-2-yl)propyl)(methyl)amino)ethyl)-7-fluoro-4-isopropylchroman-3-yl methylcarbamate; and (3R,4S)-3-(24(3-(4, 7-dimethyl-1H-benzo[d]imidazol-2-yl)propyl)(methyl)amino)ethyl)-7-fluoro-4-isopropyl chroman-3-yl methylcarbamate;

or a pharmaceutically acceptable salt thereof.

18. A pharmaceutical composition comprising a compound of claim 1, or a pharmaceutically acceptable salt thereof, and a pharmaceutically acceptable carrier.

19. A method of ameliorating a seizure disorder or epilepsy, comprising administering to a subject in need thereof a therapeutically effective amount of a compound of claim 1, or a pharmaceutically acceptable salt thereof.

20. The compound of claim 1 having the formula

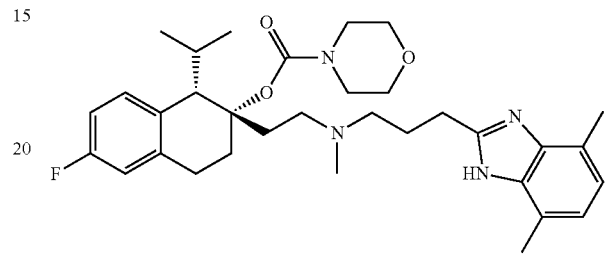

or a pharmaceutically acceptable salt thereof.

21. The method of claim 19 wherein the compound has the formula

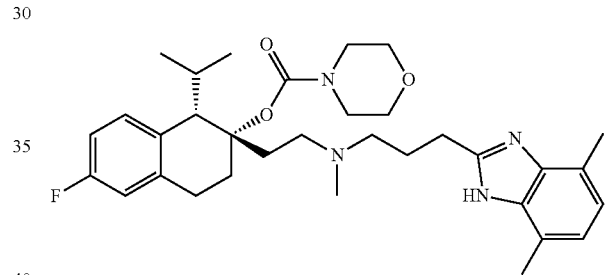

or a pharmaceutically acceptable salt thereof.

* * * * *